(12) United States Patent
Favuzzi et al.

(10) Patent No.: US 7,875,245 B2
(45) Date of Patent: Jan. 25, 2011

(54) METHOD AND APPARATUS FOR AUTOMATED PRE-TREATMENT AND PROCESSING OF BIOLOGICAL SAMPLES

(75) Inventors: John A. Favuzzi, Santa Barbara, CA (US); Kristopher S. Buchanan, Fort Collins, CO (US); Michael T. Barber, Fort Collins, CO (US); Loren L. Bland, Carpinteria, CA (US); Dawn M. Rohrbacker, Fort Collins, CO (US); Robert M. Clark, Loveland, CO (US); Gordon A. Feingold, Santa Barbara, CA (US); Benno M. Guggenheimer, Santa Monica, CA (US); Marc E. Key, Ojai, CA (US); Merritt M. Martin, Jr., Fort Collins, CO (US); Robert L. Lathrop, San Jose, CA (US); Jeffery L. Rau, Fort Collins, CO (US); Jonathan R. Sweda, Fort Collins, CO (US); Douglas F. Sweet, Santa Barbara, CA (US); John E. Van Bosch, Ventura, CA (US); Lars Winther, Smoerum (DK); Rosanne Welcher, Ventura, CA (US)

(73) Assignee: DAKO Denmark A/S (DK)

( * ) Notice: Subject to any disclaimer, the term of this patent is extended or adjusted under 35 U.S.C. 154(b) by 976 days.

(21) Appl. No.: 11/156,760

(22) Filed: Jun. 20, 2005

(65) Prior Publication Data
US 2006/0105359 A1     May 18, 2006

(30) Foreign Application Priority Data
May 14, 2003    (EP)    .................................. 03076463

(51) Int. Cl.
*B01L 3/02* (2006.01)
(52) U.S. Cl. ........................... 422/100; 422/63; 422/67; 422/102; 436/43; 436/46; 436/55; 436/180
(58) Field of Classification Search ............... 435/6, 435/287.2; 422/100, 63, 67, 102; 702/20; 436/43, 46, 55, 180
See application file for complete search history.

(56) References Cited

U.S. PATENT DOCUMENTS 4,311,667 A    1/1982    Gocho (Continued)

FOREIGN PATENT DOCUMENTS

DE    4313807    11/1993

(Continued)

OTHER PUBLICATIONS

Juroshek et al., A High-Power Automatic Network Analyzer for Measuring the RF Power Absorbed by Biological Samples in a TEM Cell, 1984, IEEE, gpo 818-824.

Meldrum et al., ACAPELLA, a capillary-based submicroliter automated sample preparation system for genome analysis, 1999, IEEE, p. 39-48.

(Continued)

*Primary Examiner*—Jill Warden
*Assistant Examiner*—Dwayne K Handy
(74) *Attorney, Agent, or Firm*—Finnegan, Henderson, Farabow, Garrett & Dunner, LLP

(57) ABSTRACT

The present invention concerns a method and apparatus for automatic processing a biological sample on a carrier, perhaps robotically, by applying predetermined amounts of reagents in a predetermined sequence according to a processing protocol, the processing including pre-treatment steps, under the control of an adaptive processing control system using a sample process parameter input that may be independent and an independent process parameter memory that does not interrupt process operation when being used, such that samples may be added or removed without interrupting the processing of other samples. Also included is an image capture function for sample and reagent identification and process monitoring, as well as temperature regulation and environmental control functions.

33 Claims, 41 Drawing Sheets

U.S. PATENT DOCUMENTS

| | | | |
|---|---|---|---|
| 4,967,606 A | 11/1990 | Wells et al. | |
| 5,068,091 A | 11/1991 | Toya | |
| 5,073,504 A | 12/1991 | Bogen | |
| 5,289,385 A | 2/1994 | Grandone | |
| 5,338,358 A | 8/1994 | Mizusawa et al. | |
| 5,346,672 A | 9/1994 | Stapleton et al. | |
| 5,355,439 A | 10/1994 | Bernstein et al. | |
| 5,380,486 A | 1/1995 | Anami | |
| 5,399,316 A | 3/1995 | Yamada | |
| 5,425,918 A | 6/1995 | Healey et al. | |
| 5,439,649 A | 8/1995 | Tseung et al. | |
| 5,552,087 A | 9/1996 | Zeheb et al. | |
| 5,573,727 A | 11/1996 | Keefe | |
| 5,578,452 A | 11/1996 | Shi et al. | |
| 5,595,707 A | 1/1997 | Copeland et al. | |
| 5,646,049 A | 7/1997 | Tayi | |
| 5,650,327 A | 7/1997 | Copeland et al. | |
| 5,654,199 A | 8/1997 | Copeland et al. | |
| 5,654,200 A | 8/1997 | Copeland et al. | |
| 5,696,887 A | 12/1997 | Bernstein et al. | |
| 5,839,091 A | 11/1998 | Rhett et al. | |
| 5,896,488 A | 4/1999 | Jeong | |
| 5,948,359 A * | 9/1999 | Kalra et al. | 422/65 |
| 5,963,368 A | 10/1999 | Domanik et al. | |
| 6,045,759 A | 4/2000 | Ford et al. | |
| 6,080,363 A | 6/2000 | Takahashi et al. | |
| 6,093,574 A | 7/2000 | Druyor-Sanchez et al. | |
| 6,096,271 A | 8/2000 | Bogen et al. | |
| 6,183,693 B1 * | 2/2001 | Bogen et al. | 422/64 |
| 6,296,809 B1 | 10/2001 | Richards et al. | |
| 6,349,264 B1 | 2/2002 | Rhett et al. | |
| 6,352,861 B1 | 3/2002 | Copeland et al. | |
| 6,403,036 B1 | 6/2002 | Rodgers et al. | |
| 6,403,931 B1 | 6/2002 | Showalter et al. | |
| 6,405,609 B1 | 6/2002 | Richards et al. | |
| 6,451,551 B1 | 9/2002 | Zhan et al. | |
| 6,472,217 B1 | 10/2002 | Richards et al. | |
| 6,495,106 B1 | 12/2002 | Kalra et al. | |
| 6,534,008 B1 | 3/2003 | Angros | |
| 6,544,798 B1 | 4/2003 | Christensen et al. | |
| 6,582,962 B1 | 6/2003 | Richards et al. | |
| 6,632,598 B1 | 10/2003 | Zhang et al. | |
| 6,635,225 B1 | 10/2003 | Thiem et al. | |
| 6,716,396 B1 * | 4/2004 | Anderson et al. | 422/99 |
| 6,735,531 B2 | 5/2004 | Rhett et al. | |
| 6,746,851 B1 | 6/2004 | Tseung et al. | |
| 6,800,249 B2 * | 10/2004 | de la Torre-Bueno | 422/63 |
| 6,821,072 B2 | 11/2004 | Thiem et al. | |
| 6,855,559 B1 | 2/2005 | Christensen et al. | |
| 6,998,270 B2 * | 2/2006 | Tseung et al. | 436/46 |
| 7,135,992 B2 | 11/2006 | Karlsson et al. | |
| 7,142,852 B2 | 11/2006 | Tell et al. | |
| 7,226,788 B2 | 6/2007 | De La Torre-Bueno | |
| 7,303,725 B2 | 12/2007 | Reinhardt et al. | |
| 7,378,055 B2 | 5/2008 | Lemme et al. | |
| 7,396,508 B1 | 7/2008 | Richards et al. | |
| 7,400,983 B2 | 7/2008 | Feingold et al. | |
| 7,404,927 B2 | 7/2008 | Lemme et al. | |
| 2002/0001849 A1 | 1/2002 | Copeland et al. | |
| 2002/0072122 A1 | 6/2002 | Copeland et al. | |
| 2002/0114733 A1 | 8/2002 | Copeland et al. | |
| 2003/0099573 A1 | 5/2003 | Tseung et al. | |
| 2003/0100043 A1 | 5/2003 | Kalra et al. | |
| 2003/0120633 A1 | 6/2003 | Torre-Bueno | |
| 2004/0033163 A1 | 2/2004 | Tseung et al. | |
| 2004/0219069 A1 | 11/2004 | Kalra et al. | |
| 2004/0265185 A1 | 12/2004 | Kitagawa | |
| 2004/0266015 A1 | 12/2004 | Favuzzi et al. | |
| 2005/0038676 A1 | 2/2005 | Showalter et al. | |
| 2005/0064535 A1 | 3/2005 | Favuzzi et al. | |
| 2005/0124028 A1 | 6/2005 | Windeyer et al. | |
| 2005/0159982 A1 | 7/2005 | Showalter et al. | |
| 2006/0045806 A1 | 3/2006 | Winther et al. | |
| 2006/0046298 A1 | 3/2006 | Key et al. | |
| 2006/0063265 A1 | 3/2006 | Welcher et al. | |
| 2006/0085140 A1 | 4/2006 | Feingold et al. | |
| 2006/0088928 A1 | 4/2006 | Sweet et al. | |
| 2006/0088940 A1 | 4/2006 | Feingold et al. | |
| 2006/0105359 A1 | 5/2006 | Favuzzi et al. | |
| 2006/0148063 A1 | 7/2006 | Fauzzi et al. | |
| 2006/0265133 A1 | 11/2006 | Cocks et al. | |
| 2007/0010912 A1 | 1/2007 | Feingold et al. | |
| 2007/0196909 A1 | 8/2007 | Showalter et al. | |

FOREIGN PATENT DOCUMENTS

| | | |
|---|---|---|
| JP | 03209163 A2 | 12/1991 |
| WO | WO 95/10035 | 4/1995 |
| WO | WO 97/26541 | 7/1997 |
| WO | WO 99/43434 | 9/1999 |
| WO | WO 00/02660 | 1/2000 |
| WO | WO 01/51909 | 7/2001 |
| WO | WO 01/68259 | 9/2001 |
| WO | WO 01/88500 | 11/2001 |
| WO | WO 02/056121 | 7/2002 |
| WO | WO 02/064812 | 8/2002 |
| WO | WO 03/045560 | 6/2003 |
| WO | WO 03/052386 | 6/2003 |
| WO | WO 2004/074845 | 9/2004 |
| WO | WO 2004/074847 | 9/2004 |
| WO | WO 2005/031312 | 4/2005 |

OTHER PUBLICATIONS

Shepard, DNA purification robotics system, 1994, IEEE, gpo 424-425.

Suckau et al., Automation of MALDI-TOF Analysis for Proteomics, 1999, IEEE, p. 1-5.

Histologic, Technical Bulletin for Histotechnology, 2001, Internet, p. 21-44.

Garrett et al., Successful techniques for supporting multidisciplinary science programs with 'ROPOS: 1999, IEEE, p. 753-756.

Office Action dated Mar. 18, 2010 issued in U.S. Appl. No. 10/538,964, filed Jun. 14, 2005, Sweet et al.

Office Action dated Apr. 15, 2010, issued in U.S. Appl. No. 10/539,561, filed Jun. 16, 2005, Key et al.

* cited by examiner

| Process | Protocol Step | Time (min) | Temp C | Waste Segregation |
|---|---|---|---|---|
| Deparaffinization | Switch | | | Hazardous Waste |
| | Histoclear | 5 | | |
| | Drain | | | |
| | Histoclear | 5 | | |
| | Drain | | | |
| Re-Hydration | 100% Ethanol | 5 | | |
| | Drain | | | |
| | 100% Ethanol | 5 | | |
| | Drain | | | |
| | 95% Ethanol | 5 | | |
| | Drain | | | |
| | 95% Ethanol | 5 | | |
| | Rinse - Water | 5 | | |
| | Switch | | | Non-Hazardous Waste |
| Target Retrieval | Target Retrieval | 20 | 95 | |
| | Target Retrieval Cool | 20 | 55 | |
| | Rinse - Water | 5 | RT | |
| Enzyme/Antibody Application | Peroxide Block | 5 | | |
| | Enzyme Pretreatment | 5 | | |
| | Rinse - Buffer | | | |
| | Pre-Diluted Antibody | 10 | | |
| | Rinse - Buffer | | | |
| | EnVision-HRP | 10 | | |
| Chromogen/ Counterstain Treatment | Rinse - Buffer | | | |
| | Switch | | | Hazardous Waste |
| | DAB | 5 | | |
| | Rinse - Buffer | | | |
| | Hematoxylin | 5 | | |
| | Rinse - Water | | | |

FIG. 5

FIG. 35A
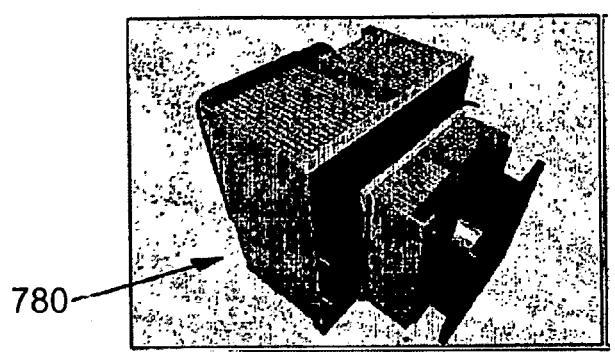
780
FIG. 35B
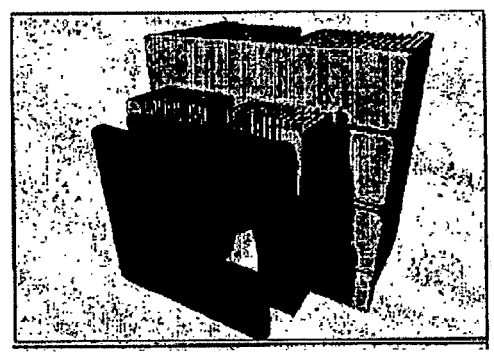
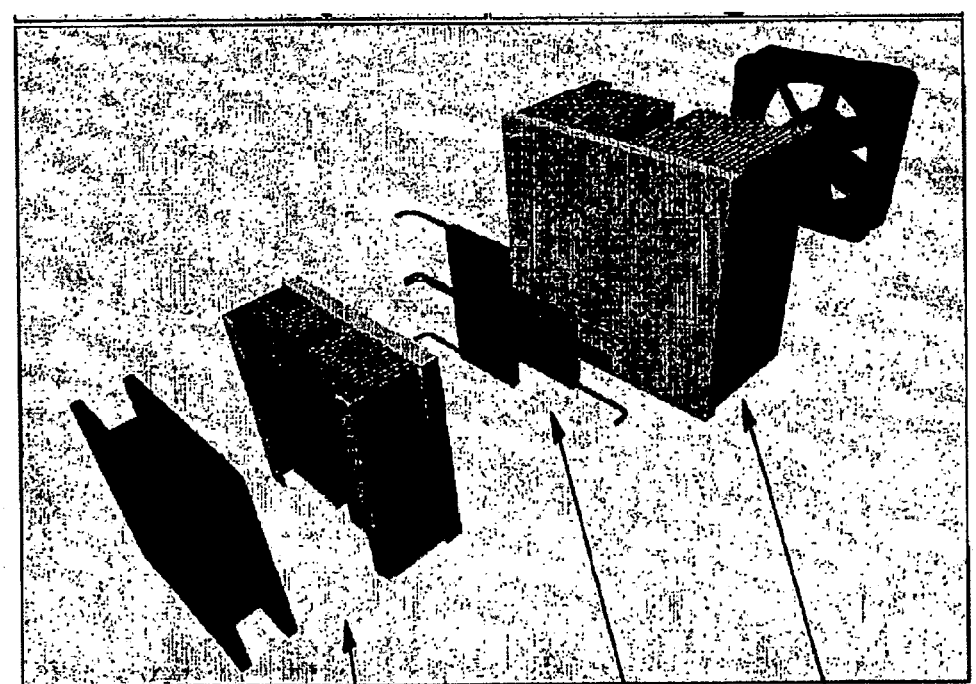
FIG. 35C
780a  781  780b

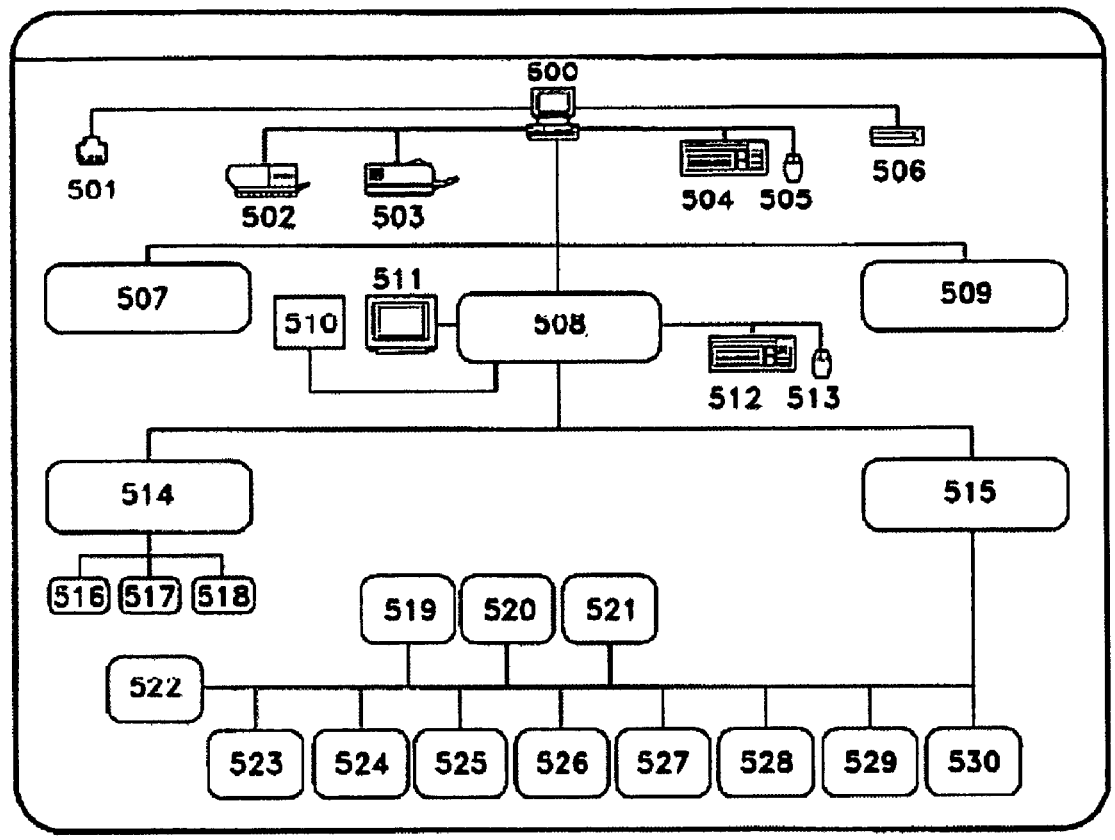

Key to Figure 39

| | |
|---|---|
| 500 Manager | 516 X-Axis |
| 501 100 BaseT | 517 Y-Axis |
| 502 Laser printer | 518 Z-Axis |
| 503 Label Printer | 519 LCD Touch |
| 504 Keyboard | 520 Probe Wash/Swap |
| 505 Mouse | 521 Misc PCBA |
| 506 Storage Media | 522 Cart PCBA |
| 507 Stainer A Embedded PC | 523 Drawer 1 Control |
| 508 Stainer B Embedded PC | 524 Drawer 2 Control |
| 509 Stainer C Embedded PC | 525 Drawer 3 Control |
| 510 Touch Screen | 526 Drawer 4 Control |
| 511 Monitor | 527 Drawer 5 Control |
| 512 Keyboard | 528 Drawer 6 Control |
| 513 Mouse | 529 Drawer 7 Control |
| 514 Motor Controller | 530 Drawer 8 Control |
| 515 Master PCBA | |

FIG. 39

METHOD AND APPARATUS FOR AUTOMATED PRE-TREATMENT AND PROCESSING OF BIOLOGICAL SAMPLES

CROSS REFERENCE TO RELATED APPLICATIONS

This application is a continuation-in-part of co-pending international application PCT/DK2003/000877, titled "Method and Apparatus for Pretreatment of Biological Samples" having an international filing date of Dec. 15, 2003 and designating the United States of America; is also a continuation-in-part of co-pending international application PCT/DK2003/000911, titled "An Automated Sample Processing Apparatus and a Method of Automated Treating of Samples and Use of Such Apparatus" having an international filing date of Dec. 19, 2003 and designating the United States of America; is also a continuation-in-part of co-pending international application PCT/US2003/040518, titled "A Method and Apparatus for Automatic Staining of Tissue Samples" having an international filing date of Dec. 19, 2003 and designating the United States of America; is also a continuation-in-part of co-pending international application PCT/US2003/040880, titled "Systems and Methods of Sample Processing and Temperature Control" having an international filing date of Dec. 22, 2003 and designating the United States of America; is also a continuation-in-part of co-pending international application PCT/US2003/040591, titled "Enhanced Scheduling Sample Processing System and Methods of Biological Slide Processing" having an international filing date of Dec. 19, 2003 and designating the United States of America; is also a continuation-in-part of co-pending international application PCT/US2003/040520, titled "Apparatus for Automated Processing Biological Samples" having an international filing date of Dec. 19, 2003 and designating the United States of America; is also a continuation-in-part of co-pending international application PCT/US2005/006383 titled "Reagent Delivery System, Dispensing Device and Container for a Biological Staining Apparatus" having an international filing date of Feb. 28, 2005 and designating the United States of America; is also a continuation-in-part of co-pending international application PCT/US2003/041022 titled "Isolated Communication Sample Processing System and Methods of Biological Slide Processing" having an international filing date of Dec. 22, 2003 and designating the United States of America; is also a continuation-in-part of co-pending international application PCT/US2003/040974 titled "Information Notification Sample Processing System and Methods of Biological Slide Processing" having an international filing date of Dec. 19, 2003 and designating the United States of America; is also a continuation-in-part of co-pending international application PCT/US2003/040519 titled "Advanced Programmed Sample Processing System and Methods of Biological Slide Processing" having an international filing date of Dec. 19, 2003 and designating the United States of America; also claims the benefit of the filing date of and the right of priority to U.S. Provisional Application 60/435,601 filed Dec. 20, 2002; further claims the benefit of the filing date of and the right of priority to U.S. Provisional Application 60/549,889 filed on Mar. 2, 2004; and further claims the benefit of the filing date of and the right of priority to European Patent Office Application 03076463.3 filed on May 14, 2003. Each of the above-referenced patent applications is hereby incorporated by reference, in its respective entirety. Also hereby incorporated by reference, in its respective entirety, is each one of the patent application publications corresponding to the above-referenced international applications, said patent application publications being, namely, international patent application publication WO 2004/057307 A1, international patent application publication WO 2004/057308 A1, international patent application publication WO 2004/058950 A1, international patent application publication WO 2004/059287 A2, international patent application publication WO 2004/058404 A2, international patent application publication WO 2004/059284 A2, international patent application publication WO 2004/059288 A2, international patent application publication WO 2004/059441 A2, and international patent application publication WO 2004/059297 A1. This application is further related to co-pending U.S. patent application Ser. No. 10/741,628 filed on Dec. 19, 2003, to U.S. patent application Ser. No. 10/731,316 filed on Dec. 8, 2003 and to U.S. patent application Ser. No. 11/119,417, filed on Apr. 30, 2005.

FIELD OF THE INVENTION

The present invention relates to a method and an apparatus for automatic processing of at least one biological sample accommodated on a carrier, such as a slide, by applying a predetermined amount of reagents in a sequence according to a protocol, wherein at least one carrier is provided in a carrier rack assembly and wherein the apparatus further provides capability for pre-treatment prior to staining.

BACKGROUND OF THE INVENTION

This application relates to the field of sample processing systems and methods of processing biological samples. The present invention may be directed to the automated processing, treatment, or even staining of samples arranged on carriers, such as microscope slides or similar plane, rectangular sample carriers, and in some embodiments, directed to the continuous or batch processing of samples and carriers, as well as washing elements of a sampling system. Embodiments may further relate to control systems for sample processing and data acquisition, data maintenance, and data retrieval for sample processing. Applications to which the present invention may especially relate include immunohistochemistry, in-situ hybridization, fluorescent in-situ hybridization, special staining, and microarrays, as well as potentially other chemical and biological applications.

In this application, the term "staining" is used for the end product of the process, by which certain parts of the sample may be stained, i.e. have obtain a different color, either in the optic range or in another electromagnetic range, such as ultra violet, or the staining may be a detectable, preferably automatically detectable, change in properties, such as fluorescent properties, magnetic properties, electrical properties or radioactive properties. To obtain the staining, the sample normally must undergo a series of treatment steps, such as—but not limited to—washing, binding of reagents to the specific parts of the sample, activation of the reagents, etc. and each treatment step may include a plurality of individual treatments.

Sample processing in immunohistochemical (IHC) applications and in other chemical and biological analyses may require one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

In preparation for sample analysis, a biological sample may be acquired by known sample acquisition techniques and may comprise, for example, in IHC applications, tissues generally or, even, in some applications one or a plurality of isolated cells, such as in microarray samples, and may be presented on a microscope slide or a similar plane, rectangular sample carrier. Furthermore, the sample may be presented on the slide or other carrier variously and potentially in some form of preservation. As one example, a sample such as a layer or slice of skin may be preserved in formaldehyde and presented on a slide with one or more paraffin or other chemical layers overlying the sample.

Immunologic applications, for example, may require processing sequences or protocols that comprise steps such as deparaffinization, target retrieval, and staining, especially for in-situ hybridization (ISH) techniques. Previously, in some applications, these steps may have been performed manually, potentially creating a time-intensive protocol and necessitating personnel to be actively involved in the sample processing. Attempts have been made to automate sample processing to address the need for expedient sample processing and a less manually burdensome operation. However, such previous efforts may have not fully addressed the needs for an automated sample processing system. Such prior efforts to automate sample processing may be deficient in several aspects that prevent more robust automated sample processing, such as: the lack of sufficient computer control and monitoring of sample processing; the lack of information sharing for processing protocol and processing status, especially for individual samples; the lack of diagnostic capabilities; and the lack of real-time or adaptive capabilities for multiple sample batch processing.

The staining procedure is laborious and uses many different reagents. The staining protocol may include the following steps: deparaffinization, washing, antigen retrieval, endogenous biotin or enzyme blocking, incubation with immunological reagents, molecular probes, secondary visualization reagents and various chromogen reagents, washing steps and counterstaining.

Methods for mixing reagents and liquids are well known—but several aspects are important in the context of IHC and ISH instruments wherein the mixing in some processes can be cumbersome. By providing a sample processing apparatus having an automated mixer integrated therein, these types of staining processes can be performed automatically instead of requiring human interaction or manual performance of some process steps, thereby achieving a much more automated process, and the quality of the staining process may be improved as a desired degree of mixing of reagents may be provided as well as an optimal application time window for a deteriorating mixture may be reached.

An on-board mixing device for an automated biological sample processing apparatus should be able to mix multiple reagents and mixtures. Non-limiting examples include: dilution of chromogens concentrates, mixing and dilution of two, three or four component enzyme chromogen reagents, dilution of buffer concentrates, dilution of immunological reagents with dilution buffer, dilution of visualization reagents with dilution buffers, mixing several visualization reagents with dilution buffer or dilution of enzyme blocking reagents, dilution of biotin blocking reagents or mixing and dilution of counterstaining reagents.

Unfortunately, during the mixing, several problems may arise. Some problems arise due to the complex use of reagents in the staining procedure. Below a few non-limiting examples are listed in more detail:

1. The chromogen reagents (e.g. DAB, AEC, fast red etc) often comes as concentrated reagents in organic or high viscosity solutions and needs to be diluted prior to being applied to the sample. Chromogens like the Fast Red alkaline phosphatase chromogen are made ready for use by mixing and dilution of two or three reagents, which are very different in nature with regard to salt content, viscosity and density. Furthermore, the resulting mixtures are unstable over time and need to be used within a short time. Some chromogens suitable for e.g. horseradish peroxidase, like DAB and AEC, are easily oxidized when exposed to air during e.g. vigorous mixing or dilution.

2. The enzyme chromogens and counter-stain reagents like e.g. hematoxylin, are semi oxidized and can contain precipitates and solids. By further oxidation or slight change in pH, the reagents can further precipitate.

3. Antibody and enzyme containing reagents often contain stabilizing proteins and or detergents, which causes the solution to foam when being shaken or stirred. Many proteins cannot easily tolerate to be exposed to the hydrophobic air in foam. Wash buffers can contain detergents, which can foam when shaken or stirred. The foam can spread to other compartments of the instrument in an unwanted and unpredictable way. Mixing of some reagents like e.g. the HRP chromogens and peroxide reagents can result in the formation of small bubbles. These can generate foam or bubbling on the surface of the mixture.

4. Spill over/carry over must be avoided. The staining process is characterized by using many, complex and very different reagents and buffers and in many different dilution ratios and mixtures. Some of the reagents or buffers are incompatible with each other. In the event of cross contamination due to e.g. carry over, the reagents may be ruined within seconds or solids can precipitate, making the staining unsuccessful. For example, enzyme containing reagents can not be mixed with the corresponding chromogens, or high salt concentrates may not be mixed with e.g. proteins containing mixtures, or organic solvents can not be mixed with protein containing mixtures, or highly pH buffered wash buffers can not be mixed with low buffered mixtures without significantly altering the properties of the reagents. Accordingly the cleansing and washing of the mixing device need to be very efficient.

As the procedures are very complex, and the instrument uses many different protocols, one cannot predict the result of reagent carry-over or unplanned mixing of reagents. Consequently, a mixing device for an automatic biological sample processing apparatus should ideally be very efficient and be designed for a variety of reagent mixing protocols and sequences.

During staining, build-up of small fouling layers on the various surfaces will rapidly cause problems, as the typical staining protocol calls for many mixing and dilution steps. Consequently, the mixing device should have a minimum of surface area and very smooth surfaces. Furthermore, the mixing device should ideally be able to mix very different volumes of reagents in both small and large volumes ratios. In other words, the degree of dilution and mixing ratios of reagents may vary from small to high ratios. In summary, the mixing device should ideally allow: mixing of small and large volumes; mixing reagents with different viscosities and densities; mixing of immiscible or nearly immiscible reagents; no fouling of mixing rods or similar due to precipitated material; easy escape of formed gasses during mixing; prevention of foaming of e.g. detergent or protein containing reagents; low build-up of debris or fouling on the device surfaces; easy emptying and washing—regardless of volumes; and very low reagent carry-over. No present mixing system for automated biological sample processing apparatus truly fulfills the above-mentioned properties. On-the-slide mixing does not allow for very large ratios of dilution. Neither does it allow for efficient mixing of reagents with very different densities or viscosities.

Further, a defined staining protocol may include one or more defined temperatures. Important, therefore, for many IHC applications, and many sample processing sequences and protocols, generally, are temperature characteristics associated with the sample, sample carrier, and the processing environment. Traditional sample processing technology has provided temperature control through heating devices that heat an entire set of sample carriers in the sampling processing system. Other technologies, such as the sample processing system described in U.S. Pat. No. 6,183,693, may provide heating devices for individual sample carriers that are individually controlled to heat the slides. However, each of these traditional sample processing systems may lack a desired degree of temperature control or temperature tolerances.

Inadequacies in temperature control of traditional technologies may include uncontrolled cooling. Traditional systems may only provide ambient cooling when the heating devices are off. Ambient cooling is not considered active control and may not meet protocol temperature requirements or may not otherwise be optimal. Although heating and heat control may be features of such systems, controlled cooling of the samples, sample carriers, and processing environments may not always be adequately addressed. Cooling techniques such as hooded fans may be incorporated in some traditional technologies. However, these devices can lack sufficient capabilities of temperature control to meet certain protocol requirements, especially temperature tolerances for samples, sample carriers, reagents, and ambient system temperature.

Traditional systems may even lack temperature control, perhaps as related to temperature tolerances generally, as such tolerances may not be adequately maintained during ambient or other traditional cooling, or during processing sequences or events, generally. In some protocols, for example, the temperature tolerances during non-heating periods may be such that uncontrolled temperature changes may produce undesirable results during the processing sequence. Other IHC processes of the protocol may be adversely affected by uncontrolled temperature changes, the degree of temperature change, and temperature changes outside of preferred tolerances. The lack of temperature control may actually dissuade technologists from employing automated processing sequences or protocols, especially IHC sequences, that may be dependent upon a particular temperature tolerance and the amount of temperature change during a processing sequence.

Certain types of temperature control may not have even been addressed in traditional sample processing system technologies. Reagents can play a vital role in the staining sequence of many processing protocols. The quality of the reagents, therefore, may be important for adequate sample processing. Reagents, for example, can have a certain shelf life that may be limited if maintained at undesirable temperatures such as the typical ambient temperatures of traditional biological sample processing systems and the laboratories housing such systems. Traditional technologies may lack the temperature control needed to optimally preserve the reagents stored in the processing system that are often subject to inadequate or changing ambient temperatures of such systems and the laboratory environment.

Sample processing apparatuses for staining and treating samples by means of probes normally comprises a first section or station for containing one or more reagent containers, such as bottles or vials; a second section or station for mounting slides, a probe arranged to aspirate a portion of reagent from a selected reagent container and dispensing the reagent to a slide on which the sample is arranged and a drive means for moving the probe between the various sections.

Past efforts at automated sample processing for samples presented on carriers such as slides, such as U.S. Pat. No. 6,352,861 and U.S. Pat. No. 5,839,091, have not afforded the various advantages and other combinations of features as presented herein. U.S. Pat. No. 5,948,359 discloses an apparatus of the above mentioned type, wherein the first station comprises a vial holder for holding 40 or more vials in order to provide a wide range of different reagents adapted for different staining purposes, and thereby the possibility of automatically staining a large number of slides requiring different staining processes. In practice it is very important that the apparatus facilitates that many different staining processes can be performed at the same time in the apparatus, because this avoids the necessity of batching samples requiring the same procedure or other treatment with reagents, and processing each batch individually.

Even though automated biological staining apparatuses are known in the prior-art, these conventional apparatuses do not provide for sample pre-treatment. Biological samples, such as tissue samples, must be prepared before the staining can be performed. The tissue slides are subjected to a pre-treatment process depending upon the type of staining process that is to be performed on the tissue. This pre-treatment could include deparaffinization or target retrieval. The preparation of the tissues on the slides is often carried out manually in the laboratory before they are loaded into the automatic staining instrument. This pre-treatment includes immersing the slide in a buffer or other types of processing liquid for a predetermined amount of time and temperature. Unfortunately, however, this manual preparation is cumbersome and the pre-treatment may be insufficient, since it is critical that the amount of time and the temperature of the liquid must be observed very precisely in order to achieve the correct pre-treatment result.

In the U.S. Pat. No. 5,839,091, an automated staining apparatus is disclosed wherein a plurality of biological samples accommodated on microscope slides may be processed. However this instrument does not provide a processing tank for pre-treatment of the slides.

Some staining processes involve the use of hazardous materials, such as toxic materials. These materials may be collected in special containers in order to ensure safe handling of the waste material. However, this does not sufficiently protect the laboratory environment in which the apparatus is placed from being contaminated with toxic material. Moreover, in some staining processes or other treatments in the apparatus, heat is applied. This increases the risk of vaporizing reagents which then may escape to the outside of the apparatus.

In the apparatuses known in the art, a protective hood or similar plastic cover is put over the staining apparatus in order to shield off the biological samples during the staining. In this known technique, one risk is the drying out of slides and lack of control of airspeed and temperature.

On this background, it is an object of the invention to provide an automatic pre-treatment of the biological samples on slides or other similar carriers or substrates, in the automatic staining apparatus so that the entire processing of the biological samples may be performed in a single automatic apparatus.

One of the various aspects that may be significant to users of automated process systems is that of allowing changes to the processing while it is ongoing. In this regard, it has often been considered that operators have to allow existing sequences to finish before inserting or changing the aggregate in some manner. In addition, operators often have needed particular knowledge and skills in order to assure the integrity of the process or instrument or result. The present invention seeks to reduce such effects to some degree and seeks to provide a system that may be considered more user, operator, supplier, or manufacturer friendly and may be adaptable to real-world conditions and events.

SUMMARY OF THE INVENTION

To overcome the above-mentioned problems, disclosed herein is an automated sample processing system comprising a plurality of drawers, a plurality of sample carrier retainment assemblies each removably configured with one of the drawers, a reagent section having a plurality of reagents in bottles or vials, and an adaptive sample processing control system, preferably implemented in the software or firmware of one or more computers and/or the sample processing system itself, to which the drawers and the sample carrier retainment assemblies are responsive. The sample carrier retainment assemblies may comprise slide retainment assemblies and may be removably configured with the drawers to provide sample processing with the drawers of the system. The adaptive sample processing control system may automate the sample processing system such that one or more batches of samples may be processed according to one or more protocols, potentially indicated by information on the slides, that may be automatically identified by the adaptive sample processing control system. Sample processing may comprise one or more sampling protocols and steps, such as deparaffinization, target retrieval, and staining.

Preferably, the invention further comprises probe drive means arranged for moving a probe, wherein the probe drive means is arranged to aspirate a portion of reagent from a selected reagent container, such as a bottle or vial, of the reagent section by means of a probe and to apply reagent to a selected carrier means. The probe drive means may be a robot arm with two or three degrees of freedom, such as an articulated arm or one track or a set of perpendicular tracks along which a probe retainer of the probe drive means may be displaced, wherein the probe retainer may be moved in a direction normal to the track or tracks. The skilled person may readily design other types of probe drive means, e.g. combinations of the above described.

Preferably, the probe comprises a continuous probe tubing extending through a rigid probe member and providing fluid communication from a dispensing end of the probe member to a pneumatic pressure regulation device wherein the rigid probe member is adapted for cooperation with the closure of the reagent container. This structure enables a fast operation with a very little carry-over as the probe is easy to clean since there are no assembled parts along the inner side of the probe. Further, in order to support a fast operation, a plurality of probes such as two, three or four probes may be provided in order to allow for dispensing different reagent without washing the probe between each dispensing. Preferably, the rigid probe member may be arranged to cooperate with at least one reagent container in such manner that the probe may penetrate an opening covered by a cap comprising a septum, aspirate reagent, and withdraw from the container, and wherein the septum may be adapted to regenerate as an almost tight closure of the reagent container, i.e. become substantially closed again. This configuration is advantageous as the probe can easily get access to the content in the reagent container. No time is wasted on removing caps and, yet, the reagents will be protected against evaporation and contaminations thanks to the ability of the septum to regenerate as an almost tight closure.

In a preferred embodiment, the septum comprises a plurality of sectors, e.g. four sectors, such as flaps, which are free to flex upwards or downwards, thereby allowing the aspirating end of the probe to penetrate the closure and the closure to almost regain its closed form after retraction of the probe. Preferably, the sectors or flaps are originally connected by lines of weakness, wherein the lines of weakness break the first time a probe is inserted into the reagent container, and, afterwards, are free to flex upwards or downwards, thereby allowing the aspirating end of the probe to penetrate the closure and the closure to almost regain its closed form after retraction of the probe. Preferably, the dispensing end of the probe is a cone in order to facilitate the penetration through the septum in the closure of the reagent container.

Preferably, the pneumatic pressure regulation device may include a vacuum source with which the tubing may communicate via a valve device. Preferably said valve device is operable to provide a predetermined pressure in the tubing in order to aspirate or dispense a predetermined amount of reagent at the dispensing end of the tubing. By controlling the pressure inside the tubing, the aspiration and dispensing of fluids may be accurately controlled. By using pneumatic means for operating the probe tubing, the available reagent in the reagent containers as well as the available volume in the probe tubing may be fully exploited as reagent may be withdrawn from the reagent containers by applying vacuum to the tubing.

In a preferred embodiment, an electrically conducting member of the reagent dispensing device is connected to an electronic circuit adapted for capacitive level sensing (having ability to detect the reagent level by sensing an electrical capacity, and adapted to forward information about the detected level to the computer system). Further, the computer system may be adapted to issue an order for a new delivery of the reagent if the level is below a predetermined limit.

The staining apparatus may comprise a washing station for cleaning the reagent-dispensing device. The valve device may further be adapted to provide a connection to a fluid source providing a wash solution or cleaning fluid for washing and or rinsing the probe tubing. Preferably, the washing station comprises a receptacle (wash sump) able to accommodate a substantial portion of the dispensing end of the probe, and an outlet to waste, and the outlet to the waste may be located a distance above the bottom of the receptacle so that the wash fluid ejected from the dispensing end of the probe will wash the outer surface of the dispensing end of the probe before the wash fluid is drained to waste. Accordingly the probe can be washed in a fast and effective manner inside as well as outside in a single process. After the wash, the probe may be dried by air supplied to the tubing through the valve device. The washing fluid may be selectable from a plurality of fluids according to the tube cleaning requirements.

In some embodiments, protocol information may be provided by the adaptive sample processing control system. The sample processing system may process one or more slides, or one or more batches of slides, concurrently, sequentially, or in any other temporal fashion, potentially in accordance with protocol information previously provided for a sample by a user or other decision maker. This information can then be made available for use by the adaptive sample processing control system. Sample batches or individual slides may even be inserted or removed during processing protocol steps by the control and monitoring accomplished by the adaptive sample processing control system.

Preferred embodiments of automated sample processing systems in accordance with the present invention comprise a carrier rack assembly capable of maintaining each sample carrier and its respective holder in either a vertical orientation for pre-treatment or in a horizontal orientation for administration of a staining protocol; a processing tank and an elevator for immersing the carrier, when in a vertical position, into one or more pre-treatment solutions within the processing tank and for removing the carrier from the processing tank for subsequent administration of the staining protocol, the staining protocol carried out with the carrier in a horizontal position. The pivoting of carriers from horizontal to vertical and from vertical to horizontal ensures an appropriate orientation of the carriers for both the pre-treatment and the staining processes. Thus, by the present invention, the preparation of the biological samples on the carriers is integrated in the automatic staining apparatus, so that a biological sample once it is accommodated on a carrier can be loaded into a staining apparatus wherein both the pre-treatment and the staining protocols may be performed automatically in the apparatus.

Preferably, said processing tank is provided with a heating member for heating the processing liquid contained in the tank, and the heating member may advantageously be capable of heating the tank content to an elevated temperature of at least 60, more preferably at least 95° C., and even more preferably at least 115° C. Hereby, the temperature of the fluid in the tank may be heated up to 120° C. or even as high as 150° C. and kept at this temperature for between 10 to 20 minutes without any sign of boiling. In an embodiment, the heating member is adapted to heat the fluid to a temperature of 95° C. for 40 minutes or more for performing a target retrieval process.

In a particularly preferred embodiment of the invention, the carrier rack assembly is provided in a drawer assembly, wherein the rack may be retracted from the apparatus for loading and unloading of carriers. The drawer assembly cooperates with a processing tank in the drawer receiving means of the apparatus, said processing tank being capable of simultaneous processing of a plurality of carriers accommodated in a plurality of carrier holders in the carrier rack assembly. The drawer assembly provides the apparatus with a great flexibility in use, as carriers may be loaded or unloaded from one drawer while the carriers in the other drawers may be processed independent thereof. Furthermore, the use of drawers makes it easy to operate the automatic staining apparatus, as the drawers may be lockable through programming to prevent access during certain stages of automatic operation. The processing tanks for each of the drawers may preferably be connected to common supply and waste tanks which advantageously may be arranged outside the apparatus.

Preferred embodiments of the invention may comprise a temperature regulation system or element, such as a temperature regulation device, that may be responsive to a sample processing control system. The temperature regulation device in some embodiments may actively regulate temperature, perhaps even corresponding to at least one protocol tolerance. In some embodiments, it may comprise an adaptive sample processing control system. The invention may actively regulate temperature, including actively reducing temperature, and may adaptively control temperature, again including reducing temperature.

Moreover, embodiments of the invention addressing temperature control may comprise: sample carrier temperature regulation systems; sample carrier temperature regulation systems configurable with one or a plurality of sample carrier supports; and corresponding methods of sample carrier temperature regulation. Embodiments may also include: reagent temperature regulation systems; reagent temperature controls; conductive reagent temperature regulation systems; and corresponding methods of reagent temperature regulation.

In some embodiments of the present invention, temperatures of the sample, sample carrier, or ambient system temperature, or combinations thereof, can be changed in a controlled fashion to achieve ramping temperature increases and decreases (and thus considered as having a temperature ramp up element or a temperature ramp down element, respectively), can have preferred tolerances, can minimize changes of temperature during processing, can maintain reagent quality through temperature control of the reagents, can provide for adaptive heating or cooling, and can control temperatures below or above ambient system or even the ambient lab environment temperature.

A preferred embodiment of the present invention comprises an apparatus as previously described wherein a robotic element, perhaps with a robotic head, is provided with an optical sensor, or perhaps a 2-D optical sensor means for detecting two-dimensional image data of a relevant property and with the capability of feeding the captured image data to the control means.

The invention also provides a method of identifying at least one property in an automatic staining apparatus perhaps including at least one slide array and a reagent array and a robotic element or perhaps robotic means for performing staining of the slides also using reagents; said method including, in one embodiment, the steps of providing optical sensor means on the robotic head of the robotic means, moving the optical sensor means on said robotic head to a predetermined position, recording relevant image data at said position, and feeding said image data to a control system for manipulating the staining process according to said image data.

Furthermore, the invention concerns a method of staining tissue samples in an automatic staining apparatus perhaps including, at least, one slide array and a reagent array, a robotic element or perhaps robotic means for performing staining of the slides also using reagents according to tissue sample specific staining protocols; said method including in one embodiment the steps of: providing optical sensor means on the robotic head of the robotic means, moving the optical sensor means on said robotic head to a predetermined position, recording relevant image data at said position by said optical sensor means; feeding said image data to a control system for manipulating the staining process according to said image data; and staining a tissue sample also using reagent from a reagent container.

The optical sensor or optical sensor means may be used to automatically identify the slides and the reagent containers present in the apparatus, just as the optical sensor or optical sensor means may be used for checking if a slide is misplaced at or absent from a certain slide position, where a tissue is located on a slide, the condition of the tissue either before or after processing, etc. The software controlling the apparatus may be adapted to include automated identifications of various properties and conditions of the apparatus, including slide and reagent information.

In one embodiment of the invention, the reagent section accommodates a plurality of reagent containers stationary arranged in a plurality of rows. Similarly, the tissue samples are accommodated on slides that are stationary arranged in a plurality of rows in at least one staining section or slide section during the staining process. The layout of these sections is such that it presents a substantially planar platform work area for the robotic head, which is moveable in the X and Y-axis. In a particularly preferred embodiment, a row of slides and/or reagents, such as those housed in a single drawer, can be removed and be replaced without interfering with the staining process. In another preferred embodiment, the apparatus comprises at least two staining sections separated by a reagent section, that is, the sections may be arranged so that at least some of the tissue samples are closer to at least some of the reagent containers. Hereby, the movements required by the robotic head in order to reach all the slides may be significantly limited and the capacity of the staining apparatus can hereby be increased, just as a reduction in the time for running the staining protocols or other advantages may be achieved. It is further realized that these shorter processing times or other advantages may also be achieved by this layout of the slide and reagent sections without a vision system, e.g. an optical sensor.

In other preferred embodiments of the invention, the optical sensor may be a camera or perhaps include a CCD element. By the term "camera", it should be understood that any image capture apparatus is intended whether or not is uses film, plates, memory, or any type of electronic media and whether or not it images light, visible electromagnetic radiation, or even non-visible electromagnetic radiation such as now well known. By recording the relevant image, relevant image data, or even recording digital image data, a computer processing of this data in the control system may be carried out in a quick manner by known image processing capabilities already available. Moreover, by using this digital technology relative complex images can be recorded with high resolution, just as a fast recording of several identifications, e.g. labels on an entire row of slides, may be achieved as the robotic head may be moved across the slide labels in a continuous movement, so stop and start time for each slide identification may be avoided. However, by the invention it is realized that other image sensors, e.g. solid state sensors, or perhaps CMOS sensors could also be used depending on the requirements for image resolution.

As indicated above, the optical sensor may be adapted to record the individual reagent containers or bottles and slides present in the apparatus. While, of course, it may image larger areas, or perhaps even the entire device, it may be configured for individual imaging either electronically, optically, or positionally. Regardless, as a result of the imaging capability, predetermined positions of the slides or reagent containers or bottles that are loaded into the automatic staining apparatus may not be required, since the apparatus may be adapted to automatically identify new slides and reagent bottles once they are loaded into the apparatus.

In an embodiment, the reagent containers and the slides may be provided with an optical identification element. For example, a reagent container may be provided with a reagent optical identification element and a slide may be provided with a slide optical identification element. These optical identification elements may contain machine readable data concerning the reagent type as well as other relevant data relating to the reagent in the bottle, and the slide identifiers may contain data concerning the tissue sample, such as identification of the patient, the staining protocol, etc. An optical identification element may include reiterated information or perhaps even redundant information. This may include information that is repeated or even partially repeated and may even include information that may or may not be in different versions which may relate to similar information.

In an embodiment of the invention, one type of optical identification element may be a two-dimensional high-resolution symbology code, e.g. of the so-called "Infoglyph™" type. The optical identification may also be more generically a two-dimensional symbology. Two-dimensional symbology may be representative of data including, but not limited to: tissue sample related data, patient identification data, staining protocol data, reagent related data, reagent type data, reagent volume related data, reagent durability related data, and the like data. An advantage of using an optical sensor capable of reading 2-D symbology is that the apparatus may be capable of reading any kind of optical identifier, as this only requires an adaptation in the software processing of the captured and, perhaps, digitized image.

In a more advanced usage of the 2-D image capturing capability, the image processing capability or image processor element may be adapted to identify the texture or outline of the tissue sample itself captured by the optical sensor and may use said image-captured tissue property as an individual identification of the tissue sample. The optical sensor may be configured to identify desired features of the tissue samples such as but not limited to the texture, outline, a visual property, or even an individual feature of a tissue sample. Of course, various different features or properties may be identified, as desirable, to detect, or perhaps identify, a property which may include any attribute, characteristic, or the like. This embodiment could make the use of slide labels obsolete, as the tissue texture itself or at least a predefined section thereof (with or without magnification) could be used as an identifier for a list of data in the control software.

In another embodiment of the invention, the optical sensor may be a camera adapted to record an image of the finalized tissue sample after said tissue sample has been subjected to a staining protocol for recording an image of the manipulated tissue sample. Hereby, a picture or digital image of the stained tissue sample may be recorded, preferably in a high resolution, for later examination or for sending this digitalize picture to a remote location for examination. Accordingly, embodiments the present invention may provide for storing an image relevant to the process of staining tissue samples. This may include images both before and after staining or some other operation, of course. Also, this feature of the invention may provide for archiving images of the about-to-be-stained or the stained tissue samples for later verification of the tissue sample analysis or the identification if this should it be required.

Preferably, embodiments of the present invention comprise a reagent mixer having a mixing cup for receiving two or more reagents and mixing means for mixing the reagents in the mixing cup, and means for dispensing the reagent mixture from the mixing cup to a selected carrier means. The system may mix component fluids, such as dyes, buffers, or other processing materials, preferably on demand and as the processing steps and protocols dictate. Fluids required during the processing steps may sometimes need to be mixed with other fluids to create a final activated fluid. However, the activity levels of these mixtures can be time sensitive and may therefore only be effective for a short period of time. The on demand mixing of fluids is advantageous in that it allows the fluids to be mixed immediately before being used.

The mixing means of the reagent mixer may advantageously be constituted by cup drive means arranged for cyclic movement of the mixing cup, e.g. shaking or rotation in a horizontal or a vertical plane, so as to mix reagents contained in the mixing cup. The mixing of the reagent may be further improved by arranging mixing elements, such as blades or edges within the cup and stationary with respect to the cup. Other known mixer types may instead be preferred, such as shaft-driven impellers or magnetically driven impellers.

The cyclic movement is preferably a rotation of the mixing cup, advantageously about a substantially vertical axis. The rotation is in a preferred embodiment an intermittent rotation in a clockwise and in an anticlockwise direction. Preferably, the rotation speed may be varied through control means acting upon a driving motor in such manner that the fluid content inside the mixing cup is agitated, but at so low speed that substantially all reagents remain in the mixer cup. Preferably, the speed may be controlled depending on the type of reagent in the mixer cup. Preferably the speed is controlled according to the processing protocol controlling the processing of the sample(s) to be processed in the apparatus. Preferably, the rotation pattern (speed and direction) is controlled by the sample processing control system, according to the sample processing protocol, thereby optimizing the quality the mixing in the mixer cup in respect to the reagents present in the mixer cup. For the sake of good order, by "sample processing protocol" is meant a sequence of processing steps defined for the actual sample treated in the sample processing apparatus.

In order to provide an efficient and fully automated cleansing of the mixing cup when changing from one reagent mixture to the next, it is advantageous that the mixing cup has inner walls extending upwardly and outwardly from a bottom part of the mixing cup, and the cup drive means is capable of rotating the mixing cup at an angular speed sufficient to fling all reagents contained therein out of the mixing cup. Preferably, the inner walls are smooth and may terminate in an upper rim at the widest inner diameter of the mixing cup, in which case the high-speed rotation, preferably about a symmetry axis of the cup, will cause the waste reagent or cleansing liquid to be flung out over this upper rim. In an alternative form of the mixer, according to embodiments of the invention, the inner walls of the cup extend upwards and inwardly above the level of the widest inner diameter, at which one or more exit openings are provided in the inner wall as outlets for the waste reagent or the cleansing liquid. The top may be open for the probe to enter the mixing cup, or it may be closed to facilitate that the cyclic movement of the mixing cup for mixing the reagents may have a vertical component. The probe may, in this case, enter the mixing cup through one of the exit openings. To collect the waste reagent or the cleansing liquid, it is preferred that the reagent mixer comprises a waste reagent collecting chamber having a sidewall part laterally surrounding the mixing cup and arranged to collect reagents flung out of the mixing cup by rotation of the cup.

Preferably, an apparatus in accordance with an embodiment of the present invention further comprises at least one staining section provided within a housing; a hood cover protecting said at least one staining section in said housing; wherein the hood cover completely encloses the staining section defining an interior space; a climate control device that provides control of the environment within said interior space; and an environmental sensor device to provide feedback signals to the climate control means. In an apparatus according to embodiments of the invention, these fumes may be exhausted from the interior space of the apparatus, just as the climate in the apparatus may be controlled. In particular, in order to avoid the volatile fumes from escaping into the surroundings, the climate control device preferably includes a pressure control device that can ensure a slight sub-pressure within the interior space. By maintaining a slight sub-pressure inside the apparatus, the fumes are kept inside in the interior space, from where the climate control system may remove the volatile fumes. These fumes may advantageously be collected in suitable storage, or otherwise be disposed of. Advantageously, the climate control device may also include humidity control within the interior space. This makes an apparatus according to an embodiment of the invention more suitable for some special sample treatment applications, just as the climate requirement inside the laboratory where the apparatus is placed may be less strict. Moreover, the climate control device may preferably also include a temperature control device that can control the ambient temperature of the air within the interior space.

The climate control device in an apparatus according to an embodiment of the invention may include an exhaustion device that can remove fumes from the interior space. These exhaustion devices are, preferably, adapted to draw air from an outlet positioned below the level in which the at least one slide is accommodated. Hereby, fumes are drawn away from the hood and the slides. This may reduce any risk of cross-contamination. Cross contamination could be a problem, as some fumes can adsorb to the biological sample, resulting in a change of properties. Especially, hydrophobic, acidic, basic, strong chaotropic or otherwise reactive or corrosive fumes can cause serious and unwanted cross contamination.

The environmental sensor device is preferably adapted to sense at least one climate parameter from the group consisting of temperature, pressure, humidity, airspeed and the presence of toxic elements in fume. These measured air characteristics are used for manipulating the inflowing air into the interior space, so that it is ensured that the biological samples are processed in a controlled ambient environment and that it is ensured that the samples do not dry out or are otherwise being deteriorated.

The environmental sensor device may comprise internal sensors located inside the interior space. Alternatively, the environmental sensor may comprise external sensors located outside the interior space, such as at or inside an air inlet/outlet manifold, in a laboratory facility accommodating the apparatus, or outside the building accommodating the laboratory.

In an embodiment of the invention, the cover is a plurality of covers arranged to cover a plurality of sections of the apparatus, such as at least one biological sample accommodated on a carrier in the at least one processing section. Hereby, different environments may be created for different samples.

In a preferred embodiment of the invention, the hood cover is provided with one or more seal elements to provide an air-tight seal between the cover and the housing. Hereby, the sub-pressure need not be present or a higher pressure inside may be provided for achieving a more precise climate control inside the apparatus.

The exchange of air between the interior space and the surroundings may be carried out via an inlet and an outlet. In an embodiment of the invention, the inlet may be provided for supplying air into the interior space including an air inlet opening in the housing, and wherein air manipulation device are provided in addition to said inlet means to adapt the inflowing air with predetermined characteristics. Hereby, the inside climate of the air in the interior space may be accurately controlled.

Another preferred embodiment of the present invention may comprise a method of sample processing, comprising the steps of: accessing at least one of a plurality of samples or sample drawers, providing at least one sample carrier or perhaps a sample carrier retainment assembly configured with at least one sample, configuring at least one of the drawers with the at least one sample carrier, and adaptively processing the sample. The step of processing or perhaps even adaptive processing may be applied to automate the processing of samples and may allow for either or both continuous or batch processing of samples or slides. It may also afford multiple independent sample or slide processing and, in some embodiments, slide processing to process each slide independently.

Other preferred embodiments of the invention may further comprise a method of automated sample processing, comprising the steps of acquiring protocol information, transmitting the protocol information to at least one sample processing system, adaptively processing samples, and acquiring sample processing information from the step of adaptively processing. Furthermore, embodiments may provide: maintaining the protocol information, maintaining the sample processing information, information sharing of protocol information, and sample processing information. These and other method steps may be provided for individual samples or multiple batch processing, sample diagnostic features, and real-time or adaptive capabilities for multiple batch processing.

Many other embodiments of the invention are disclosed in this application, some of which may comprise independently, dependently, or in combination, processing tanks, environmental control systems, sample carrier retention devices, probe arms, washing stations, mixing stations, sample carrier manipulation devices and means, sample processing probes, waste systems, probe sanitizing systems, processing material units, and various other systems, devices, apparatus, and assemblies.

Many aspects of invention are applicable to immunohistochemistry (IHC) techniques, as well as in-situ hybridization (ISH) and fluorescent in-situ hybridization (FISH) special staining of samples, and micro-arrays, especially techniques incorporating target retrieval or the staining of samples. Furthermore, embodiments are directed to processing sequences addressing issues of processing control, component cleaning, and waste.

An automated sample processing system according to the various embodiment of the present invention may greatly improve operation of automated sample processing from several perspectives. It may act to accept changes to the system while operating and may automatically adapt to a change in the aggregate events originally scheduled. It also may provide a better approach to just how such scheduling may occur as well as providing a user opportunities to undo a change, such as when its effect is undesirable. The system may also provide for automatic suggestions to permit an operator to more optimally enhance the schedules on which events occur.

The techniques and systems of sample processing are addressed, according to the preferred embodiments the present invention, in a fashion that may provide the processing of one or more samples or of a plurality of groups of one or more samples in sequential or non-sequential fashion. Processing of samples may be determined by the protocol to be followed for each sample or a protocol for multiple samples. Aspects of the present invention may be especially applicable to sample processing having one or a plurality of processing steps to be performed on one, a portion, or an entirety of samples, such protocols identified in some instances by individual carriers presenting the samples or by the individual samples themselves. The foregoing summary does not purport to define the invention. The invention is defined by the claims.

BRIEF DESCRIPTION OF THE DRAWINGS

The invention is described with reference to a preferred embodiment with reference to the drawings, in which:

FIG. 5 is a description of representative deparaffinization steps of an embodiment of the invention;

FIGS. 35 A-C are additional views of embodiments of temperature control aspects of one embodiment of the invention;

FIG. 39 is a depiction of a networked embodiment connecting one stainer with one manager and one label printer;

DETAILED DESCRIPTION

The present invention relates to an improved method and apparatus for pre-treatment of biological samples. The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. The variously described examples and preferred embodiments should not be construed to limit the present invention to only the explicitly described systems, techniques, and applications. This description may further be understood to incorporate the various systems, techniques, and applications, both singularly and in various combinations consistent with the various inventive features and embodiments of the present invention. Thus, the present invention is not intended to be limited to the embodiments shown but is to be accorded the widest scope consistent with the principles and features described herein. To more particularly appreciate the features and advantages of the method and apparatus of the present invention, the reader is referred to the appended FIGS. 1-42 in conjunction with the following discussion.

Figure 1:
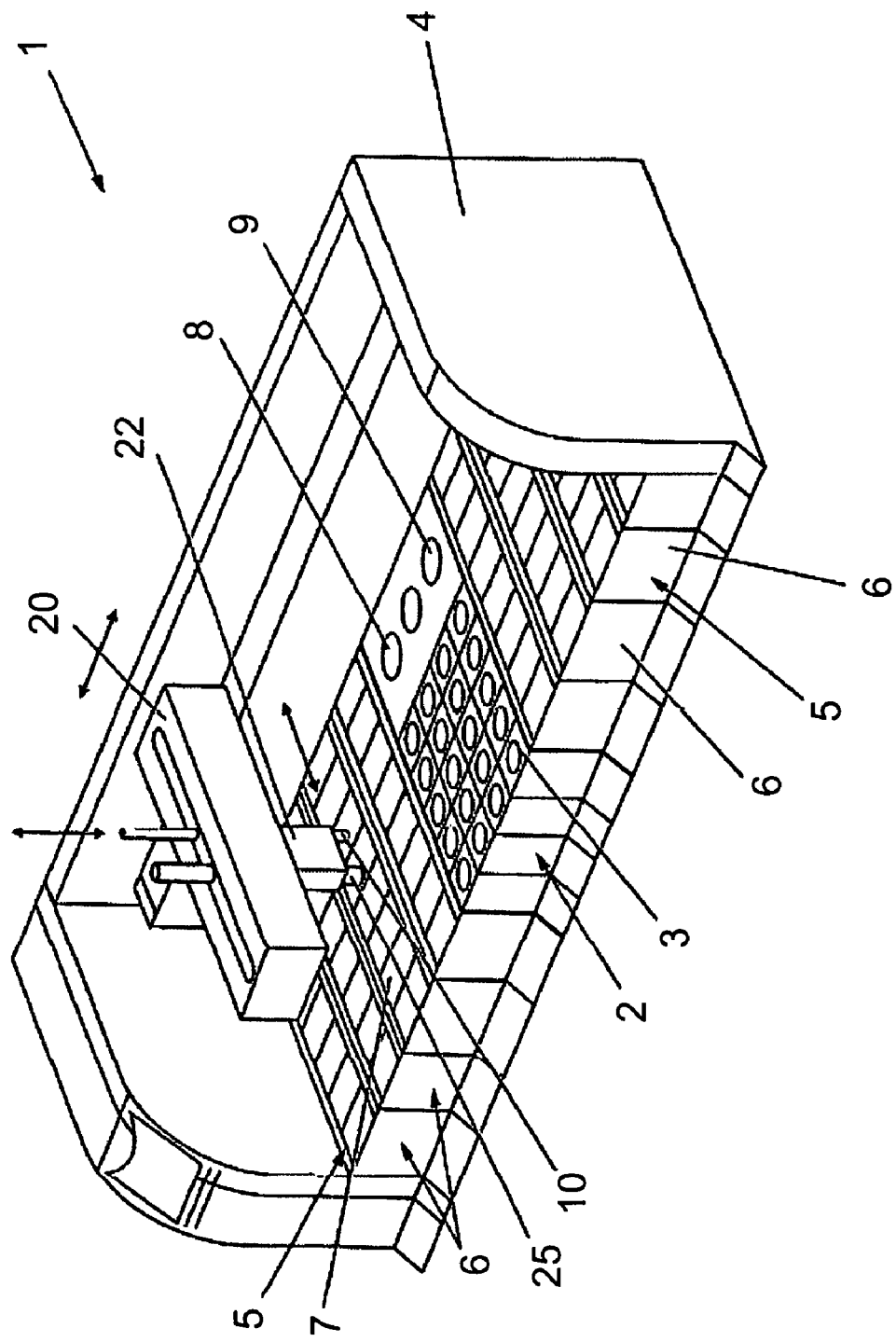
FIG. 1 is a schematic perspective view of a staining apparatus according to a preferred embodiment of the invention.
Figure 2:
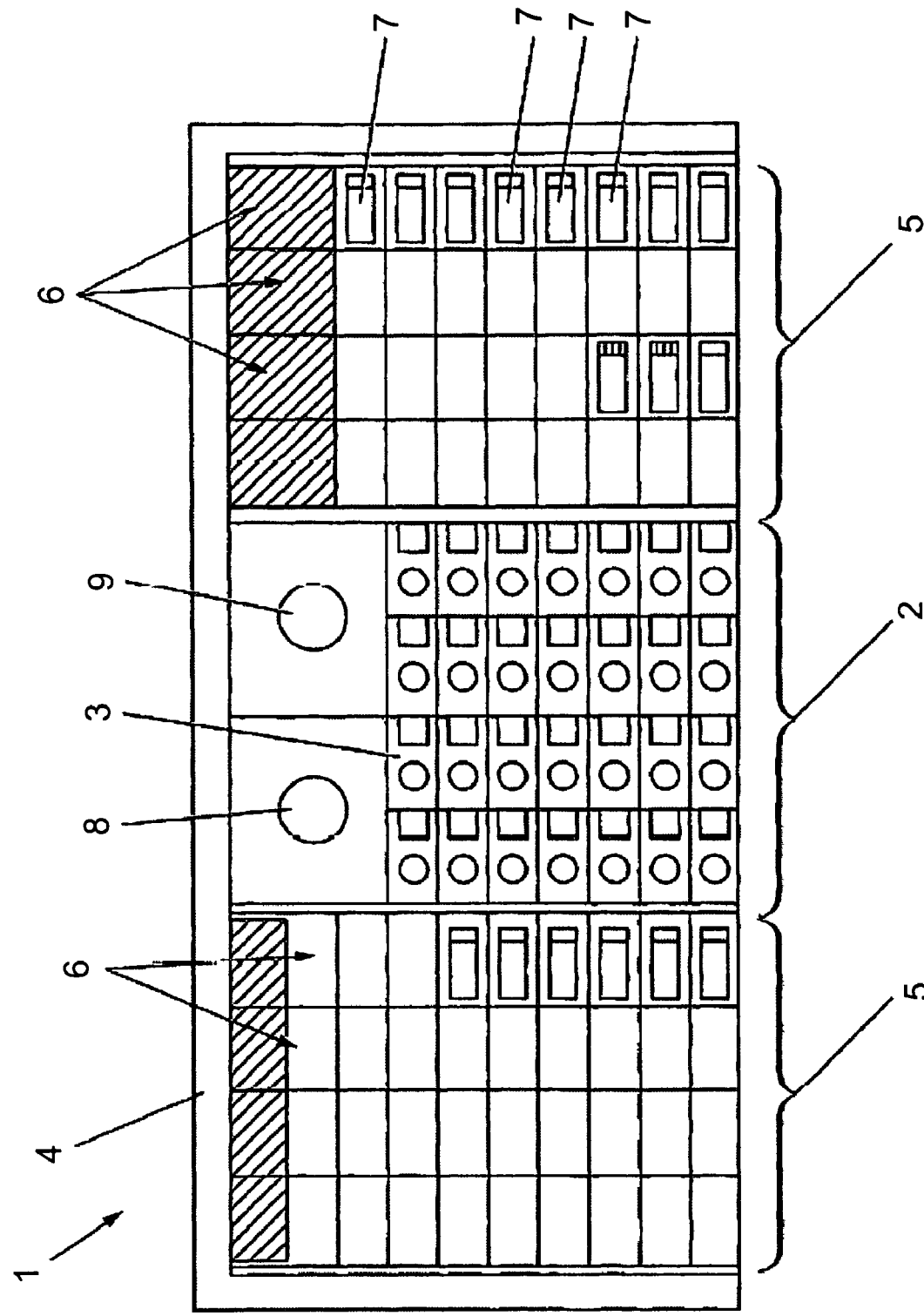
FIG. 2 is a plan view of the work area in the staining apparatus shown in FIG. 1.

A preferred embodiment of a staining apparatus 1 according to the invention is shown in FIGS. 1 aid 2. The staining apparatus 1 comprises a frame 4 surrounding a reagent station 2 comprising an array of reagent bottle compartments wherein each compartment a reagent container 3, such as a bottle or vial, is placed, and a first and second slide sections 5 wherein a number of separate rack assemblies 6 are placed, and where each rack assembly 6 accommodates a number of sample carriers 7, such as, preferably, microscope slides mounted side by side in the rack assembly 6. In the embodiment shown, each rack may hold up to 8 slides, but the rack may be designed to hold any suitable number of slides. With eight racks arranged side by side, the shown embodiments may hold up to 64 slides 7 each having a sample, e.g. a tissue mounted on the upper side of the slide, so that reagent may be applied from above to the sample on each slide.

A robot arm 20 for moving a probe 10 in X and Y (as well as Z) direction as indicated by the arrows X and Y is arranged above the frame 4 of the staining apparatus. The robot arm 20 may therefore position the probe 10 above all reagent containers 3 as well as above all the sample carriers 7, and may further operate the probe 10 to aspirate portions of reagent contained in any of the bottles 3, to transfer the portion of reagent and apply it to any of the carriers 7 in order to provide a selected staining or treatment of the sample on each carrier or slide 7. By use of suitable control means e.g. a computer (not shown) having the appropriate software and input data for the purpose, this staining apparatus 1 is able to automatically staining or treating samples requiring different staining or treatment reagents and processes.

Figure 7A:
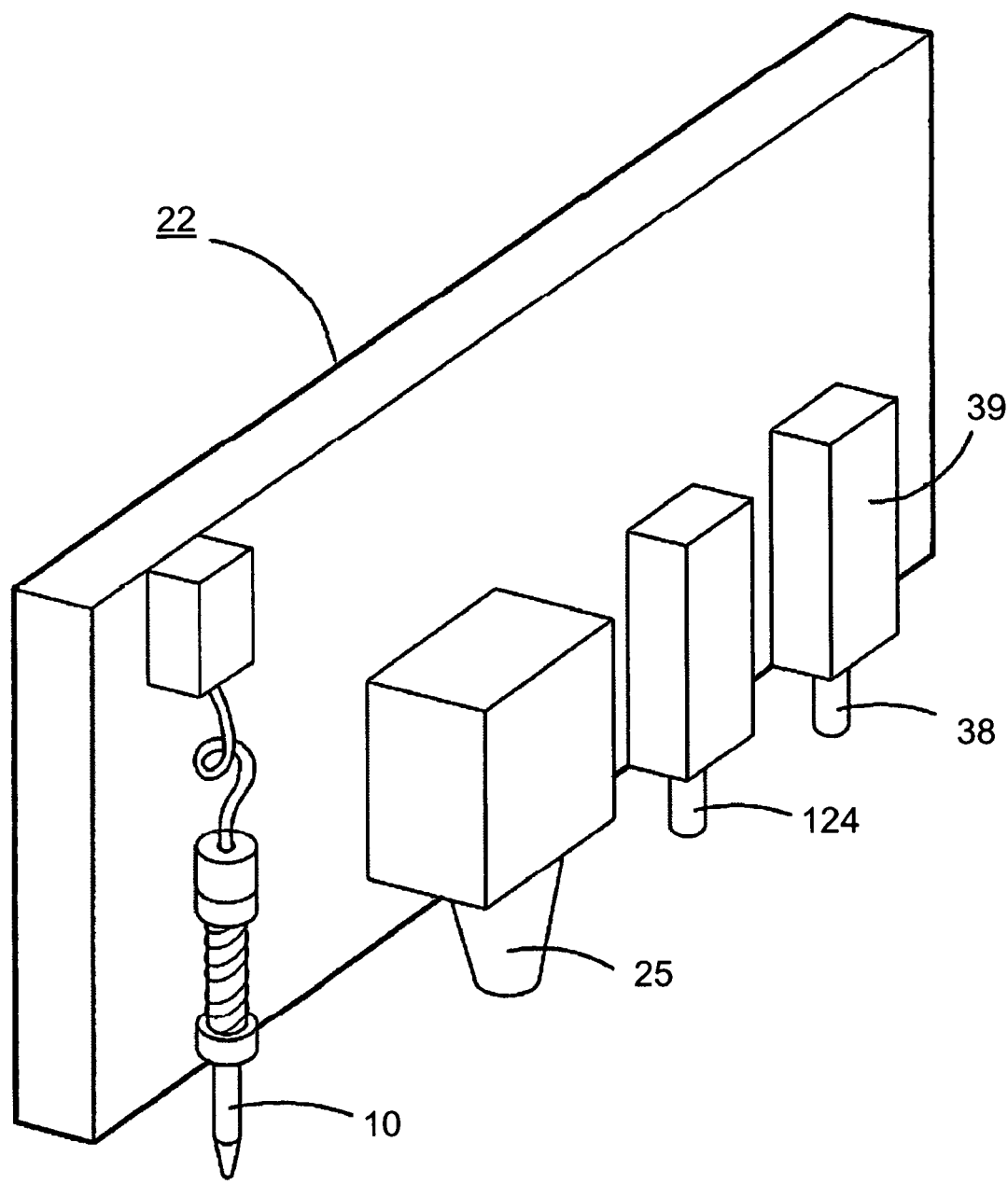
FIG. 7A shows a schematic view, in accordance with an embodiment of the invention, of a robotic head with a probe mounted thereon.

As shown in FIG. 1 and, in more detail in FIG. 7A, the probe 10 is accommodated in a robotic head 22 and is manipulated by the robot arm 20. The probe 10 is raised to an upper position (in a Z direction) where it is clear of the reagent containers 3 underneath the probe 10, but the robot comprises means in the robotic head 22 for lowering the probe 10 in order to dip the probe tip into the content of a selected reagent container 3 and to aspirate a selected amount of reagent for the selected staining or treatment process. The robotic head 22 is also provided with an optical sensor 25 such as, preferably, a CCD camera pointing downwards. The camera is utilized to determine status information of the slides and the reagent bottles and other features of the apparatus in the work area, for example reading a code provided on a reagent container to determine the reagent type and the reagent location within the system. The camera may also determine status of the tissue sample slides, for example the location of a particular slide, informational indicia, such as a code, that indicate information about the tissue sample presented on the slide or the processing protocol to be performed. The robot comprises means (which may be of well known kind, such as, e.g., a rack and pinion or a hydraulic piston) in the robotic head 22 for lowering the probe 10 in order to insert the probe tip into the content of a selected reagent container 3 and to aspirate a selected amount of reagent for the selected staining or treatment process. As schematically illustrated in FIG. 7A, the robotic head 22 may also be provided with an air nozzle 124 for blowing air onto the slide in order dry the slide or to blow away liquid. The robotic head 22 may also include a variety of other components, including, but not limited to a push tool 38, for actuating slide rotation, that may be connected to an air cylinder 39.

Figure 3:
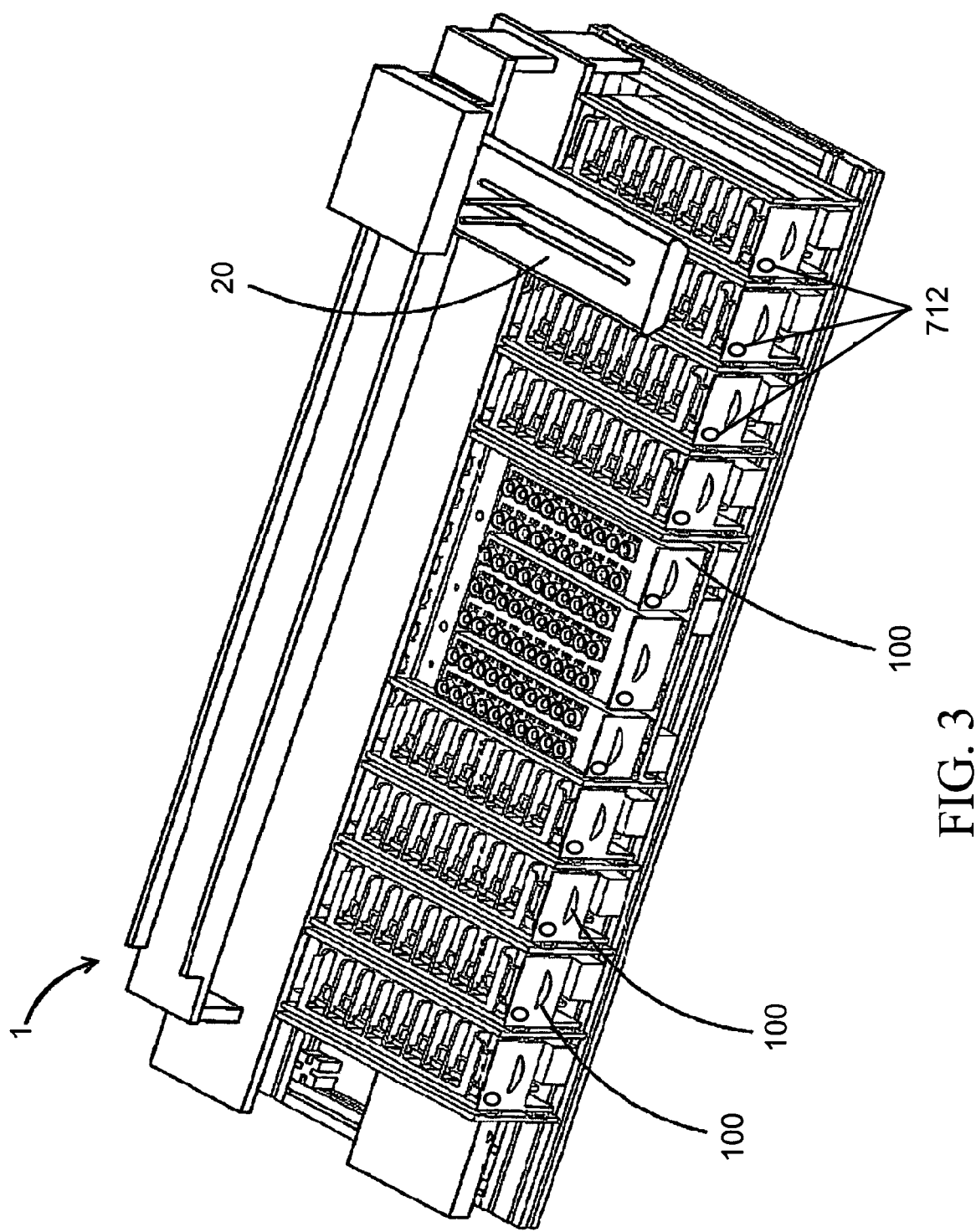
FIG. 3 is a perspective view of the work area in the staining apparatus shown in FIG. 1 showing a collection of samples with a collection of reagents according to the invention.

As illustrated in FIG. 3, the sample processing system may comprise a plurality of drawers 100 used for the handling and processing of samples and sample carriers. Each drawer may be configured to accommodate a slide rack assembly 6 or other sample carrier retainer assemblies, such as slide retainer assemblies, modules, or magazines.

Indicator elements 712 may be provided upon or within the drawers (FIG. 3) to indicate a status and accessibility of the drawers and the carriers or materials within each drawer for an operator of the system. In one embodiment, visual indicators, such as light emitting diodes in preferred embodiments, may be used to indicate if a drawer is available, and perhaps unlocked, during operation of the sample processing system, and may indicate conditions such as a locked or open condition of a corresponding drawer, carrier capacity status of the drawer or of a carrier retainment assembly within the drawer, and chemical inventory status of the sample processing system, such as reagent loading status or capacity. A warning indication may be given by these or other indicator elements, as well as other indicative signals. One or a plurality of sensors may be utilized to determine the status of the drawer as indicated by the indicator elements 712 and to further provide processing status as further described below. Thus the system may provide at least one substance in a lockable reagent retainment assembly.

Figure 24:
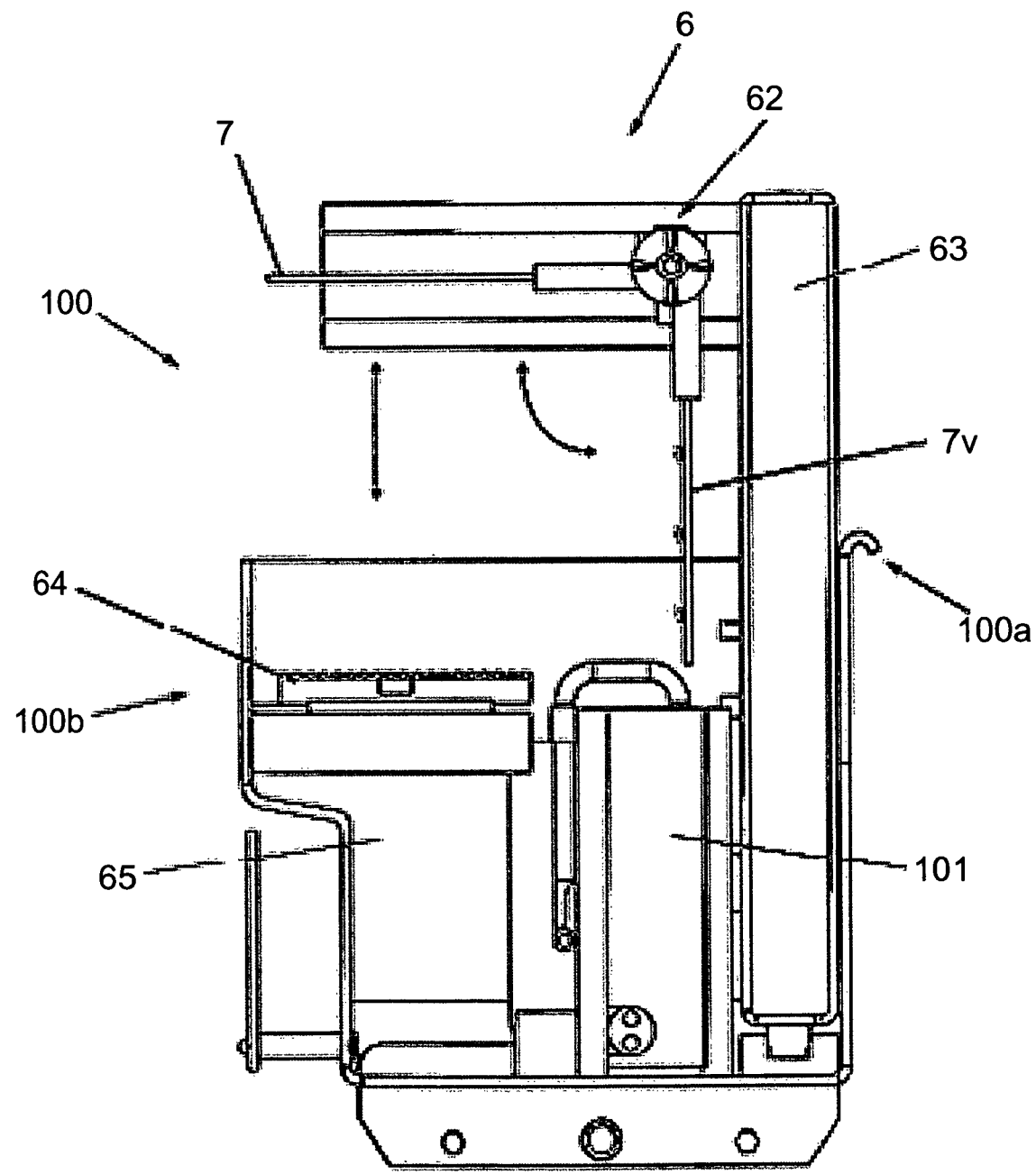
FIG. 24 is a schematic front view of a drawer assembly including a slide rack assembly and a processing tank in an apparatus according to the invention.
Figure 27:
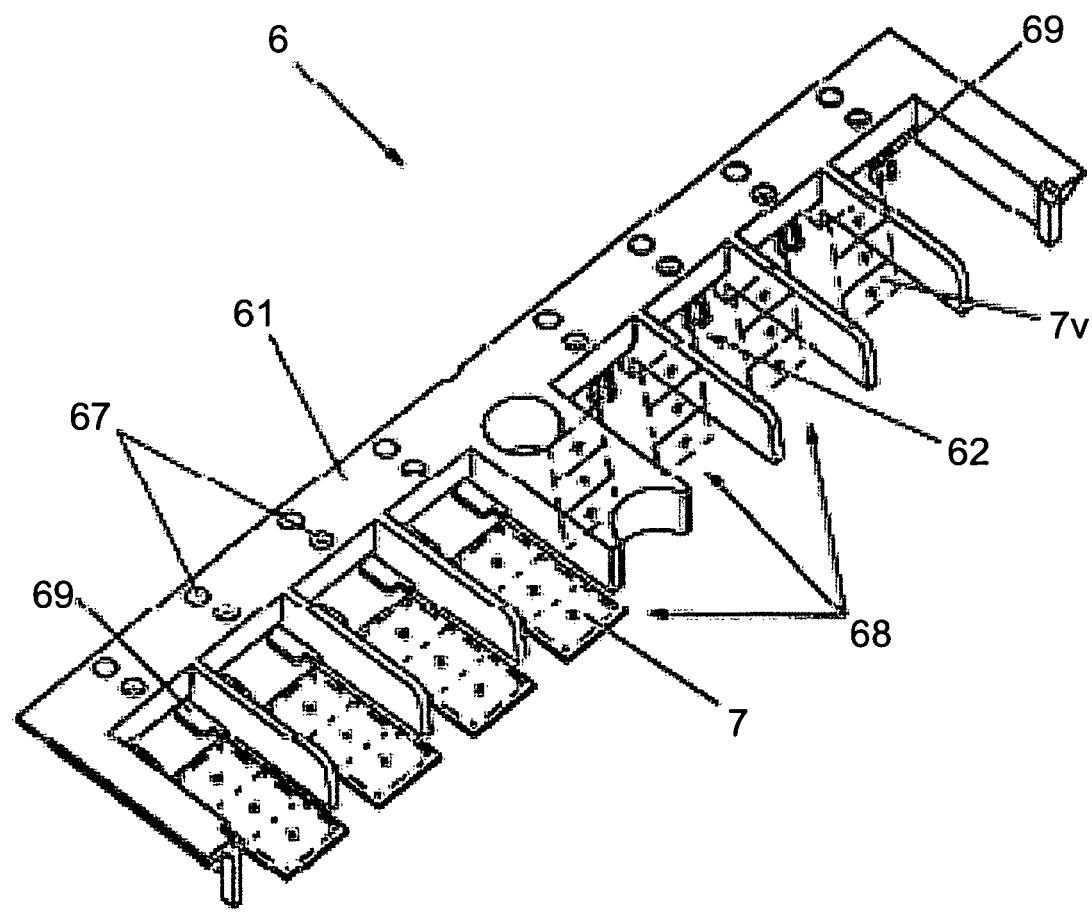
FIG. 27 is a perspective top view of a slide rack according to a preferred embodiment of the invention.

In preferred embodiments, sample carriers 7, such as slides are configurable in both vertical and horizontal positions as required for the pre-treatment and staining process, as shown in FIGS. 24 and 27. Other components in these figures will be described in detail susequently. The ability to provide vertically-oriented sample carriers 7v (FIGS. 24 and 27) in addition to horizontal sample carriers 7 allows for the automation of the pre-treatment and staining of slides in various manners, including pre-treatment and staining as accepted in conventional manual laboratory methods. The slides 7 are initially loaded into the carrier retention assemblies, such as slide racks, and drawers in the horizontal position. The slides may be horizontally supported by adjustable slide supports (shown in FIG. 28). If pre-treatment is required, such as deparaffinization, the system rotates the slide into the vertical position and lowers these samples into a processing tank 101, further described below, filled with the required fluids. In some embodiments, the slide rack 6 is lowered to affect lowering of the slides (see FIG. 24 and FIG. 28). To perform the staining process on the slides, as described below, the system rotates the slide to the horizontal position and a probe 10 applies fluid to the sample. Each slide can be rotated independently allowing for the independent processing of different samples with different requirements.

Figure 4:
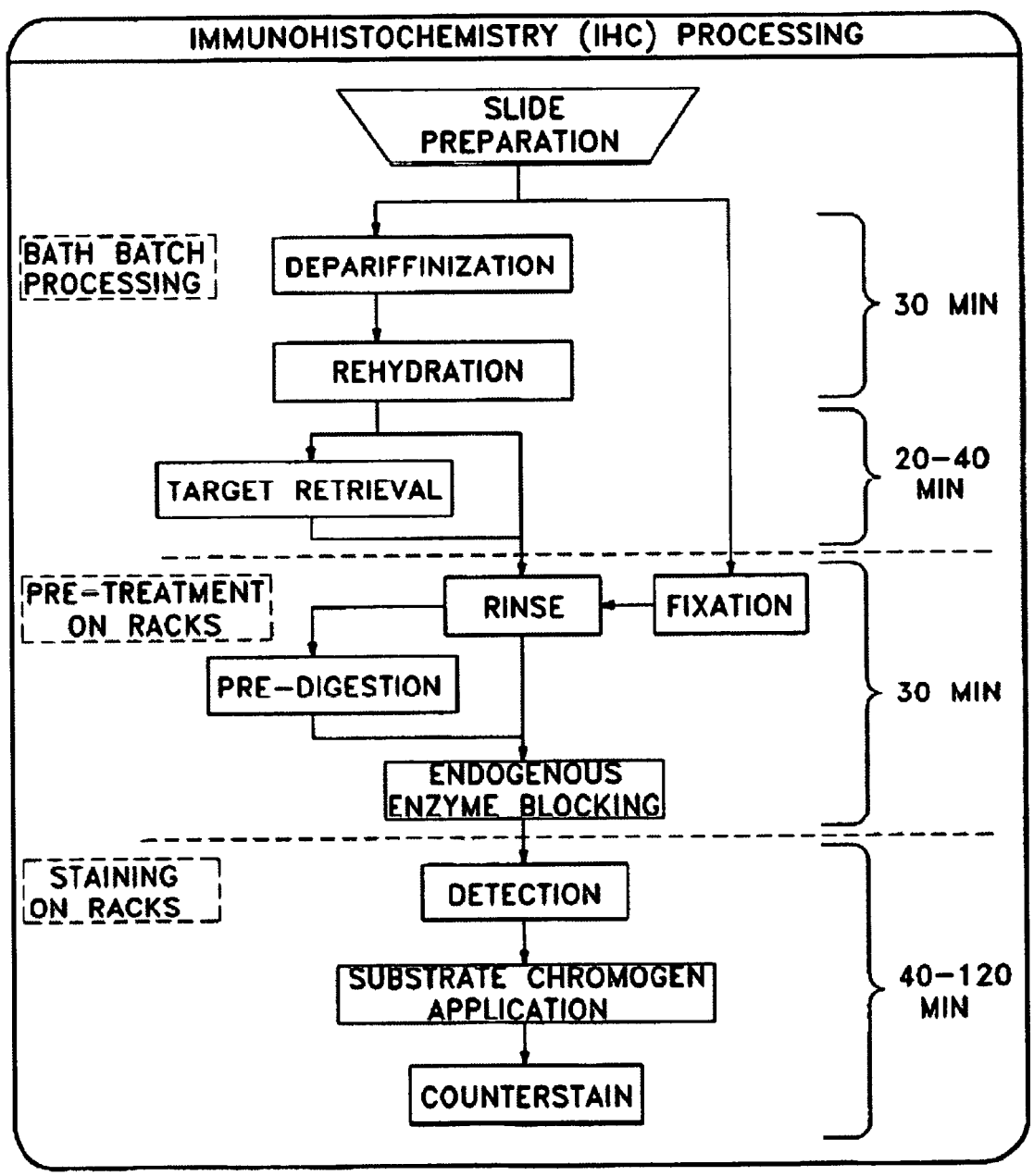
FIG. 4 is a flow chart of some representative process steps of an embodiment of the invention.

The sample processing system may automate processing steps of samples such as histological tissue sections or cell preparations presented on slides by pre-treatment processing, such as deparaffinization. The system provides onboard pre-treatment of the slides. The processing of samples may be accomplished according to some preferred embodiments as shown in FIG. 4 and FIG. 5 consistent with features of the present invention. Variants of these protocols and processing steps, or other processing steps, may be accomplished consistent with the present invention.

Examples of two types of pre-treatment that are usually performed are—but not limited to—deparaffinization and target retrieval. In some embodiments, these processes must be performed with the slides in a vertical orientation, immersed in processing tanks of various fluids. Deparaffinization involves immersing the slides sequentially in a series of fluids for short periods of time (potentially for about 5 or 10 minutes). The process is intended to first remove from the sample the paraffin in which it was mounted or otherwise presented, remove the paraffin solvent, and then slowly rehydrate the sample. Target retrieval, and in some embodiments epitope unmasking, involves immersing the slides in a processing tank of heated buffer, and in some embodiments, immersing for about 20 minutes, and possibly up to 60 minutes, and then allowing the slides to cool for about 20 minutes. Temperature in preferred embodiments is maintained at about 95° C. In target retrieval, a marker or other identifier is used to mark a sample portion of interest, such as a cell or structure thereof.

Figure 25:
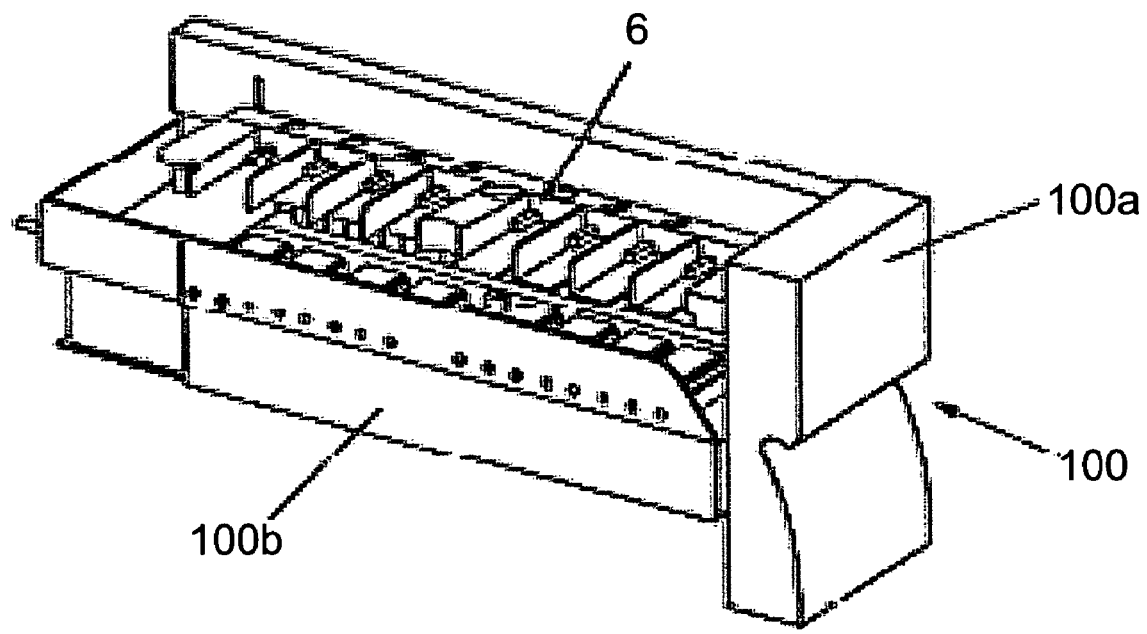
FIG. 25 is a perspective view of a drawer assembly in a closed position.
Figure 26:
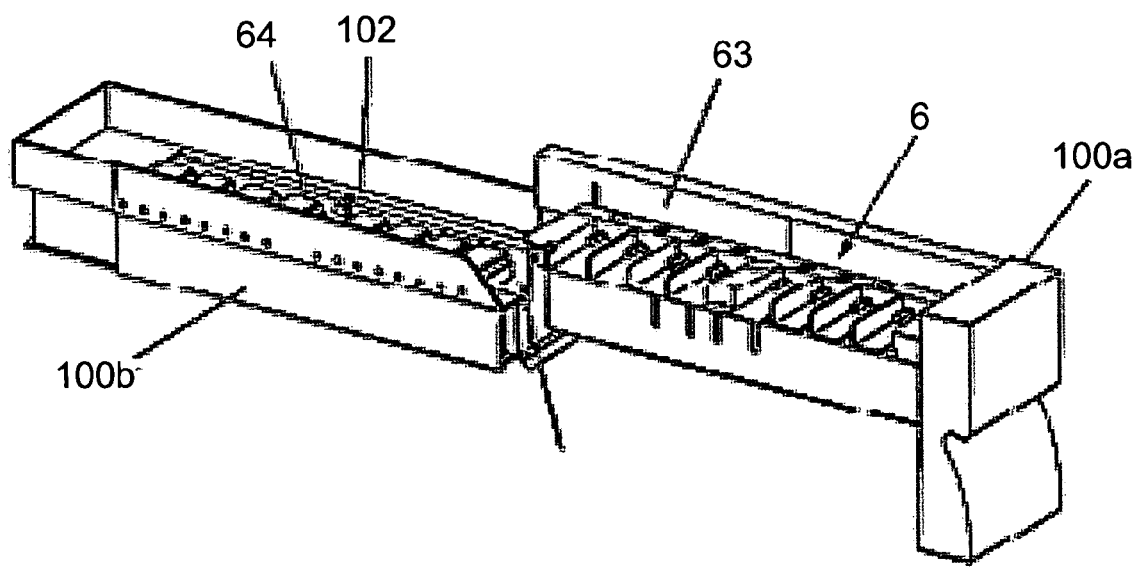
FIG. 26 is the drawer assembly of FIG. 25 in an open position.
Figure 28:
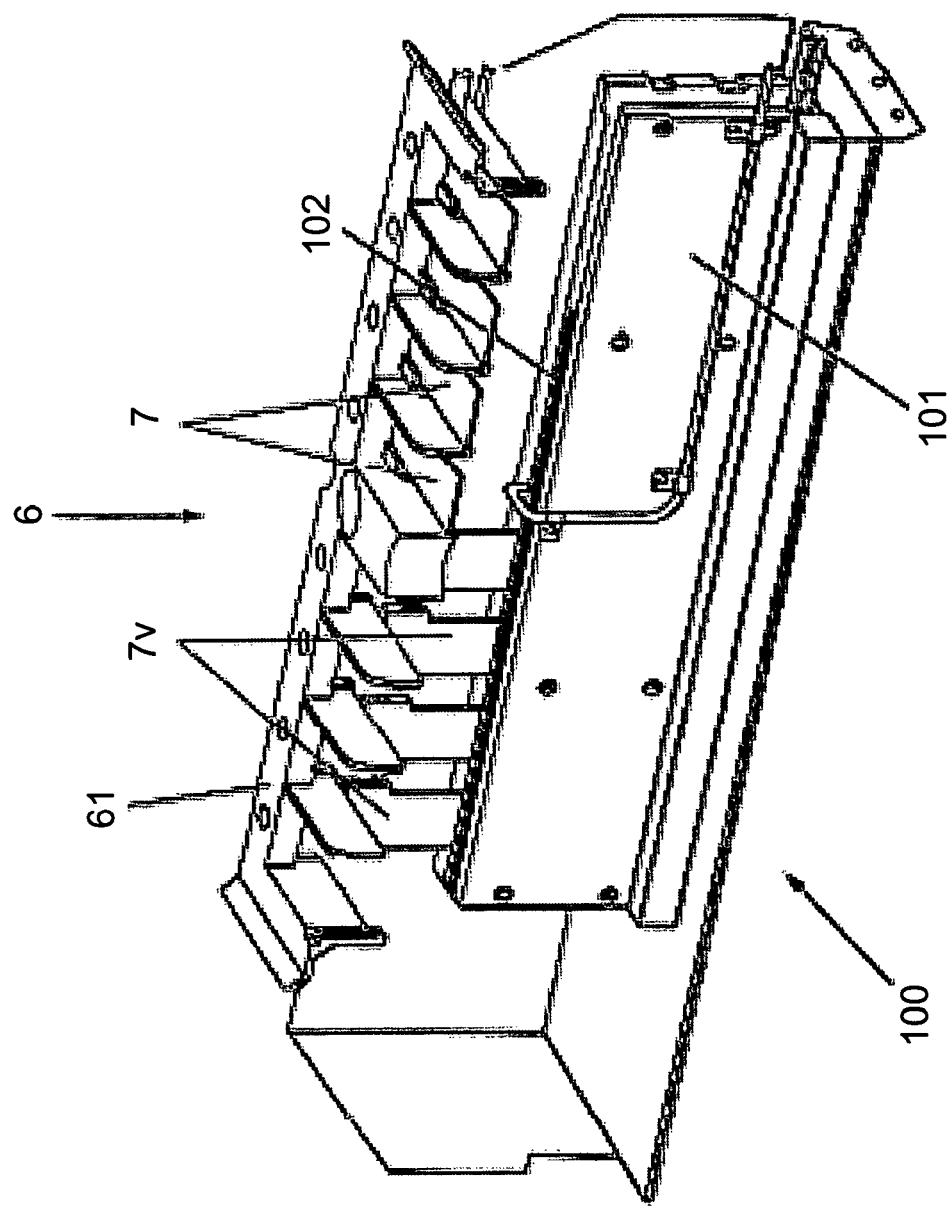
FIG. 28 is a detailed view of the slide rack holder and the processing tank arranged in a drawer assembly.
Figure 29:
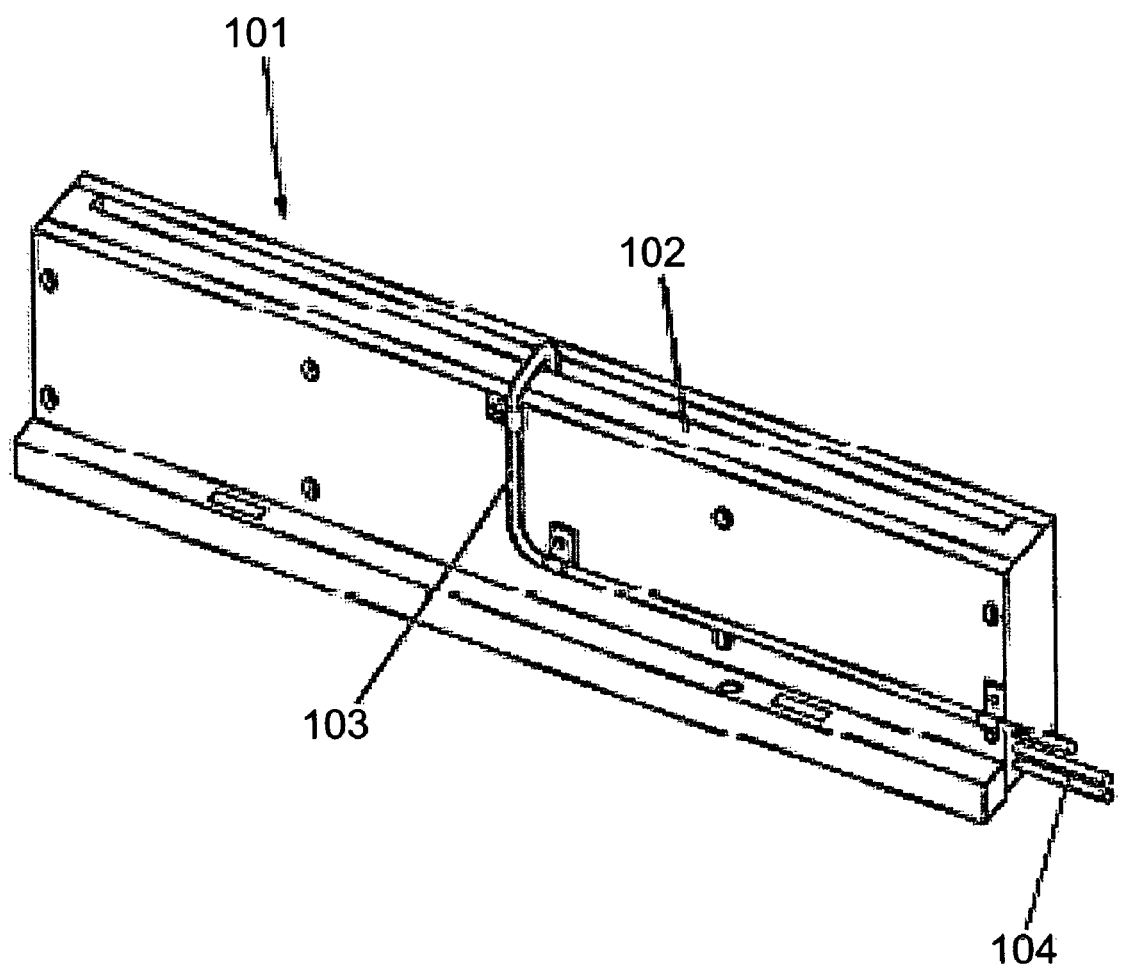
FIG. 29 is a perspective view of a processing tank according to the preferred embodiment of the invention.

The system automates, and in some embodiments mimics or otherwise corresponds to the procedure and physical attributes of the supplies used manually to perform these same pre-treatment processes. Accordingly, a processing tank 101 may be provided (as shown in FIGS. 24, 28 and 29). In some embodiments, components of each processing tank 101, as shown in FIGS. 25 and 26, are configured within a drawer 100. Other components in these figures will be described in detail susequently. In some preferred embodiments, the fluids volume needed to perform pre-treatment processes are maintained but instead of the slide orientation with each other being face-to-face, as in conventional systems, they are side-to-side, although other slide configurations are possible. The processing tanks provide even distribution of fluids across the face of the slide.

In some embodiments, the processing tanks 101 have the ability to heat the slides. This heat is applied evenly across the face of each individual slide by a thermal device. The precision and physical application of the heat can result in standardization and repeatability of process steps. Filling and heating tasks are performed by a computer controlled scheduler, as further described below. Fluid volume may be adjusted to account for the presence or absence of any number of slides.

Figure 6:
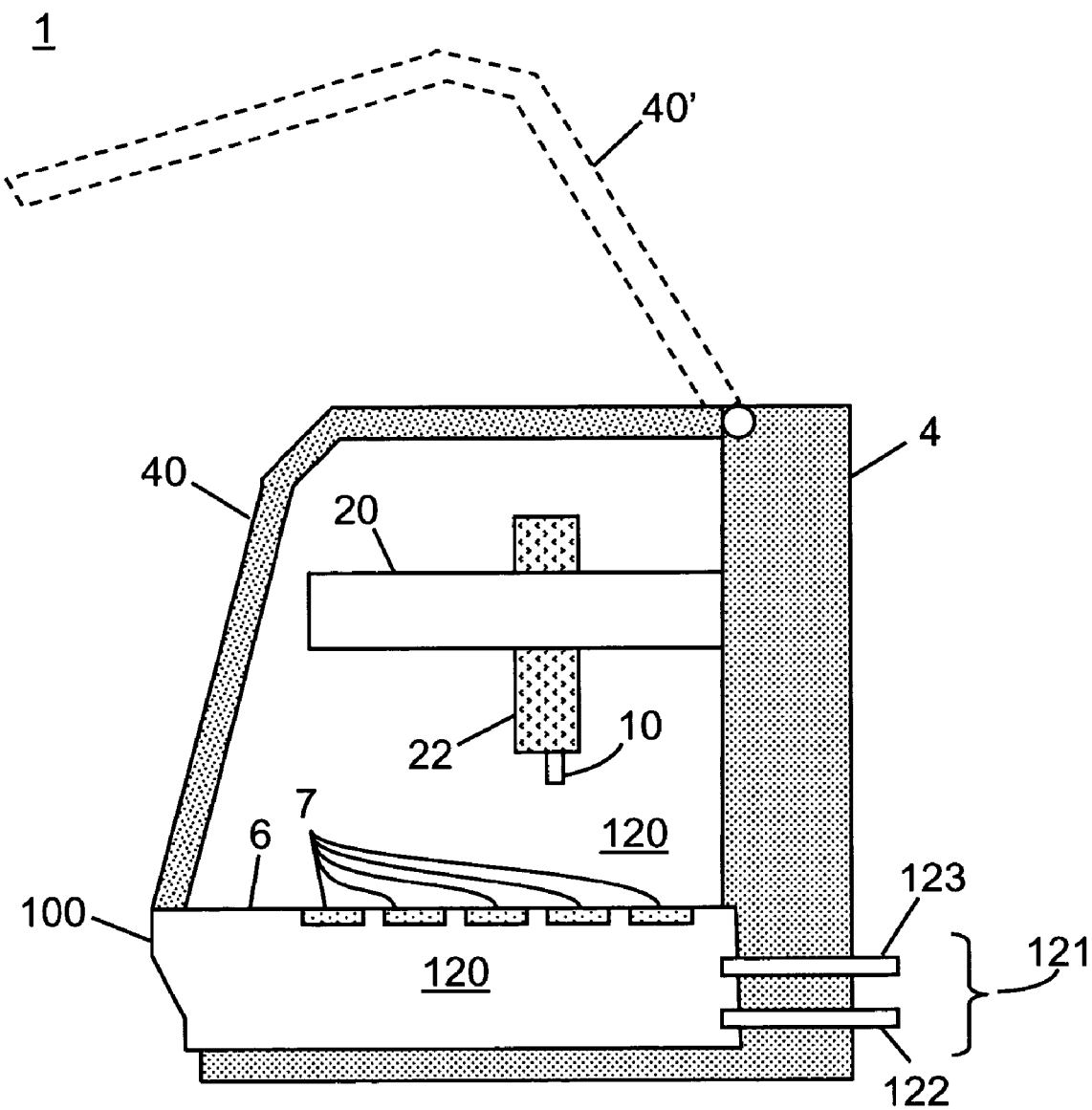
FIG. 6 is a schematic side view of the staining apparatus of FIG. 1.

As shown in FIG. 6, the apparatus 1 is provided with an openable hood cover 40, which is pivotably attached to the frame housing 4. The hood 40 is shown in a closed position and an open position 40' (the latter of which is indicated in dotted lines in FIG. 6). In the bottom of the frame housing 4, the slide rack assemblies 6, potentially in some embodiments in one or more drawer assemblies 100 are provided. An interior space 120 is defined by this hood cover 40 and the frame 4.

A climate control device 121 is provided for controlling the pressure and potentially also the temperature and the humidity of the air in the interior space 120 inside the apparatus 1. This climate control 121 includes an outlet 122 and an inlet 123 allowing for an exchange of air in a controlled manner. Exhausted air from the interior space may be directed to a collection storage or disposed of in other manners depending on the requirements on the location of the apparatus. The exhausted air may—in particular in some staining or other processes—include volatile fumes or other toxic or unwanted fumes from the reagents and other liquids used for the processing of the biological samples.

The ambient air in the interior space 120 is drawn through the rack assembly 6 of the drawer assembly 100 in the slide sections 5. By drawing the fumes out of the interior space 120 at a location close to the heating sources and below the level in which the slides are arranged, the fumes are essentially prevented from diffuse to widely in the interior space, whereby the risk of such fumes coming into unwanted contact with biological samples, other reagents or processing liquids may be avoided.

The temperature, humidity, airflow rate and/or other environmental factors can be controlled by a feed back mechanism from a sensor device, such as one or more sensors arranged in the hood or elsewhere inside the interior space and/or external sensors, which may be advantageous in order to compensate for external influences such as high temperature or extremely dry climate in local areas having extreme climate variations.

Also, it should be understood, that the air drawn into the interior space in addition to be temperature controlled by heating or cooling, also may be added humidity by spraying water droplets or using a filter device, or added other components, like nitrogen gas, carbon dioxide or inert gasses to control the environment in the hood.

In one preferred embodiment, the inlet air is drawn through a humid filter device to ensure high and uniform humidity in the chamber. In another preferred embodiment, the humidity is controlled by spraying water droplets or having a water surface. In yet another preferred embodiment, recycled air is drawn through filters to remove fumes and filters to adjust the humidity. In yet another preferred embodiment, the humidity is controlled to never be below a predetermined level, to prevent drying out of the sample. Also, disinfectants, UV protectants or other compounds could be added to the inlet air to prevent microbial growth or discoloring.

Figure 8:
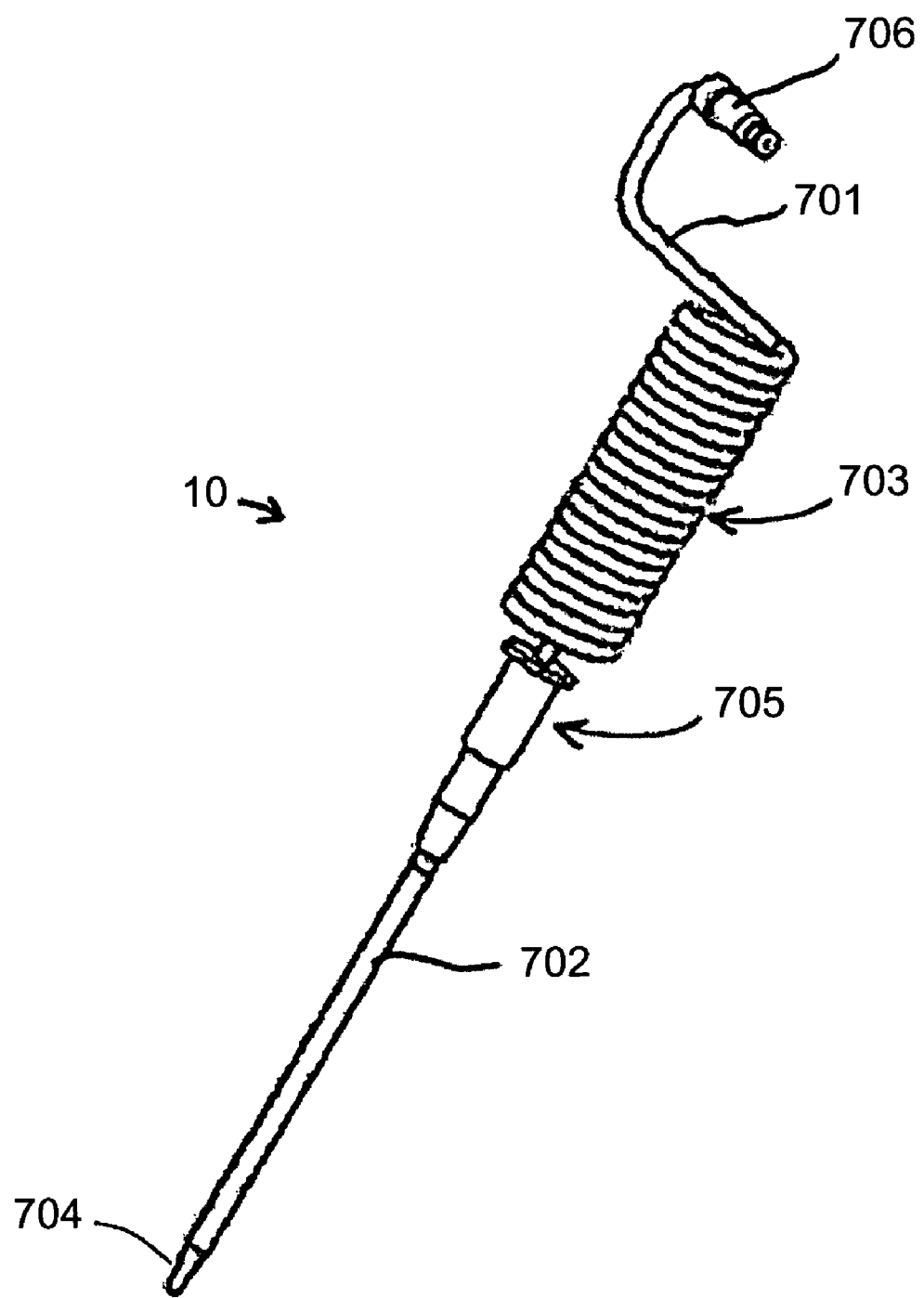
FIG. 8 is a perspective view of a probe according to an embodiment of the invention.
Figure 9:
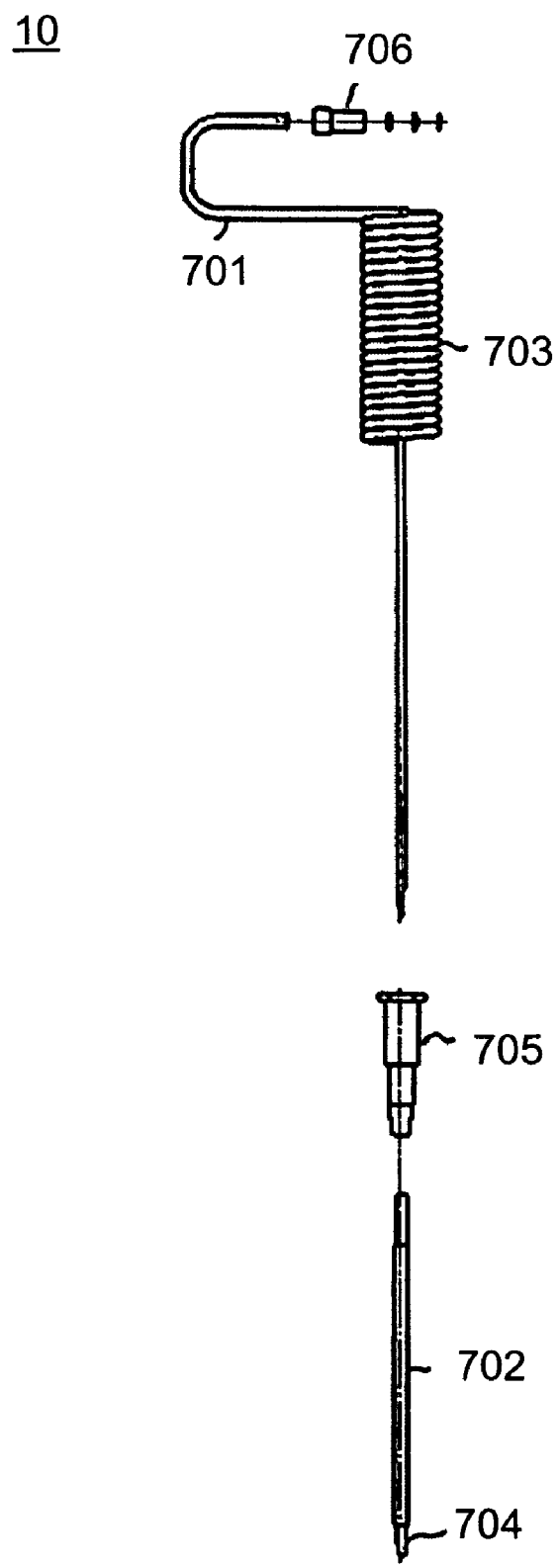
FIG. 9 shows an exploded view of the probe of FIG. 8.
Figure 10:
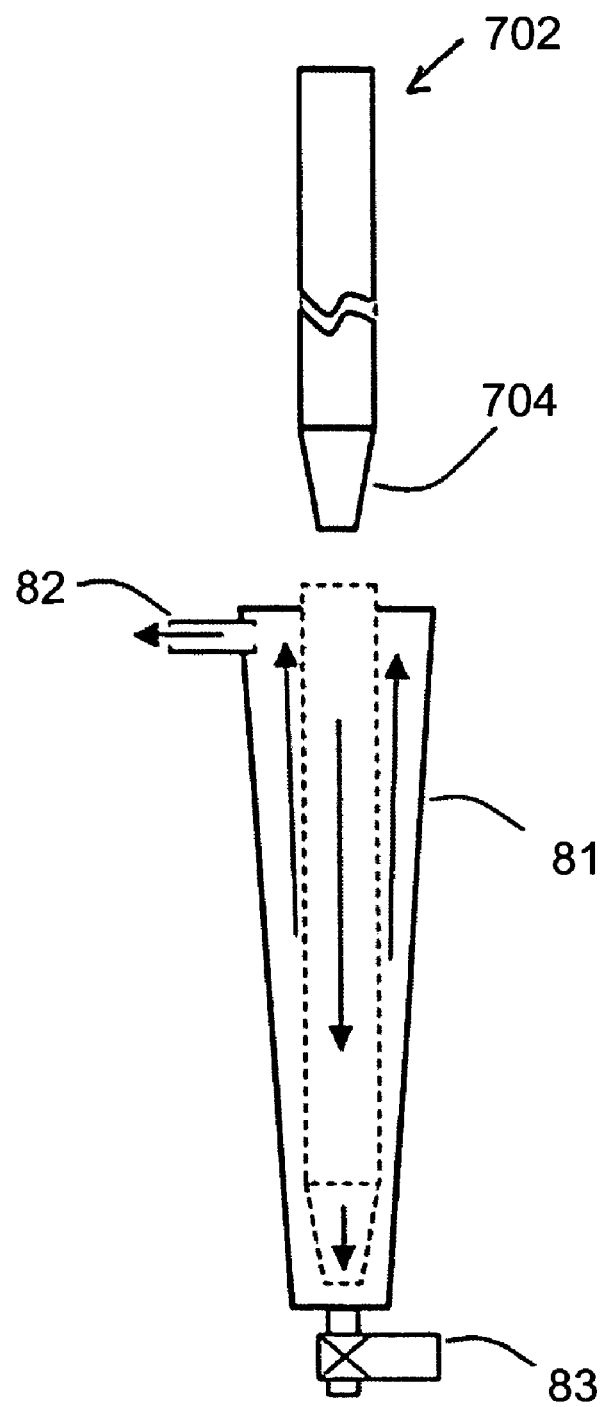
FIG. 10 shows an embodiment of a washing station.

The probe 10 is shown in details in FIGS. 8 and 9. The probe 10 comprises a continuous tubing 701 having a spiral section 703, a probe member 702 having dispensing end also called probe tip 704, and a mounting end having a fitting 705 for mounting on the robot head 22. Preferably, the probe member 702 is a rigid tube, which may be made from a metal, such as a 300-series stainless steel, coated with a fluoropolymer, e.g. Teflon™. Preferably also the inner tubing is a fluoropolymer, such as Teflon™. The materials for the probe must be able to withstand the fluids to which it will be exposed during the sample processing. Such fluids may include aqueous, alcoholic, acidic, basic and organic solvent liquids.

Preferably, the dispensing end 704 (FIGS. 8-9) is a cone. Preferably, the tubing 701 is arranged as an inner lining of the probe member 702 covering the total inner surface of the probe member 702. The other end of tubing 701 ends in a fitting 706 for connection to a computer controlled pneumatic system, able to provide any desired pressure, enabling the probe to aspirate, with-hold, or dispense predetermined amounts of a fluid. The rigid probe member 702 is mounted with fitting 705 in a holder 205 (see FIGS. 7B-7C) on the robotic head 22.

Preferably, the holder 205 is mounted in a rack and pinion drive and may be moved in a vertical direction raising or lowering the probe relative to the underlying samples.

The spirally wound section 703 of the probe 10 comprises at least one winding and preferably a plurality of windings. It is advantageous in that it may flex as the probe 10 is moved up or down or in any other direction by the robotic head 22. Additionally, this section of tubing in the spirally wound section 703 may provide for a considerably increased internal volume in the tube, so that the probe may hold a relatively large fluid content.

EXAMPLE

In a preferred embodiment, the inner diameter of the tubing 701 is about 1.5 mm. In one embodiment, the probe shall be able to aspirate a volume of about 2.5 ml. Accordingly, the length of the tubing 701 has to be about 1.5 m. Such length may be accommodated/achieved by including a coil section having about 20 windings and a diameter of about 20 mm providing for about 1260 mm. By adding thereto the length of the rigid probe member and the tubing section from the coil to the fitting 706, a total of 1.5 m of tubing may be obtained. Obviously, the tubing 701 may be designed to accommodate other fluid volumes. The inner diameter of the tubing is determined such that the viscosity of the fluid will secure the fluid in the probe during the movement of the probe from reagent container to a mixer and/or a slide.

Preferably, the robotic head is adapted to lower the probe 10 when it is aligned on top of a selected reagent container. In a preferred embodiment, a reagent container 3 is covered by a cover through which the probe tip 704 may penetrate when so forced by the robotic head. It is advantageous that the probe 10 is capable of automatically gaining entry into the container, as this allows for a "closed" container design, i.e. a reagent container that constantly through all lifetime of use is provided with a protecting cover or septum.

After having pierced the cover or septum covering a reagent container 3, a predetermined amount of the fluid in the container is aspirated into the tubing 701, and the probe 10 is raised. After having aspirated a predetermined volume of fluid into the probe, it may be advantageous to aspirate some air in order to reduce risk of losing a drop of reagent during the robotic transfer of the probe including the fluid to the staining section accommodating the slide for which the reagent is intended. The robotic head moves the probe until it is located directly above the slide, and the probe may be lowered until it is located a predetermined distance above the slide. Then a valve opens for a short moment to the pneumatic device providing a short interval of a pressure dispensing the predetermined volume of reagent to the tissue on the slide.

Alternatively, with the probe raised above a reagent container, an air gap may be created by aspirating air and the probe may be lowered into the reagent container again aspirating a second volume of the same reagent, raised again repeating the aspiration of air and reagent a plurality of times (typically 5-10 times). After having aspirated a plurality of predetermined volumes of reagent for a plurality of predetermined slides, the robotic head moves the probe including fluid and air to the staining section accommodating the slides for which the reagent is intended. This procedure may be very timesaving as the probe is only moved once from the reagent section towards the slide section. It is useful if the same reagent has to be dispensed onto a plurality of slides.

In a further alternative procedure, and, after having aspirated a first fluid and a first air gap into the probe, a second fluid may be aspirated into the probe tubing from another reagent container and a second air gap and so on until reagents for a plurality of slides have been aspirated.

The pneumatic system may control the pressure in the probe tube, providing, for example, a vacuum or a pressure below or above the atmospheric pressure according to control signals, preferably generated by a computer, and, preferably, according to schedules for the treatment of the slides inserted into the stainer. By having "active" vacuum in the tubing of the probe according to the invention, the design of the reagent containers is not critical for ensuring that a predetermined amount of reagent is transferred from the container.

In one embodiment, the probe 10 may be provided with an attached or incorporated fluid level sensor (not shown) for detecting the amount of reagent remaining within a reagent container. Preferably, the fluid level sensor operates by detecting a change in electrical capacitance. Such capacitance level measurement devices are well-known in the art and are commercially available. A capacitor is formed when a level-sensing electrode of the fluid level sensor is inserted to a known depth into a reagent container. The metal rod of the electrode acts as one plate of a capacitor and a reference electrode acts as the other plate. As the level of the reagent in the container rises, the air or gas normally surrounding the electrode is displaced by the reagent's different dielectric constant. The value of the capacitance thus changes because the dielectric between the two plates has changed. This capacitance change is detected electronically and then converted it into an output signal.

With the probe according to the invention, it is possible to provide both precision and accuracy of the aspirated volumes of reagents. This is very important as the staining result may be deteriorated if the applied volumes differ from the recommended sizes, and this could later cause difficulties when analyzing the stained sample in a microscope and might give reason to a faulty diagnosis.

Whenever needed—and typically when a different reagent is to be aspirated and dispensed—the robot system may move the probe to a washing station 8 (FIG. 1, FIG. 2, FIG. 10, FIG. 14) that is able to clean the probe 10, thereby removing all traces of the preceding reagent from the probe.

In a preferred embodiment, the washing station 8 (FIG. 10) comprises deep receptacle 81 able to accommodate a length of the rigid probe member 702 at least corresponding to the length which may have been dipped into the reagent. Through valves (not shown), the tubing end with fitting 706 may be connected to a source of at least one wash solution or cleaning fluid, which will pass through the tubing 701 and finally be ejected from the probe tip into the washing receptacle 81. Further, the wash solution or cleaning fluid passes on along the outer surface of the probe 702 and exits the receptacle 81 through an outlet 82 to waste arranged a distance above the bottom and preferably close to the top of the receptacle 81. The receptacle 81 may be emptied by opening a normally-closed bottom valve 83.

In order to dry the probe after the wash, thereby removing any traces of the cleaning fluids, a stream of air may be directed through the probe by connecting the tubing end with the fitting 706 through a valve to an air source.

In a preferred embodiment, the reagent containers or bottles 3 are designed to fit into the reagent section of the sample processing apparatus, and to cooperate with the design of the probe.

Preferably, the reagent section comprises a plurality of receptacles able to receive a plurality of reagent containers. Preferably, a cross section of these receptacles corresponds to a cross-section of the reagent container. Further, preferably, the cross-section is a non-symmetrical polygon. In a presently preferred embodiment, shown in several of the FIGS. 11A-11D, the cross-section is a pentagon, and more specifically a pentagon having two sides, and three angles in common with a rectangle. In other words, the preferred cross-section is a rectangle with one corner-section replaced by a slanted/oblique fifth side.

The advantage of the preferred cross section is that the containers can only be arranged in the receptacles with a specific orientation. Also, any other container of different design cannot fit into the receptacle. This may help to avoid problems with faulty supply of reagents. An alternative description of the container shape is that the containers are keyed.

This keying or mating of a container to a receptacle is very important as the top of the container (shown in FIG. 11A) in a preferred embodiment comprises two features: 1) a neck 137 with a cover providing access to the fluid content, and 2) an identification 138 relating to the content of the container, preferably including information specific to the content, such as, e.g., name of chemical substance, date of delivery, date of expiration, and any other relevant information. Alternatively, the identification could be a coded number providing access through a computer to an address comprising such information. It is essential for the automated robotic control of the probe movements that the containers are located precisely in the predetermined positions in the receptacles in the reagent section, so that the probe, when lowered, will hit the cover of the container while, at the same time, the camera (or another sensor device) may read the identification and ensure that the correct reagent will be aspirated.

In a preferred embodiment, the computer system controlling the operation of the robotic system is programmed to start a new sample processing by performing a search of all reagents, identifying the location of the various reagents, preferably using the probe to measure the level of all reagents. In a further preferred embodiment, the computer system is programmed to alert the user if a reagent level is too low to accomplish the staining task for which it is set up. To accomplish this automated operation, it is essential that the reagent containers remain fixedly located in the identified positions. Accordingly, the design of the reagent containers must cooperate tightly with the design of the receptacles in the rack assemblies wherein they are located.

In one embodiment, illustrated in FIGS. 11A-11D the container is a 50 ml container 125 having a cross-section that is a rectangle with one corner-section replaced by a slanted/oblique fifth side. The 50 ml container or bottle 125 comprises a bottom 130, five upright sides 131, 132, 133, 134,135 and atop 136 with a neck 137. In a preferred embodiment, the top, as shown in details in FIG. 11B, has identification 138 that is, preferably, a label and that identifies the content of the container.

In view of the fact that some reagents are used in various volumes or even seldom, and still others may have a short shelf-life, needing to be replaced often, there is a need for providing the reagents in containers having different volumes. In order to be able to arrange a plurality of containers having different volumes in the same reagent station with a plurality of identical receptacles, it is preferred to provide an assembly comprising a tube-like covering or shell, called "an adapter", and an internal bottle within the adapter which may be provided in different sizes, having internal volumes of e.g., 1 ml, 2 ml, 5 ml, 10 ml, 15 ml, 20 ml, 25 ml or similar volumes. Generally, the typical reagent volume for an apparatus according to the present invention will be between about 1 ml and 25 ml.

In a preferred embodiment, the covering is a tube-like element 200 (FIG. 11E) having the same outer cylindrical surface as the 50 ml container, i.e., the cross-section is a rectangle with one corner-section replaced by a slanted/oblique fifth side. Accordingly, the adapter 200 comprises the five upright sides 231, 232, 233, 234, and 235, but, being hollow, does not have a top surface.

In order to allow for the computer-controlled automated aspiration of reagents, it is essential that the internal bottles are arranged in a fixed manner inside the tube-like covering 200 enabling the probe to penetrate in a well-defined manner into the fluid content of the bottle. This is achieved by providing the covering and the inner bottles with corresponding projections 221 and indentations (not shown) respectively and/or vice versa, ensuring a well-defined position of the inner bottle inside the covering. The projections should ensure a correct orientation in all directions. It should not be possible to insert the inner bottle into the adapter 200 in any way other than the intended orientation and position. In a preferred embodiment, this is achieved through the combination of projections and indentations, the projections 221, 223 being shown in the FIGS. 11F-11H, relating to the adapter.

In a preferred embodiment, a cap 320 (shown in FIGS. 12A-12B) is provided, the cap 320 having an internal thread 322 that mates with an external thread of a corresponding bottle, thereby providing a closure for the bottle. The cap 320 may comprise a circular opening through which the probe may aspirate the fluid content in the bottle. In this manner, no operator has to unscrew a cap in order provide access to the content. The probe may simply reach the fluid content when the probe is lowered by the robotic system until the probe makes contact with the fluid. Preferably, a fluid level sensor of the probe is in electrical connection with electronic circuits enabling a determination of the fluid level in the container. Alternatively and in some embodiments, a second database method of reagent volume tracking may be used instead of or in conjunction with previously detailed electronic method. The database method employs the use of a database to track the usage of a reagent removed by the probe from a specific container and calculates the remaining available volume.

To protect the reagent fluids from contamination as well as evaporation, it is highly desirable to provide tight closures for the bottles. To this end, the circular opening in the cap 320 has a skirt 324 including a peripheral outwardly projecting rim or lip 328 and a peripheral/surrounding indentation or groove 329 able to cooperate with and fixate a corresponding septum 340 (FIGS. 13A-13B) comprising a flexible material such as polypropylene. The corresponding septum 340 has an upward skirt 344 with an inwardly projecting rim or lip 346 and groove/indentation 348, able to cooperate with the indentation 329 and rim/lip 328 inside the cap 320. When the cap 320 is secured to the bottle neck 255, the upper end of the neck will support and force the lip 346 to stay locked in the groove 329.

Preferably, the septum 340 (FIGS. 13A-13B) comprises a plurality of sectors or flaps 351, 352, 353, such as 2, 3 or 4 sectors, which are free to flex upwards or downwards thereby allowing a probe to penetrate the septum. After aspiration of the predetermined amount of fluid, the probe is raised again, thereby being retracted from the reagent bottle. During retraction of the probe, the flaps will wipe off the reagent from the outer surface of the probe. After retraction of the probe, the flaps return to their original position forming an almost tight closure inside the cap on top of the bottle. This septum has several advantages: Evaporation of reagent is reduced, and the wiping action of the flaps saves reagent from being carried away on the outer surface of the probe when the probe is raised for movement to the slide section.

Figure 14:
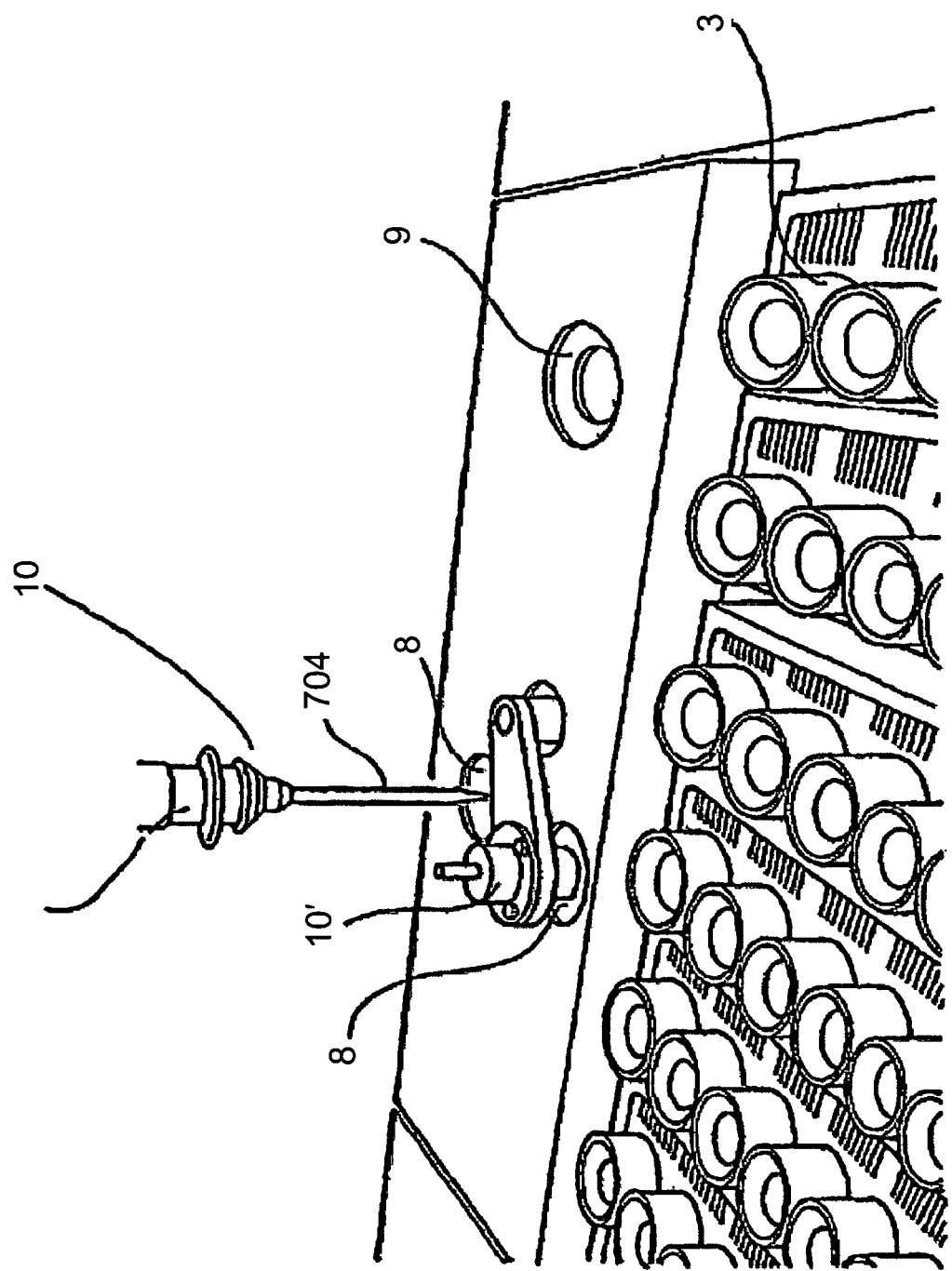
FIG. 14 is a enlarged perspective view of a detail of the work area shown in FIG. 3.

Now, referring to FIG. 14, as illustrated in detail in that figure, the staining apparatus 1 of the present invention comprises, in an embodiment, at least one probe washing station 8 (see also FIG. 10) and further comprises, in an embodiment, a reagent mixer 9, such that the robot arm is furthermore arranged to transfer the probe tip 704 to the washing station 8 as well as to the reagent mixer 9. The reagent mixer 9 will be described in detail below with reference to FIGS. 15 and 16. In the embodiment shown in FIG. 14, a releasable connection 12 is provided between the probe 10 and the robot arm, enabling the replacement of the probe 10 held by the robot arm by placing the probe 10 in one of a number of free washing stations 8, where it is released by the releasable connection 12, and where a new clean probe 10' is connected to the robot arm by means of the releasable connection 12.

The apparatus comprises a reagent mixer 9 having a mixing cup 13 (FIGS. 15, 16) wherein two or more selected reagents may be placed by means of the robot arm and the probe 10. The reagent mixer 9 thereby provides on-board mixing of any reagents contained in the reagent containers 3, which, preferably, comprise the bottles 125 (FIGS. 11A-11D). The reagent mixer 9, thereby, enables more staining processes, e.g. staining requiring the use of mixing of insoluble reagents, or reagents which may only be effective a short time after mixing, are facilitated to be performed automatically within the staining apparatus without the requirement of human interaction.

Figure 15:
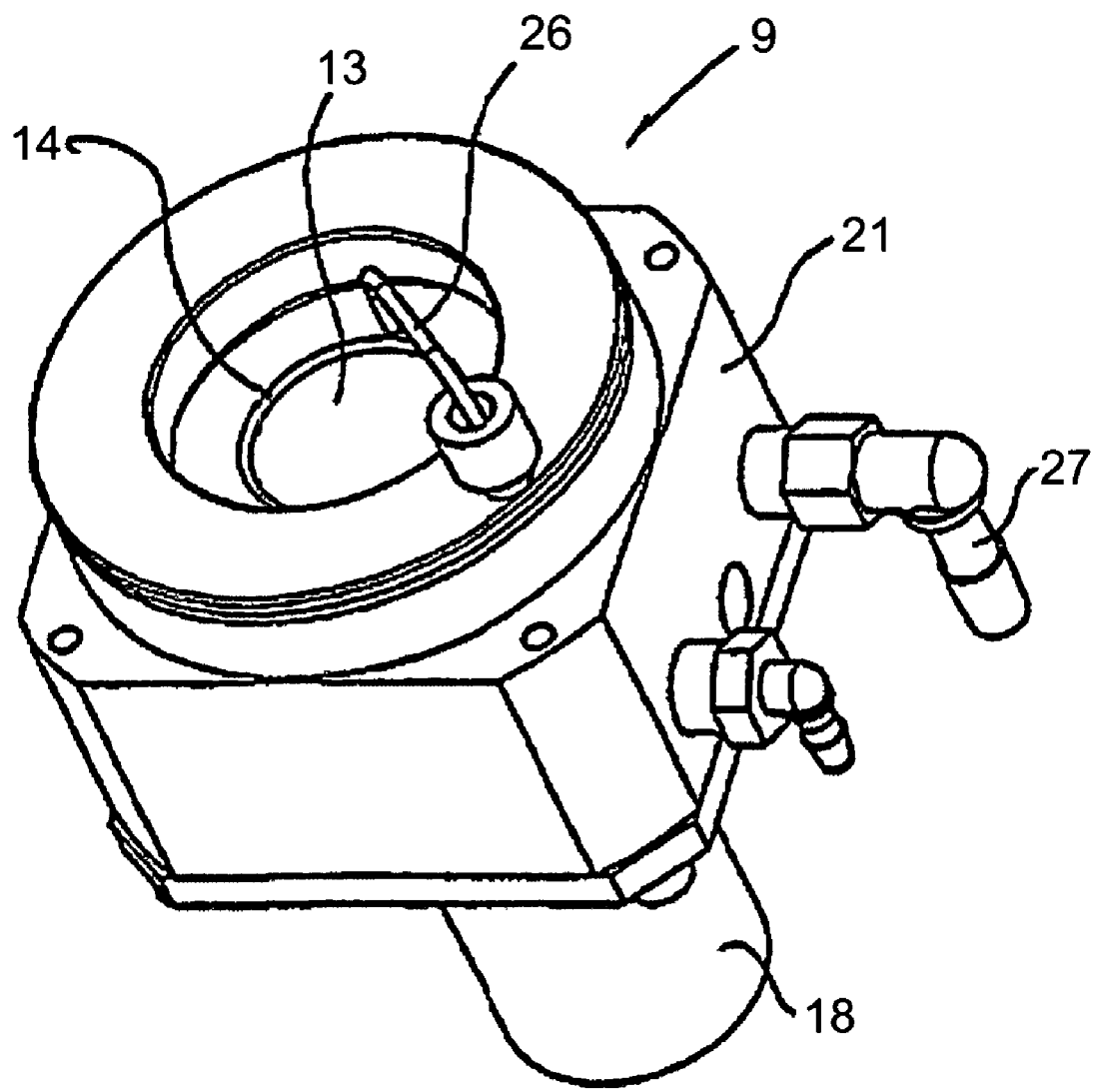
FIG. 15 is a perspective view of a reagent mixer according to the invention.
Figure 16:
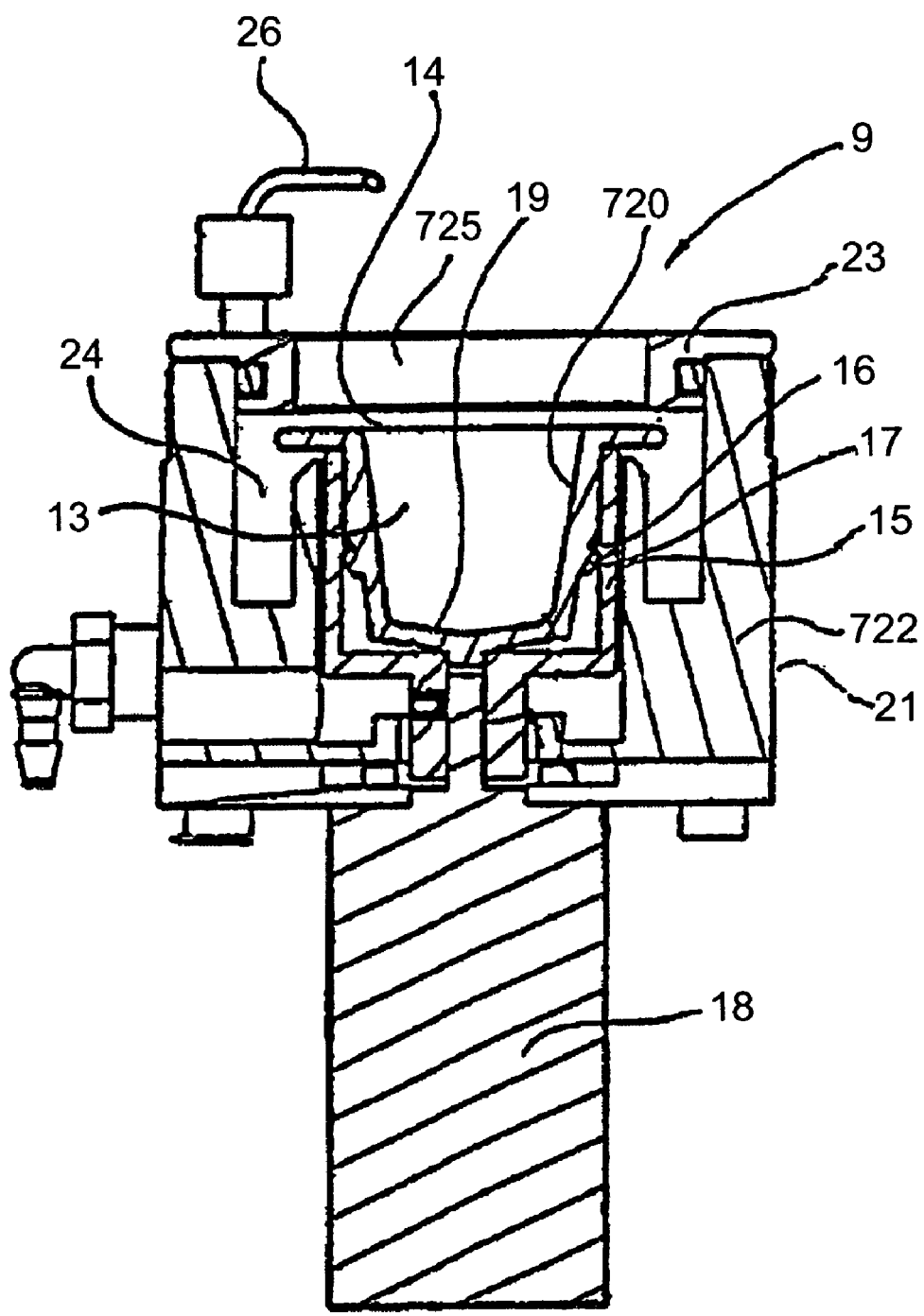
FIG. 16 is a vertical cross-section of the reagent mixer according to FIG. 15.

The mixer 9, shown in detail in FIGS. 15-16, comprises a mixing cup 13 for receiving reagents released from the probe 10. The mixing cup 13 is placed into a holder 15 by means of a complementary snap fitting means 16 and 17 arranged on the inside of the holder 15 and the outside of the mixing cup 13, respectively. A motor 18 is arranged for rotating the holder 15 and thereby the mixing cup 13, either intermittently clockwise and anticlockwise in order to provide a mixing of reagents contained in the mixing cup, or by spinning the holder 15 and thereby the mixing cup 13 in order to fling out waste reagents or cleansing liquid from the mixing cup 13.

For the latter purpose, the mixing cup 13 is preferably provided with sidewalls 720 extending upwardly and outwardly from the bottom 19, e.g. forming a frusto-conical cavity, and the mixing cup 13 has an upper rim 14 allowing the reagents to escape from the mixing cup 13 during the spinning process. Further, the rotating action of the cup allows air to escape from the mixture and prevent foaming. The rotating action can suppress the formation and build-up of foam by forcing the air/liquid foam down to the liquid surface.

The reagent mixer 9 furthermore comprises a housing 21 having sidewalls 722 surrounding at least the rim 14 of the mixing cup 13 and thereby forming splash faces for collecting any liquid flung out from the mixing cup 13. The housing also comprises a lid 23 for enclosing a space 24 surrounding the mixing cup 13 in order to avoid reagent spills outside the space 24. The lid 23 has a central opening 725 allowing reagents from the probe 10 to be dispensed into the mixing cup 13 from above the reagent mixer 9 as well as allowing the probe 10 to enter the mixing cup 13 for collecting the mixed reagents.

According to a preferred embodiment of the present invention, the housing also comprises a hose connection 27 for draining waste reagent or cleansing liquid from the space 24, and a tap 26 is arranged for dispensing cleansing liquid into the mixing cup 13 when required.

Having the appropriate input data, the control means of the apparatus operates the robot arm to commence a staining or treatment run by firstly moving the probe to a first reagent container 3, into which the probe tip 704 is inserted. Once the probe tip is inserted into the liquid of the container, liquid is aspirated into the probe 10 in an amount corresponding to the number of samples to be stained or treated, in accordance with the input data provided to the control means.

The probe 10 is subsequently, in a first operating mode moved by the robot arm towards the slide section 5 in which the slides 7 are mounted. The slides 7 are situated with the surface horizontally oriented and the probe 10 releases the required amount of reagent on the appropriate slides in accordance with the input data. Alternatively, the probe 10 is in a second operating mode moved by the robot arm towards the reagent mixer 9 where it releases the reagent into the cup 13 of the reagent mixer 9, and is subsequently moved to the probe washing station 8, where the probe 10 is either washed or—in the alternative embodiment (FIG. 14)—released into a free washing station 8, and another probe 10' situated in another washing station 8' is connected to the robot arm. The robot arm moves the new clean probe 10' to a second selected reagent container 3 for collecting a selected amount of reagent from the second container 3, and the probe 10' is thereafter by means of the robot arm moved to the reagent mixer 9, where the reagent in the probe 10' is dispensed into the cup 13 of the mixer containing the first selected reagent. The second operating mode can, according to the invention, be commenced several times if more than two reagents are to be mixed for a specific staining or treatment process.

The reagent mixer 9 mixes the reagents in the cup 13 thereof, and a clean probe 10 picked up from the washing station 8 by the robot arm is lowered into the cup 13 of the reagent mixer 9 to collect the mixed reagents, whereafter the robot arm moves the probe 10 towards a slide section 5 containing the slides 7, at which the probe 10 releases the required amount of mixed reagent on selected slides 7 in accordance with the input data.

The robot arm with probe 10 is subsequently directed to a free washing station 8, and the probe 10 is either washed or alternatively replaced by a clean probe 10', whereafter the process in accordance with the first or the second operating mode may be repeated or continued with a new reagent or reagent mixture.

Figure 7B:
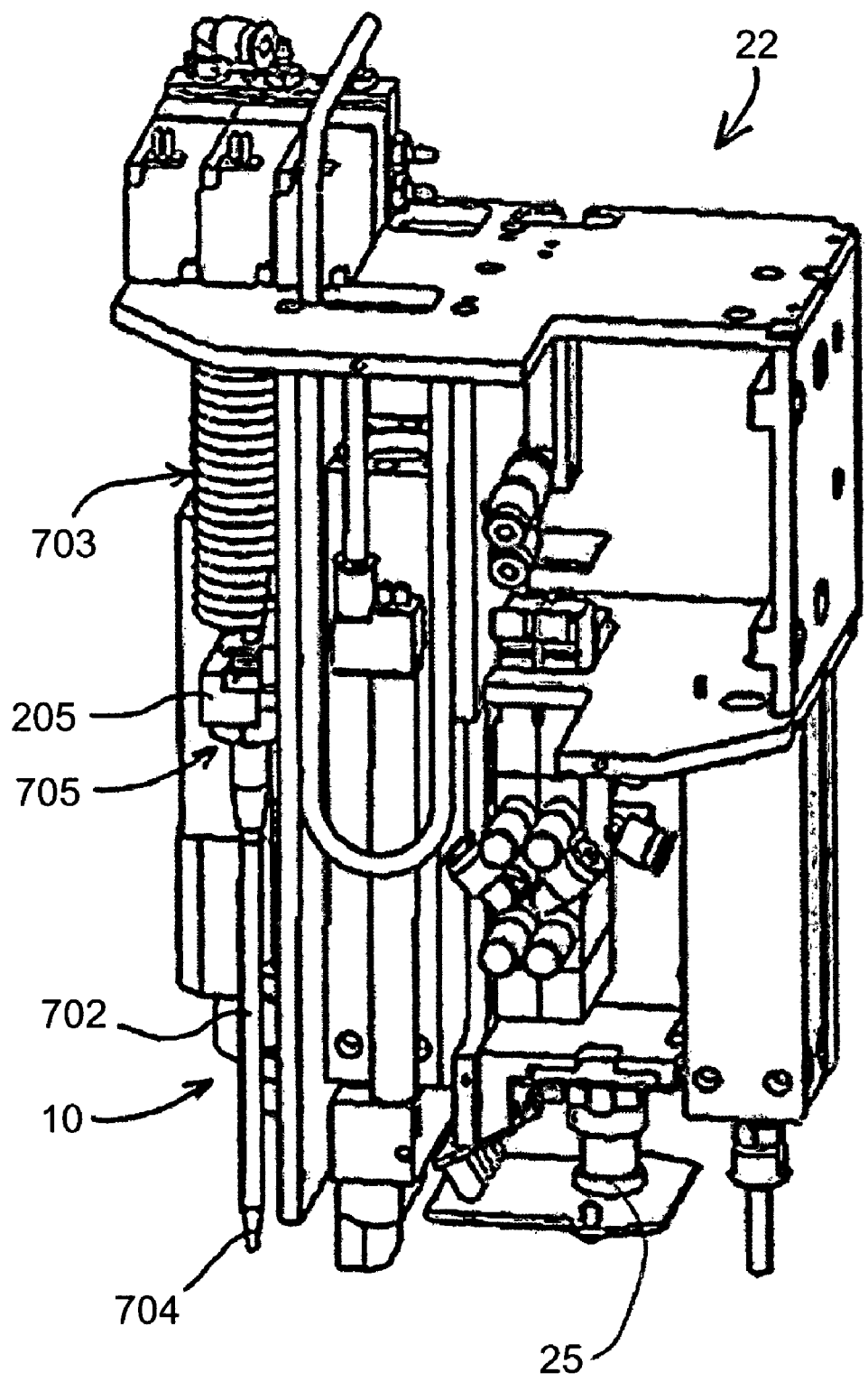
FIG. 7B shows a first view of an embodiment of a robotic head with a probe according to the invention mounted thereon.
Figure 7C:
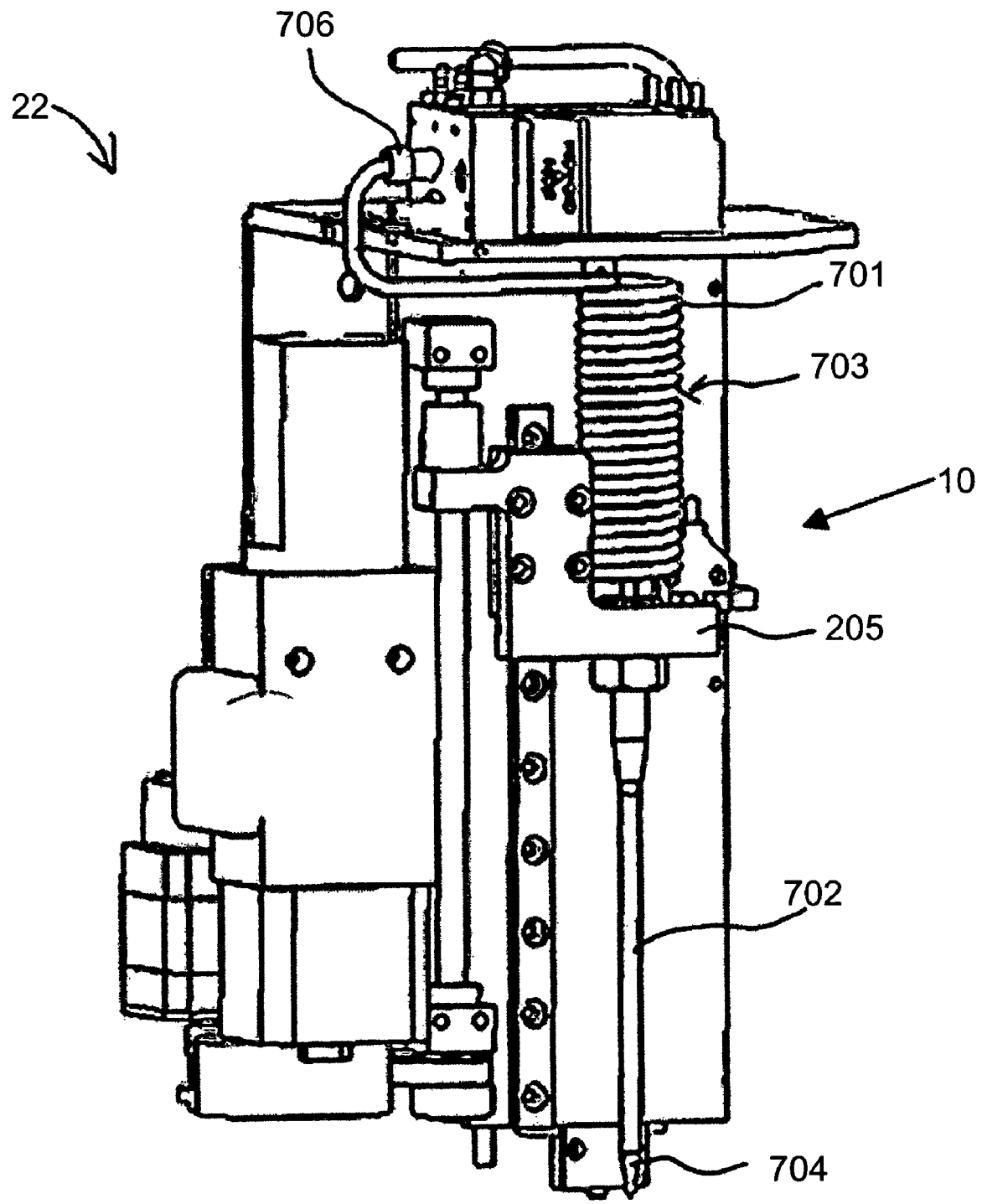
FIG. 7C shows a second view of the robotic head of FIG. 7B, viewed perpendicular to the view in FIG. 7B.

In an embodiment, the present invention may include providing an optical sensor 25 on a robotic element and perhaps moving the optical sensor to a predetermined position through action of the robotic element. As but one example, the robotic head 22 may be provided with an optical sensor 25, perhaps even a CCD camera 25 pointing downwards (FIGS. 7A-7B). An optical sensor may be positioned on or, perhaps, more broadly in response to, the robotic element. After the optical sensor is positioned, image data may be recorded at the location at which the optical sensor is established. The camera can be used 1) as an area locator, 2) to locate a tissue area, 3) to apply reagent based on location and area. The scanned image may be analyzed for reagent analysis or other analyses.

Figure 11A:
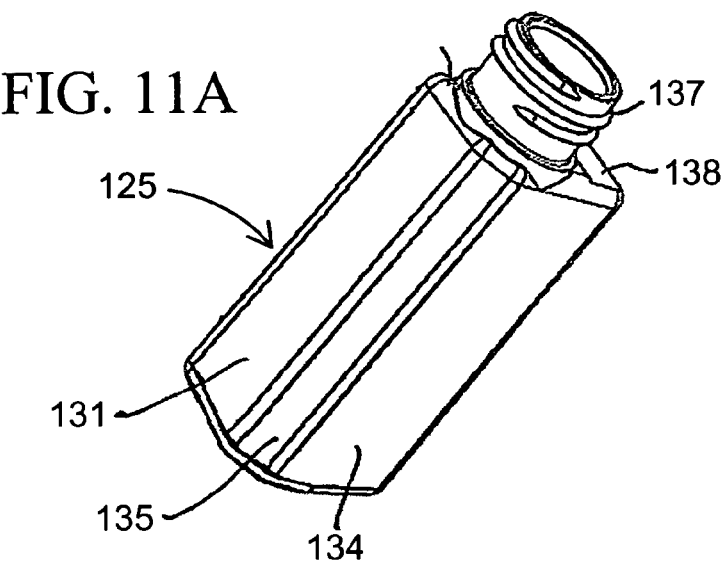
FIG. 11A shows a perspective view of a 50 ml reagent container.
Figure 11B:
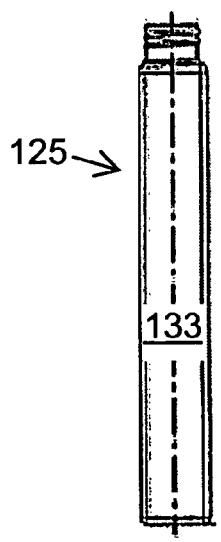
FIGS. 11B and 11C show side views of the same container of FIG. 11A.
Figure 11C:
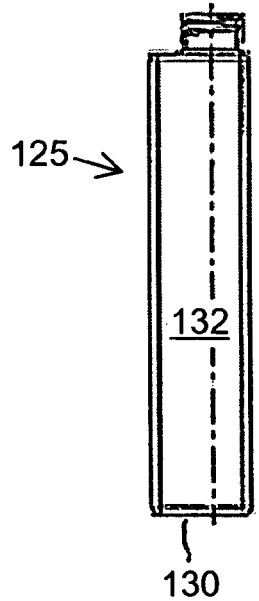
Figure 11D:
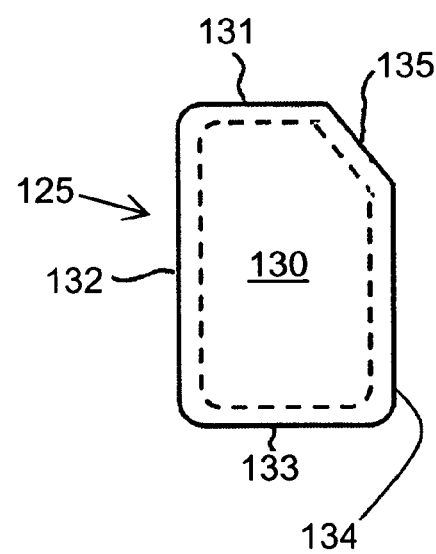
FIG. 11D shows a bottom view of the same container of FIG. 11A.
Figure 11E:
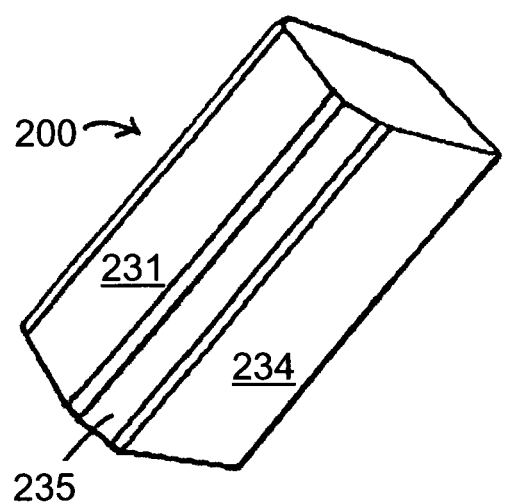
FIG. 11E shows a perspective view of an adapter or covering for accommodation of smaller containers.
Figure 11F:
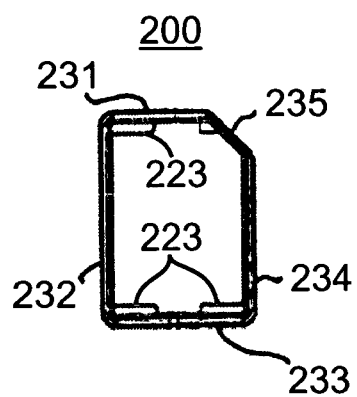
FIG. 11F shows a bottom view of the adapter of FIG. 11E.
Figure 11G:
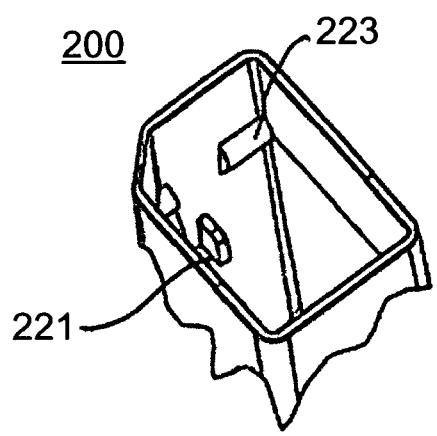
FIG. 11G a perspective view of the adapter of FIG. 11E seen from the top.
Figure 11H:
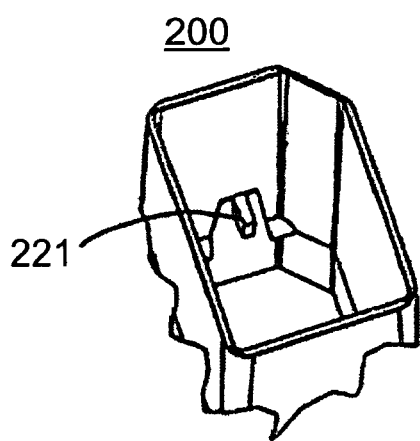
FIG. 11H shows a perspective view of the adapter of FIG. 11E, seen from the bottom.
Figure 12A:
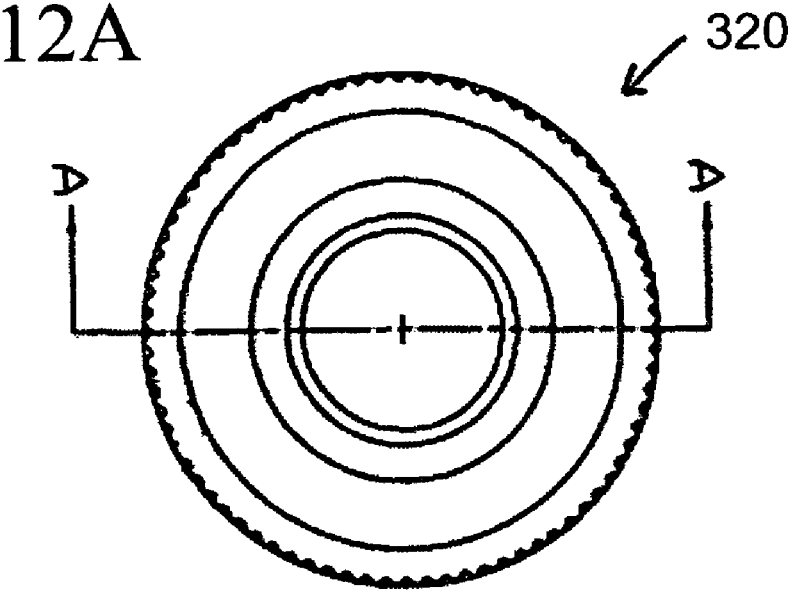
FIG. 12A shows a top view of a cap for a container.
Figure 12B:
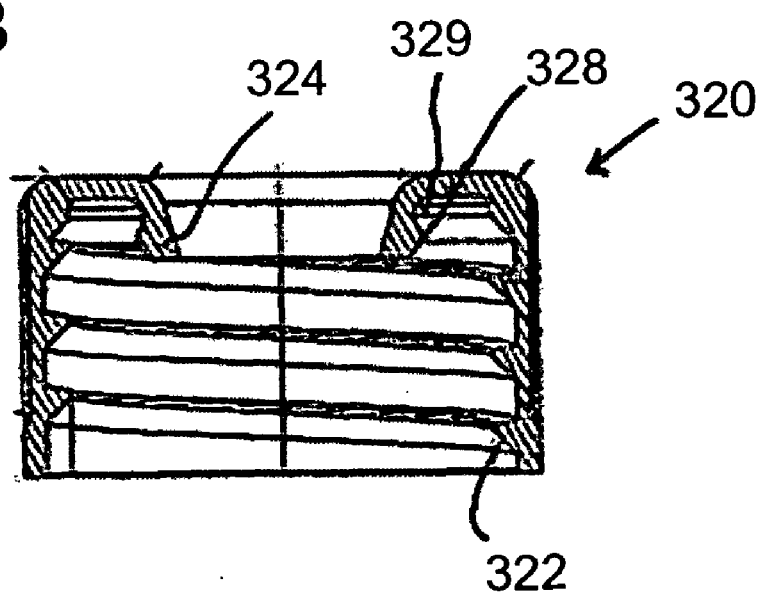
FIG. 12B shows a cross-sectional view of the cap of FIG. 12A.
Figure 13A:
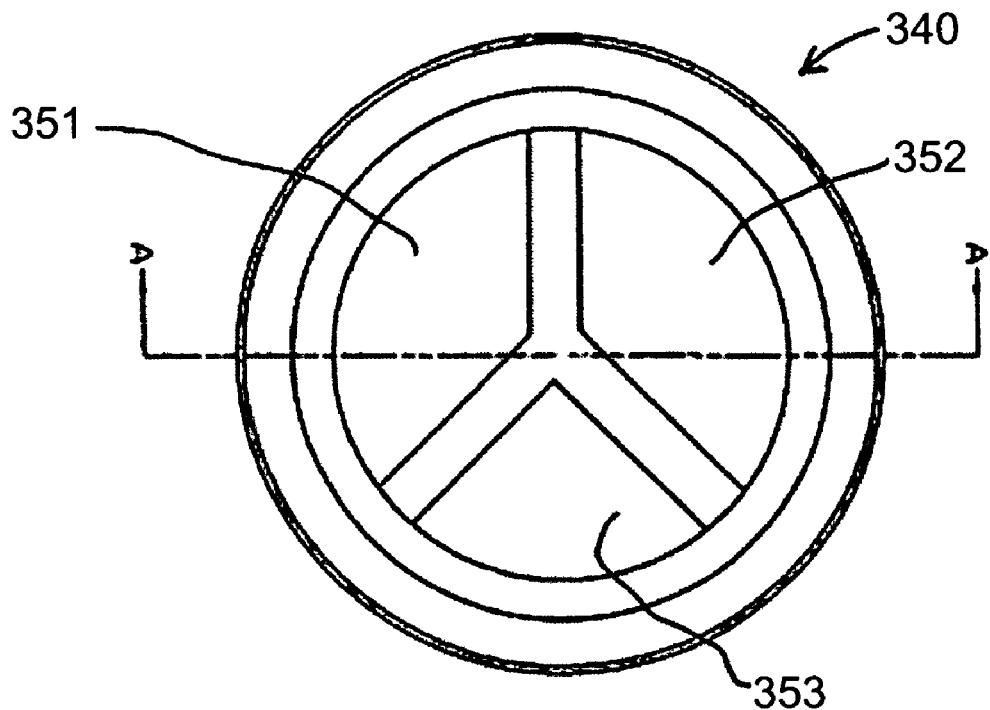
FIG. 13A shows a septum.
Figure 13B:
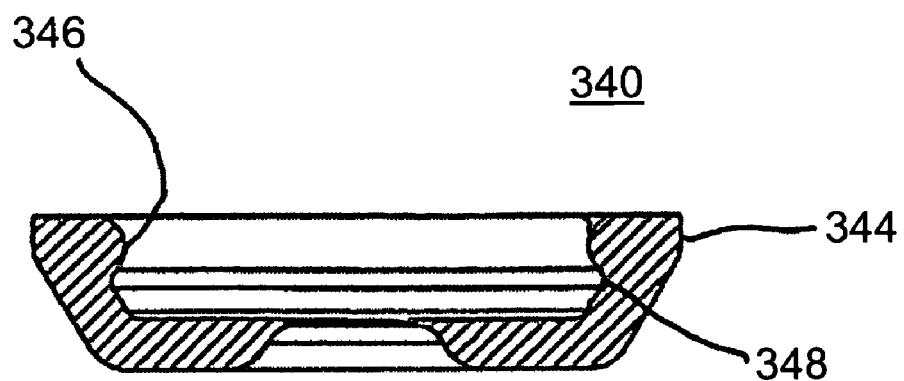
FIG. 13B shows a cross-sectional view of the septum along the line A-A in FIG. 13A.
Figure 17:
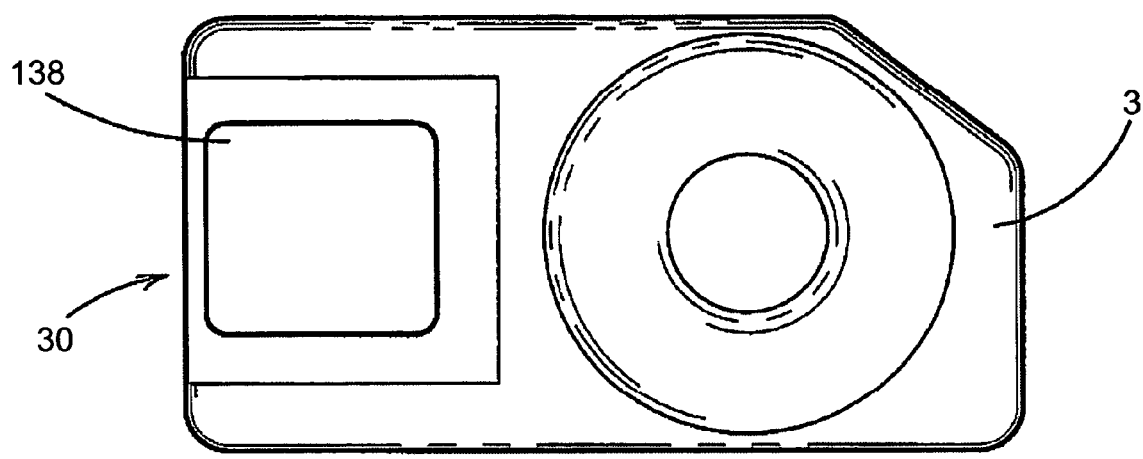
FIG. 17 is a top view of a reagent bottle with optical identification means.

As shown in FIG. 17, the reagent container 3 may be provided with ah area 30 on a surface on which to mount an optical identification element 138 (FIG. 11A, FIG. 17). This optical identification element may be an adhesive label carrying encoded information about the content of the container 3, such as reagent type, date of manufacture, expiry date, etc. The encoded information could be in the form of a data matrix code, an Infoglyph code or any other kind of two-dimensional (2-D) code, and could in principle also be a simple one-dimensional (1-D) code, i.e. a bar code. Additionally, the optical identification element or label 138 may also be provided with human readable text to aid the operator handling the reagent bottles e.g. during loading of bottles into the staining apparatus.

Figure 18:
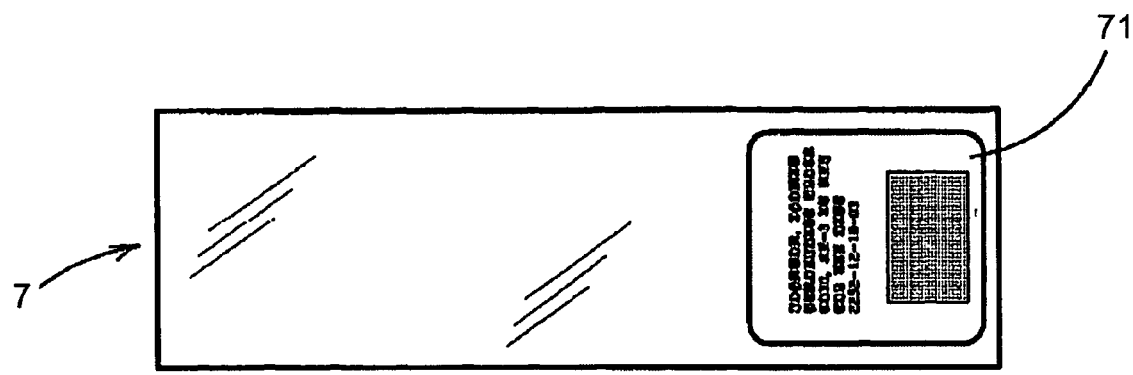
FIG. 18 is a view of a microscope slide with an optical identifier label thereon.
Figure 19:
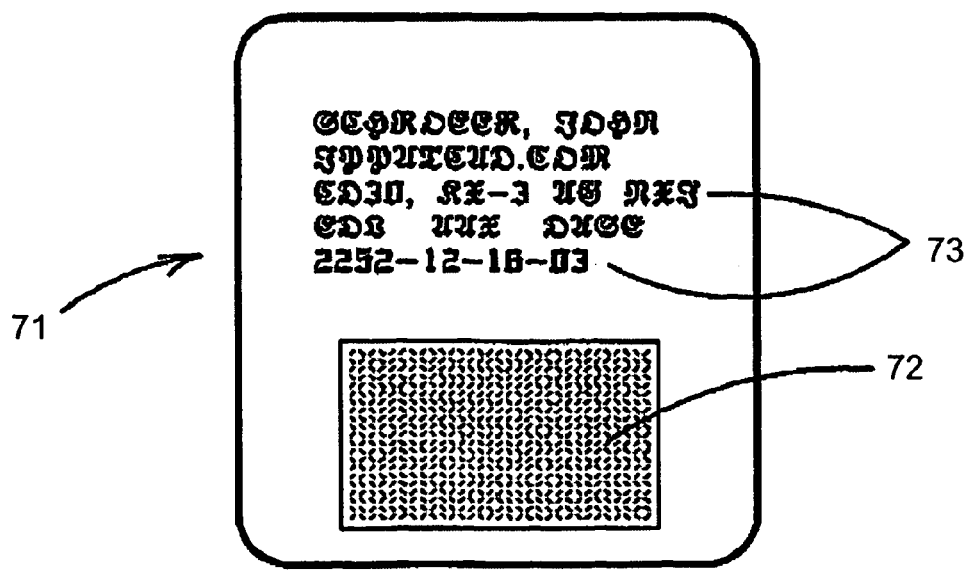
FIG. 19 is an example of a lay-out of the label of FIG. 18.

FIG. 18 shows a slide 7 with a preferred optical identification element, that is preferred label 71, mounted thereon. One layout of the label 71 is shown in FIG. 19, The label 71 may be an adhesive optical identifier, which may be prepared for the particular slide and printed on a label printer (not shown) or any other suitable printing device. It is even possible that, in a particular situation, if a batch of slides is to be subjected to the same treatment, a series of identical labels could be provided for the slides. The label 71 may comprise an area 72 for encoded information about the tissue sample on the slide 7, such as patient data, date and file number, the staining protocol and/or the series of process steps. Furthermore, the label 71 may be provided with one or more rows 73 of human readable text and/or blank space for the laboratory personnel preparing the slides to write on the slide label.

Figure 20:
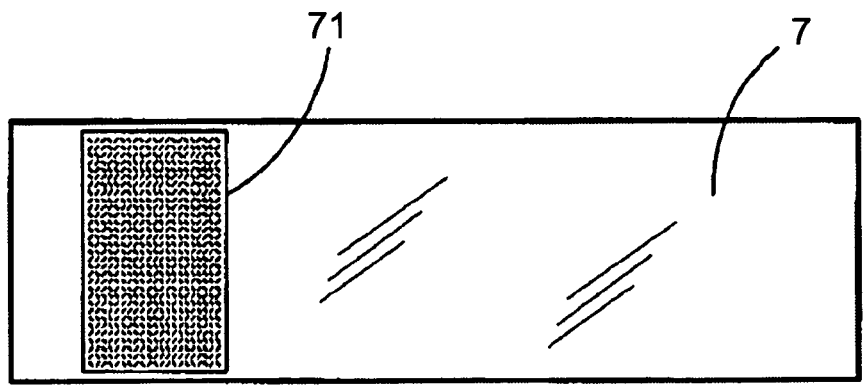
FIG. 20 is an example of a first kind of optical identifying means on a slide.
Figure 21:
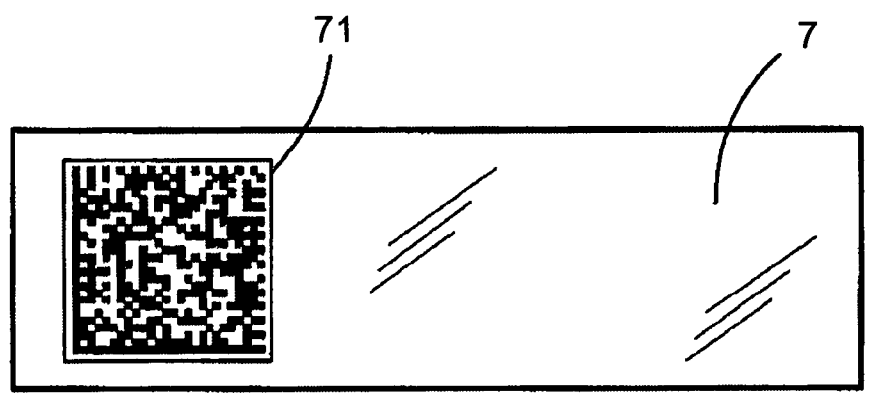
FIG. 21 is an example of a second kind of optical identifying means on a slide.
Figure 22:
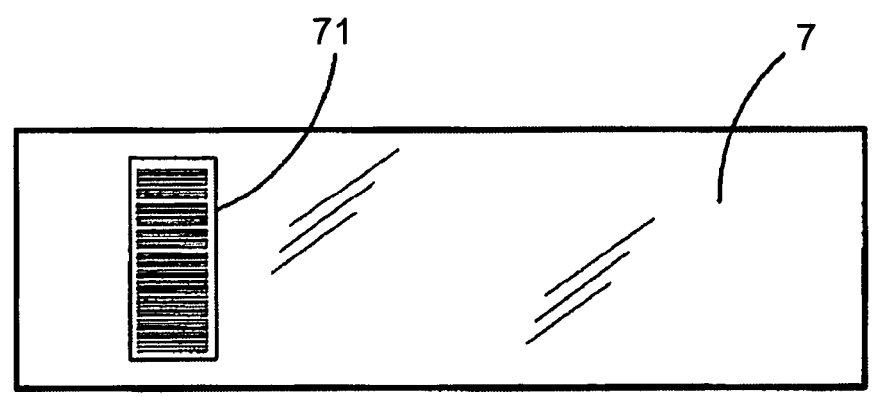
FIG. 22 is an example of a third kind of optical identifying means on a slide.

In FIGS. 20 to 22 various kinds of data encoded symbology for the label 71 (the entire label 71 as shown or only for the label area 72 (see FIG. 19)).

In FIG. 20, an example of a 2-D symbology of the Infoglyph™ type is shown. This may include perhaps even an information carpet type of symbology. This type of 2-D symbology is advantageous since it can carry a large amount of optically machine readable information. Making use of a high-resolution camera, this type of symbology may be readable in a high resolution and a large amount of information can be encoded therein. The symbology may be printed with tiny diagonal lines in different directions or perhaps even colors and can easily be read by a CCD camera or the like.

FIG. 21 shows an example of a data matrix code that can be used as an alternative to the Infoglyph™ symbology. The data matrix is similarly readable with a CCD camera but may not carry as many data in the encoding as the Infoglyph™. However, it is easier to print as it may have a less high resolution making it a simple and cost effective solution if less identification data on the slides and the reagent bottles is required. A yet simpler solution is shown in FIG. 22, where the symbology is a conventional bar code. In principle, this means that only a bar code scanner is required for reading the slides and the reagent bottle information, but by using a 2-D sensor, the possibility of self-calibration and monitoring the installation of slides and reagents in the staining apparatus may be enhanced.

In an embodiment, the optical identifiers on the slides and on the reagent bottles are the same type. This may facilitate the image processing of the identification process in the staining apparatus.

Figure 23:
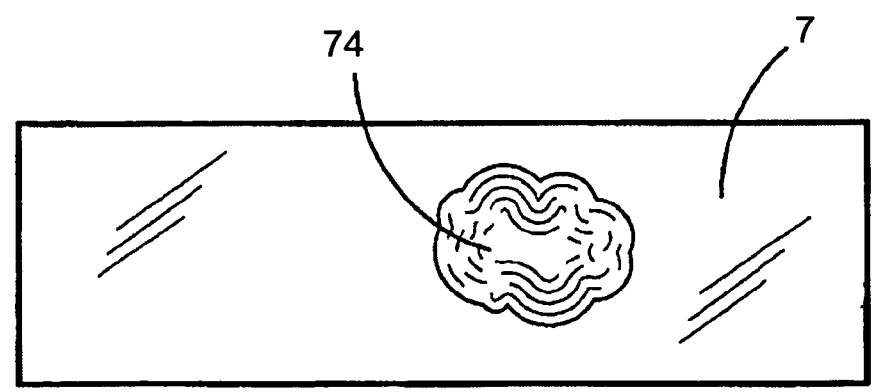
FIG. 23 is an example of a fourth kind of optical identifying means on a slide.

A different approach to identifying the individual slides or as a way of facilitating the new capabilities of confirming identification or storing confirmatory information may be to record the contour and/or the texture of the tissue sample 74 itself, such as shown in FIG. 23. Utilizing the high-resolution of the image that can be recorded by the camera, the unique features of the tissue sample itself can be used as a graphical identifier of the slide. Furthermore, an image of the stained tissue sample can be recorded so that a digital representation of the tissue sample is produced. This digital image can be sent electronically to remote locations for instant examination and/or archived for later examination. This may provide the staining apparatus with a unique flexibility in use and may introduce new and advantageous methods of analyzing the tissue samples.

Besides identifying the microscope slides and the reagent bottles in the staining apparatus, the 2-D optical sensor can also be used for self-calibration of the apparatus, e.g. after maintenance, if the apparatus has been disassembled or moved to another location. By identifying critical locations within the apparatus by capturing an image by the camera, the image processing software can compare the captured image with a reference image to determine if certain critical components in the apparatus are off-set from their predetermined positions, e.g. if a slide rack or a slide is slightly off-set, and if so, a set of correction data for the robotic motion control system may be calculated and this set of data may be used for calibrating the apparatus.

Figure 30:
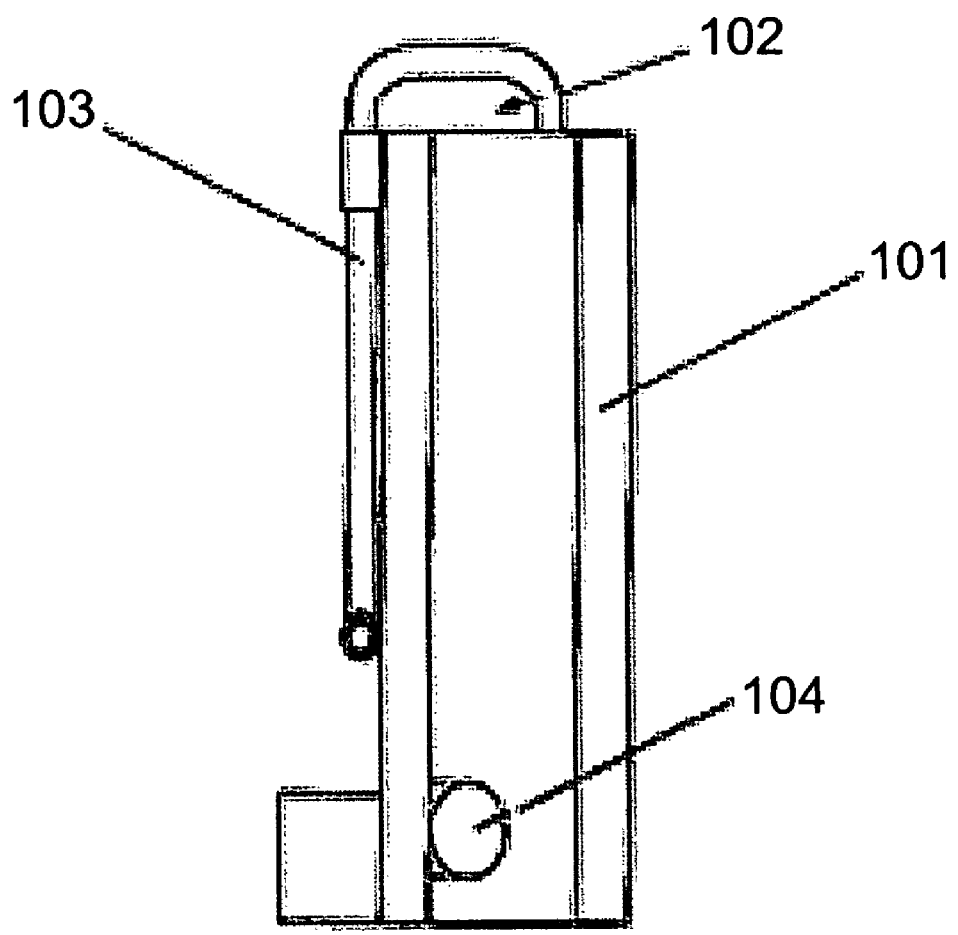
FIG. 30 is a front view of the processing tank of FIG. 29.

The discussion is now directed to the drawer assemblies and the components therein. A perspective view of a preferred embodiment of a drawer assembly 100 is shown in FIG. 28 and a side elevation view is provided in FIG. 24. Other perspective views of drawer assemblies are provided in FIGS. 25 and 26. The slide rack assembly 6 component of the drawer assembly 100 is shown in FIG. 27 and the processing tank 101 component is shown in FIGS. 29 and 30. The drawer assembly may comprise a slide rack, module, and/or magazines. It may be observed from FIG. 24 that the slides 7 (or, more generally, sample carriers) in the slide rack 6 are loaded and unloaded in a horizontal position when the slide rack is in an upper position. The slide rack is arranged in a slide elevator 63 and the slide holder 62 is adapted to pivot the slide 7 between a horizontal position and a vertical position 7v, when the slide rack 6 is in its upper position. The slide rack and the slide rack elevator 63 are arranged as a moving part 100a of a drawer assembly 100. In a corresponding stationary part 100b, or slide staining platform portion, of the drawer assembly 100, a processing tank 101 is provided.

Figure 32:
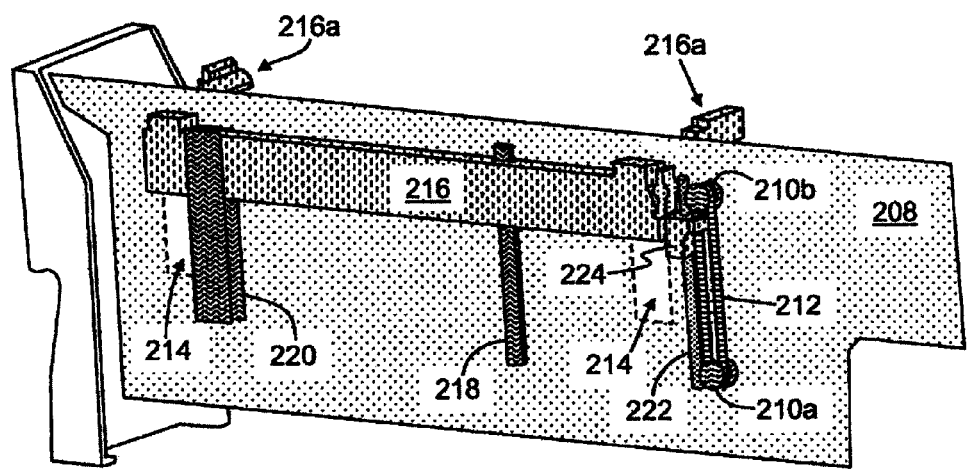
FIG. 32 is a detailed view of the slide rack elevator of FIG. 24.

A detailed view of the slide rack elevator 63 is provided in FIG. 32. The slide rack elevator mechanism moves any slides that are loaded into the slide rack up and down, either into and out of the processing tank 101, or up and down into the slide staining platform position. Only those slides within a slide rack that have previously been flipped into a vertical position will be lowered into the processing tank 101. Slides that are in a horizontal position will be lowered, by slide rack elevator 63, onto the slide staining platform so as to possibly come to rest upon the top surface of a temperature control member 64 within the non-moveable portion 100b of a drawer assembly 100 (FIG. 26).

The slide rack elevator components are mounted onto a side panel 208 of the moving part portion 100a of a drawer assembly 100. These slide rack elevator components comprise a stepper motor (on opposite side of panel 208 from the viewing position and therefore not shown) a first pulley 210a that is driven by the stepper motor, an elevator belt 212 that engages with the first pulley 210a, a second pulley 210b with which the elevator belt also engages, a clamp 224 secured to and moving with the elevator belt 212 and an elevator bar 216 attached to the clamp 224. The clamp 224 travels or rides along or upon an alignment post 222 that passes through clamp 224 and constrains the motion of clamp 224 to within one dimension (i.e., vertical). The elevator bar has, attached to it, two elevator arms 216a that pass through slots 214 in the panel and that mate with and support a slide rack 61 (not shown in FIG. 32; see FIG. 27), the slide rack being disposed at the opposite side of the panel 208 from the viewing position of the drawing. The elevator bar is constrained to move in one dimension (i.e., vertically) by alignment guides such as rail 218 and rail 220. Using the elevator mechanism shown in FIG. 32, motion of the stepper motor drives mechanical motion of belt 212 which drives vertical motion of clamp 224, elevator bar 216, elevator arms 216a and, ultimately the slide rack supported by elevator arms 216a.

In a preferred embodiment of the present invention, an apparatus preferably comprises eight drawer assemblies 100, as shown in FIG. 1. However, it is realized that any other number may also be provided depending on the design preferences. Each drawer assembly 100 includes (FIG. 24) a drawer slide, a slide rack elevator 63, a slide rack assembly 6 including slide temperature control members 64 which are, preferably, platforms having thermo-electric modules, a processing tank 101, a drip tray 65 for collecting staining fluids and control means including indicators for various user information and process surveillance purposes.

The slide rack assembly 6 is shown in FIG. 27. The slide rack assembly 6 includes a slide rack 61 preferably with a capacity of eight slides 7 in individual slide receiving compartments 68, as shown in FIG. 27. In connection with each compartment 68, a slide holder 62 is provided. The slide holders 62 include pivoting means including slide holder clips 69 which are pivotable between a horizontal slide position and a vertical slide position and activation means 67. The slides 7, 7v are individually pivotable in their slide holders 62, as the slide holder clips 69 may be pivoted by a pushing, via push tool 38 (FIG. 7A), of surfaces accessible through access holes 67 in slide rack 61 (FIG. 27), of which two are provided, one for pivoting from a horizontal to a vertical position and one for returning the slide from a vertical to a horizontal position.

Figure 33:
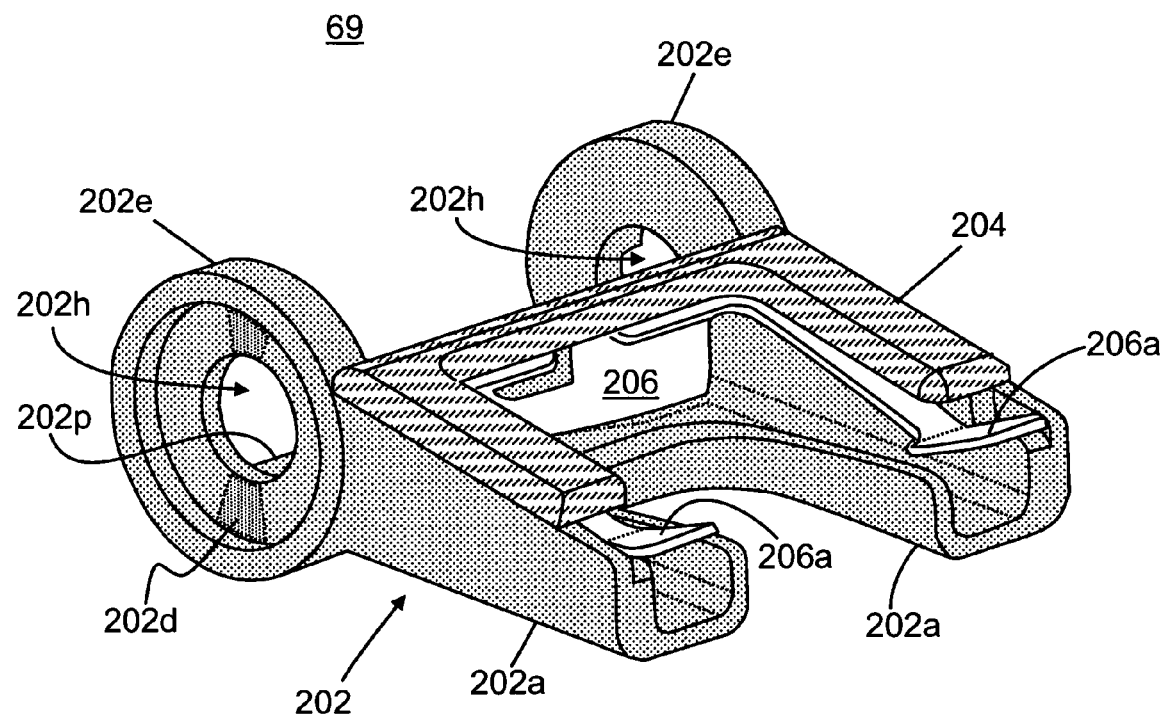
FIG. 33 is a detailed view of a slide holder clip as utilized within an embodiment in accordance the present invention.
Figure 34A:
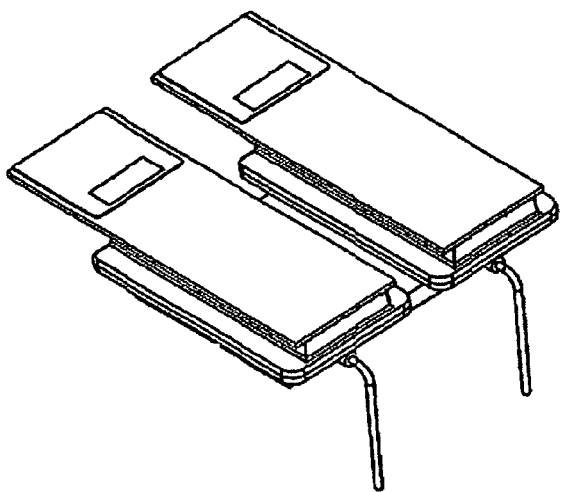
FIGS. 34 A-B are views of embodiments of temperature control aspects of one embodiment of the invention.
Figure 34B:
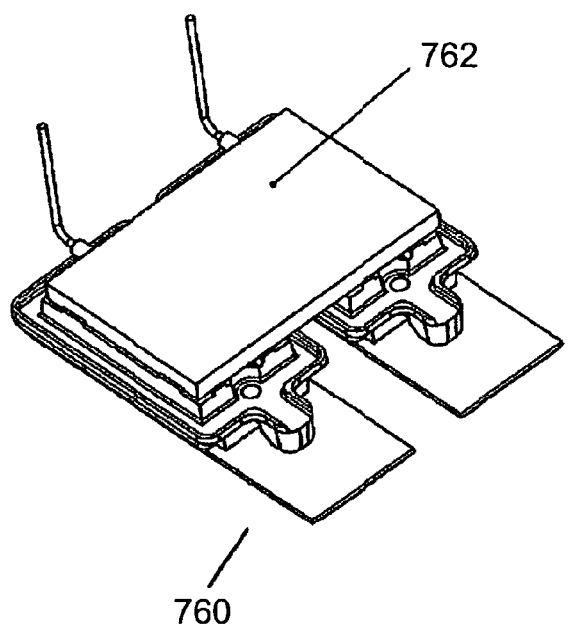

FIG. 33 provides a detailed view of a preferred slide holder clip 69 for use within an apparatus in accordance with an embodiment the present invention. The slide holder clip 69 (FIG. 33) comprises a lower body member 202 having two front-facing arm portions 202a, a rear ledge portion 202p and two rearward disposed disc-shaped flange portions 202e having circular holes 202h therein. The slide clip holder 69 further comprises a spring clip 206 and an upper retainer portion 204 physically coupled to the lower body member 202 and retaining the spring in place against the lower body member. The spring clip has two arms 206a that are respectively disposed above each of the two arm portions 202a of the lower body member 202. Each arm 206a of the spring clip 206 has a sharp crease or bend which is the lowermost portion of each arm 206a.

A slide (not shown) may be inserted between the arms 202a and the spring clip arms 206a (FIG. 33), after which insertion the slide will be snugly held within the slide holder clip 69. Preferably and importantly, the shape of the arms 202a and the spring clip arms 206a provide for a small free pivoting motion of a slide that is retained within the slide holder clip 69, the pivot point being just below the sharp bends in the spring clip arms 206a, which are the only contact zones between the spring clip arms 206a and the slide. This free pivoting motion of a retained slide permits the slide to precisely conform to the plane of the top surface of a respective temperature control member 64 within the non-moveable portion 100b of a drawer assembly 100. Without the ability to pivot into position in this fashion, the slide might not rest properly upon the temperature control member and might, consequently, be exposed to undesirable temperature gradients during a staining protocol.

The rear flange portions 202e of the slide holder clip 69 (FIG. 33) have holes 202h passing therethrough for mounting onto a support rod (not shown) that passes through corresponding holes in the rear portion of a slide rack. The entire slide holder clip 69 is able to rotate about the support bar passing through holes 202h so as to assume one of only two mechanically stable positions—a horizontal position as shown in FIG. 33 (corresponding to slides 7 in FIG. 24 and FIGS. 27-28) or, alternatively a vertical position (e.g., see slides 7v FIG. 24 and FIGS. 27-28). A plurality of detents 202d in the flange portions 202e assure that the slide holder clip 69 position will be held mechanically stable in only the two aforementioned positions.

The rotational motion of the slide holder clip 69 between the two stable positions (i.e., vertical and horizontal) is actuated by a push tool 38 (FIG. 7A), comprising an automated vertically moveable pin or bar (not shown) mounted on robotic head 22 that may access surfaces of slide holder clip 69 through access holes 67 in the slide rack 61 (FIG. 27) within which the slide holder clip is housed. Two access holes are associated with each slide holder clip. When the slide is held in a horizontal position, insertion of the push tool through the front-most access hole of each pair will cause the push tool to contact a top surface of retainer 204 (FIG. 33) such that further downward motion of the push tool against said surface will cause the slide holder clip 69 to lock into its vertical position. When the slide is held in a vertical position, insertion of the push tool through the rear-most access hole of each pair will cause the push tool to contact the ledge portion 202p of the lower body member 202 (FIG. 33), the ledge facing upward in this configuration, and further downward motion of the push tool against the ledge 202p will cause the slide holder clip 69 to lock into its horizontal position.

The slide rack is in an upper position when the drawer 100 is loaded with one or more slides 7 and also during the staining process. After the slides 7 have been loaded, the slides 7 may be pivoted to a vertical position 7v and then the slide rack 61 is lowered by the slide elevator 63, such that the vertically disposed slides 7v are immersed into the underlying processing tank 101. The drawer assembly is also shown in the FIGS. 25, 26 and 28. The slide elevator 63 may be adapted to agitate the slides 7v while they are immersed in the tank fluid.

Figure 31:
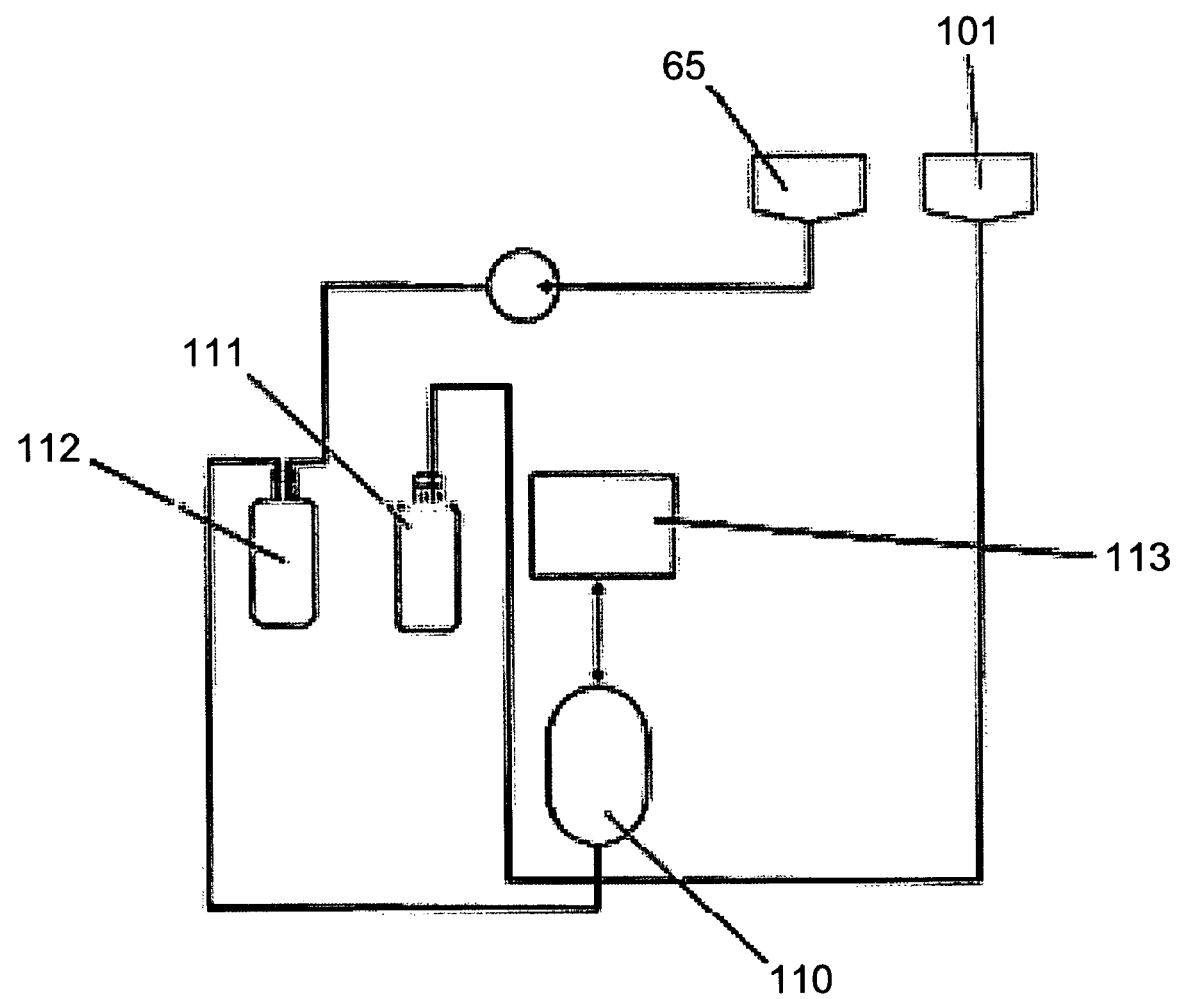
FIG. 31 is a fluidic diagram of the handling of processing liquid for the processing tank.

The processing tank 101 is filled with a predetermined amount of a processing fluid from a transfer tank 110 (see FIG. 31). The relevant processing fluid has, prior to that, been transferred from a supply tank 111 to the transfer tank 110 via pneumatic pressure means. Using a transfer tank 110, and controlling the fluid transfer by a pneumatic system, including a vacuum pump 113, the pumping may be carried out without fluids coming into contact with pumping components. This is advantageous since the risk of residues of fluids in the components is hereby minimized.

A total of eight drawers are preferably provided. Accordingly, this means that eight processing tanks are also provided in the apparatus. Each processing tank 101 accommodates up to eight immersed slides 7v at the time. A primary function of the processing tank is to heat the fluid in the tank up from ambient temperature to a predetermined temperature, in a certain amount of time, e.g. 15 minutes and maintain the predetermined temperature, e.g. up to about 120° C. without any sign of boiling for a pre-treatment processing time, e.g. 10 to 20 minutes after the slides have been lowered into the processing tank. Typically the preferred temperature is in the interval from about 40° C. to about 120° C., as determined by the requested treatment. Very often the preferred temperature is in the interval from 80° C. to 100° C., and more preferable from 95° C. to 98° C. For some special treatments the preferred interval can be from 110° C. to 130° C. and even up to about 150° C.

After this process time is passed, the heat is turned off and the slides 7v are removed by raising the slide rack 61 and thereby lifting the vertical slides 7v out of the processing tank 101. The tank 101 may be used for deparaffinization, re-hydration as well as heat induced target retrieval. These processes are performed onboard the apparatus with the slides in a vertical orientation, immersed in individual tanks that can be filled with and emptied of various required reagents. For the target retrieval process, the fluid level in the tank may raise onto the label on the slide. The heating member may be adapted to heat up and maintain a temperature of approx. 95° C. for a period of up to 40 to 60 minutes.

The pre-treatment process, carried out in the processing tank, may involve immersing the slides in a series of fluids for short periods of time, e.g. 5 to 10 minutes. The process of deparaffinization is intended to first remove from the tissue sample the paraffin in which it was mounted, and then remove the paraffin solvent, and then through a series of reagents progressively re-hydrate the sample. The process of target retrieval involves immersing the slides in a tank of heated buffer for incubation periods of 20 to 60 minutes. During this time the processing tank temperature must be maintained at a d temperature, preferably 95° C.±2° C. at sea level, when measured from top to bottom of the slide and must be maintained at this temperature during the duration of the process.

An automated sample processing system in accordance with embodiments of the present invention will control both the staining protocol as well as the pre-treatment, if any, administered to each slide, depending upon slide-specific information entered by the user. If the sample on a particular slide requires only de-paraffinization, but not target retrieval, then the following sequence of steps will be performed:

Step 1. flip slide to vertical position;
Step 2. lower slide into processing tank;
Step 3. supply processing tank with de-paraffinization reagent, in sequence according to de-paraffinization procedure;
Step 4. maintain slide in de-paraffinization reagent for required time;
Step 5. drain processing tank;
Step 6. repeat steps 3-5 for all reagents required in de-paraffinization procedure;
Step 7. supply water rinse to processing tank;
Step 8. drain rinse water from processing tank;
Step 9. raise slide out of processing tank;
Step 10. flip slide to horizontal position;
Step 11. run desired staining protocol for sample on slide.

If the sample requires only target retrieval, but not de-paraffinization, then the following sequence of steps will be performed:

Step 1. flip slide to vertical position;
Step 2. lower slide into processing tank;
Step 3. fill processing tank with buffer solution for target retrieval;
Step 4. heat buffer solution and immersed slide at desired temperature for desired time, according to target retrieval procedure;
Step 5. drain processing tank;
Step 6. supply water rinse to processing tank;
Step 7. drain rinse water from processing tank;
Step 8. raise slide out of processing tank;
Step 9. flip slide to horizontal position;
Step 10. run desired staining protocol for sample on slide.

If the sample requires both de-paraffinization and target retrieval, then the following sequence of steps will be performed:

Step 1. flip slide to vertical position;
Step 2. lower slide into processing tank;
Step 3. supply processing tank with de-paraffinization reagent, in sequence according to de-paraffinization procedure;
Step 4. maintain slide in de-paraffinization reagent for required time;
Step 5. drain processing tank;
Step 6. repeat steps 3-5 for all reagents required in de-paraffinization procedure;
Step 7. supply water rinse to processing tank;
Step 8. drain rinse water from processing tank;
Step 9. fill processing tank with buffer solution for target retrieval;
Step 10. heat buffer solution and immersed slide at desired temperature for desired time, according to target retrieval procedure;
Step 11. drain processing tank;
Step 12. raise slide out of processing tank;
Step 13. flip slide to horizontal position;
Step 14. run desired staining protocol for sample on slide.

As shown in, for instance, FIGS. 29 and 30, the processing tank 101 is elongated with an opening slot 102 through which the slides 7v may be inserted. This results in a relative small tank volume, which in turn allows for relatively rapid heating of the fluid in the tank and/or relatively low power consumption for heating up and maintaining the temperature of the fluid in the tank. The tank 101 is filled and drained via a fluid connection tube 103 and the heating member 104 is preferably located in the lower section of the tank. The tank 101 is moreover provided with insulating sidewall members on both sides to accelerate the heating thereby decreasing the heating times. The tank 101 is also provided with sensor means (not shown) for registering the fluid level in the tank and a sensor for registering the temperature of the fluid, and feeding these data to the control system of the apparatus.

The pre-treatment fluids or reagents may be stored in a number of individual containers, where some containers store fluids that are dedicated for deparaffinization, some for target retrieval and containers with 100% alcohol, distilled water and buffers. The containers are advantageously provided with different volumes corresponding to the required amounts of the specific fluids for the performance of the pre-treatment processes on the apparatus.

The fluid transfer between the supply containers 111 and the processing tanks 101 are via a transfer tank 110, as shown in FIG. 31. The fluid transfer is accomplished through positive and negative air pressure applied to the transfer tank 110. Preferably two separate, dedicated transfer tanks (not shown) are provided, one for aqueous solutions and a second for organic solutions. Similarly, for emptying the processing tanks, the waste fluid is transferred via the transfer tank 110 to the waste containers 112. Preferably dedicated waste tanks are provided, e.g. one for hazardous waste fluids and one for non-hazardous waste fluids.

Fluids may be transferred in both directions between any container and any tank. The operational sequence of the fluid transfers is determined by the control system of the apparatus. The deparaffinization reagents may be reused and periodically cycled from clean to dirty. Used dirty deparaffinization fluids and tank rinse fluids may be discarded by the user or by the control system as hazardous waste. Target retrieval buffer and water are labeled "single use" fluids in the control system and transferred to waste after use.

Preferably, the method according to the invention may include temporary storage of at least one biological sample on a slide in an appropriate liquid in the processing tank, for instance, after finishing the requested treatment until the biological sample on the slide can be removed for further off-instrument processing. Typically, this use of the processing tank is specifically advantageous in relation to an overnight staining, e.g. completed in the middle of the night.

Configurations of the temperature regulation system may include a Peltier device or Peltier temperature control, and in configurations such as shown in FIG. 35, a heat sink/fan pair 780a on the inside of the system's temperature-controlled interior volume. The other heat sink/fan of the pair 780b may be on the outside of the controlled volume, where it is exposed to the ambient environment of the laboratory. One or more thermoelectric devices (TED's) 781 perhaps including the electrical junctions themselves may be located on the boundary between the interior and exterior. The TED or TED's may generate a hot portion and a cold portion and may aid in moving heat into or out of the desired location. The "hot" portion may be configured to distribute heat from the exterior of the controlled interior volume. If the temperature of the "hot" portion of the TED is controlled to maintain a low temperature, such as with a controlled paired heat sink/fan, the corresponding "cold" portion of the TED, may be configured within the controlled interior volume, may be colder by a corresponding amount, and may act in conjunction with a paired heat sink/fan as a controlled refrigerator, and may even actively reduce the temperature of the interior volume, or may achieve protocol tolerances as further described below. Such an item may serve as a temperature reduction element for various locations or purposes as described below.

As mentioned above, the internal temperature of the system may be controlled by an adaptive sample processing control system. Some applications may provide temperatures at 24° C.+2° C.; in other embodiments the internal ambient temperature may be maintained at about 24° C. comprises+an incremental range, such as a non-integer incremental range. One temperature regulation system of the present invention may comprise one or more heat pumps, and in some preferred embodiments two thermoelectric heat pumps (heat pump 780 shown in FIGS. 35A and 35C). The temperature regulation system may feature each heat pump module having a heat sink and fan on either side of the TED.

Figure 36:
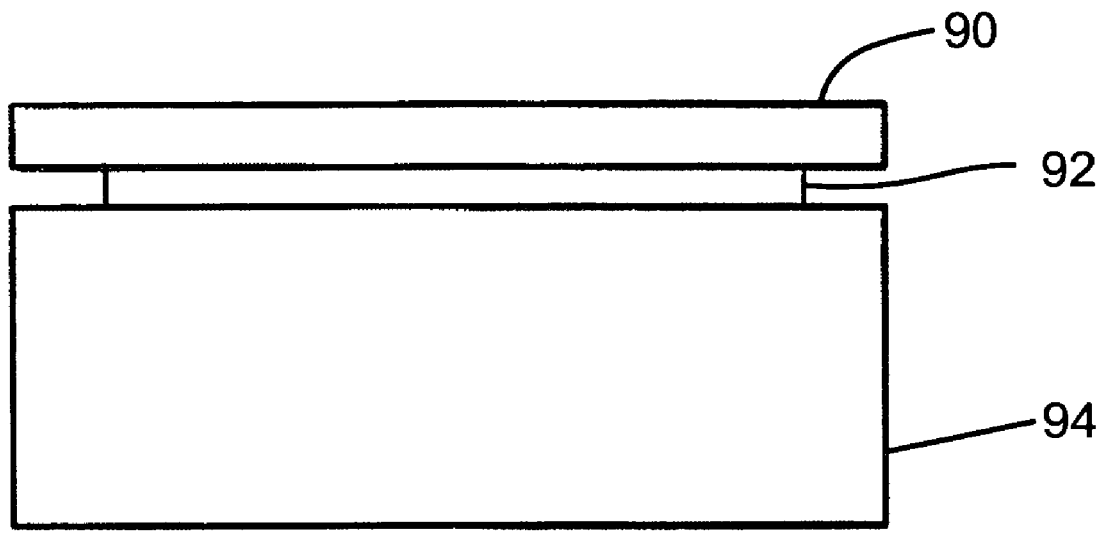
FIG. 36 is a block diagram of a temperature regulation design according to an embodiment of the invention.

Embodiments of the invention may comprise sample carrier temperature regulation systems, in some embodiments sample carrier temperature regulation systems configurable with one or a plurality of sample carrier supports, and corresponding methods of sample carrier temperature regulation. Some embodiments may comprise a Peltier grid, such as grid 760 shown in FIG. 34, that may be used as a component of or as a slide temperature control member 64 (FIGS. 24, 26), to heat or cool a slide during processing of the samples. Thermal elements 762 may heat the slides, in some embodiments from ambient to about 120° C. comprises in about 3 minutes. Sample carrier temperature regulation systems may comprise, in some embodiments, one or more sample carrier supports such as a slide support plate 90 as shown in FIG. 36, configured with temperature regulation elements, such as one or more temperature regulation elements, and in some embodiments a laminated thermal element 92 as shown in FIG. 36, and a cold plate 94 shown in FIG. 36.

The sample carrier temperature regulation system may reach target temperature even when ambient temperature is about or greater than target temperature, or about or less than target temperature.

Figure 37A:
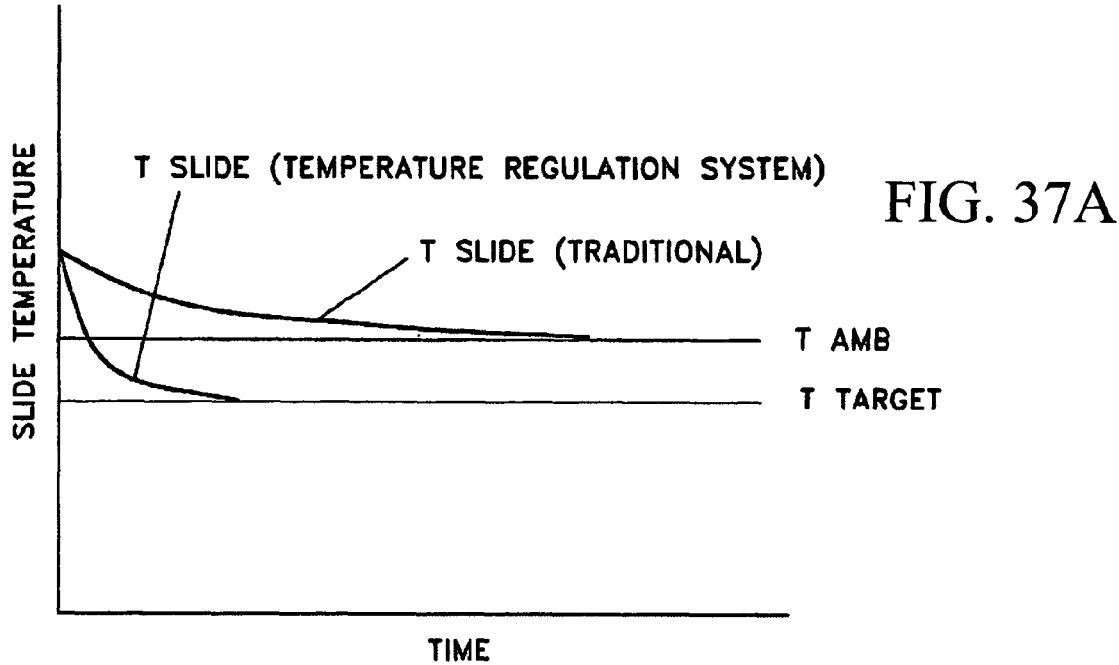
FIG. 37A is a comparison chart of exemplary temperature changes for an embodiment of the present invention and potential temperature changes of a traditional system in relation to a protocol temperature target, wherein ambient system and sample carrier temperatures may be initially above the protocol temperature target.
Figure 37B:
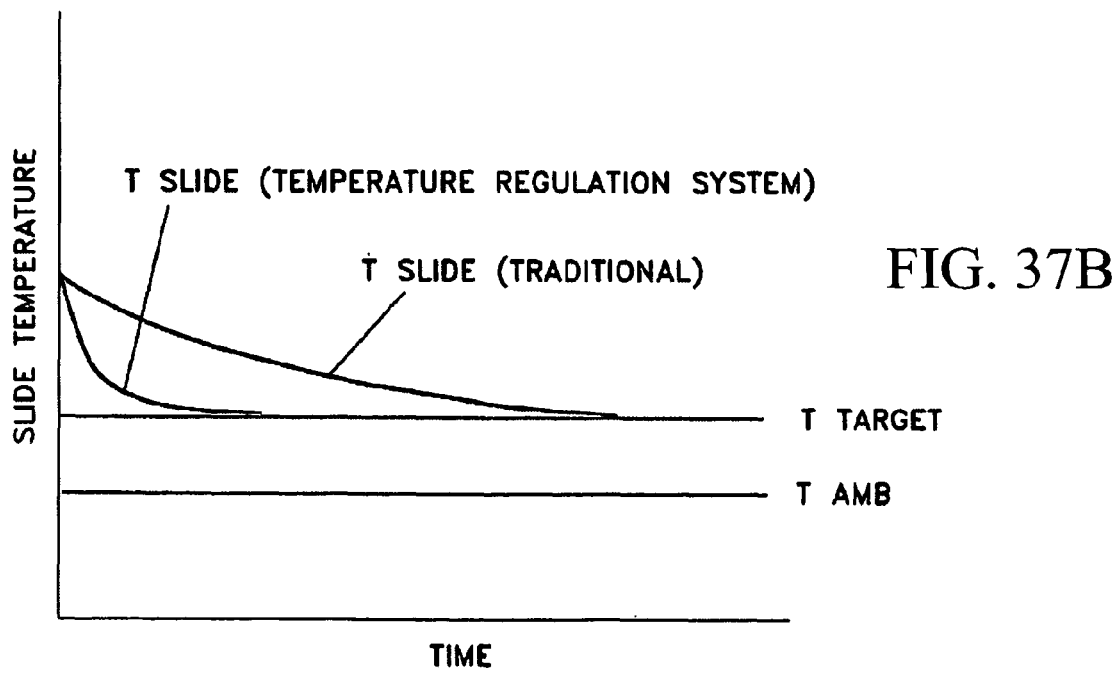
FIG. 37*b* is a comparison chart of exemplary temperature changes for an embodiment of the present invention and potential temperature changes of a traditional system in relation to a protocol temperature target, wherein sample carrier temperature may be initially above the protocol temperature target and ambient system temperature may be below the protocol temperature target.

The various embodiments of the disclosed temperature regulation system and the sample processing control system feature the capability to control system temperature, and in some embodiments, slide temperature and reagent temperature. The combination of features may allow active heating and cooling of sample carriers, and in some embodiments potentially utilizing a controlled Peltier device or temperature control, a conductive device or temperature control, or a combination of temperature control features. One preferred temperature control sequence may allow a controlled (e.g., adjustment or maintenance within a particular set parameters such as rate of change or the like) or even accelerated increase and/or decrease in slide temperature, perhaps including independently a ramping up and/or down of the temperature. The system may be considered as including a controlled temperature element or a controlled active temperature element, such as a controlled active temperature reduction element or the like. Another example of a controlled temperature sequence is shown in FIGS. 37A and 37B. These figures generally illustrate and compare temperature changes of the present invention and a type of traditional system. They illustrate target temperature tolerance, the time necessary to reach values, and ambient temperature aspects. In some embodiments, energy may be delivered at the same or about the same rate by the temperature regulation system as a traditional system. Energy may also, however, be removed or added, and perhaps even removed or added faster or slower than a traditional system, as traditional systems may dissipate energy to the ambient. A shorter or longer period for temperature effects, such as sample carrier cooling, may result. Active temperature regulation, in some embodiments heating and cooling, may be provided in some embodiments to provide such results.

In some embodiments, when a temperature disturbance greater than the target temperature occurs, such as by the effect of warm sample carriers, the present invention may rely on a conductive temperature regulation system, such as a substrate temperature regulation device, so as to dissipate excess energy, as previously described.

The temperature may be controlled within the required temperature tolerance for the sequence and controlled to maintain lesser values of rates of temperature change (dT/dt) during the sequence. The temperature range for a slide processed in accordance with conventional processing may exhibit greater values of rates of temperature change and may have temperatures beyond required tolerances for a significant portion of a sequence. As a result, the uncontrolled temperatures may be detrimental to the outcome for a protocol, such as the staining example previously described in relation to traditional technologies. An excessive low or high ambient temperature, and particularly an uncontrolled temperature, may cause a slower rate of temperature change and therefore may require a longer time to reach a desired temperature value as may be required by the protocol.

Figure 38:
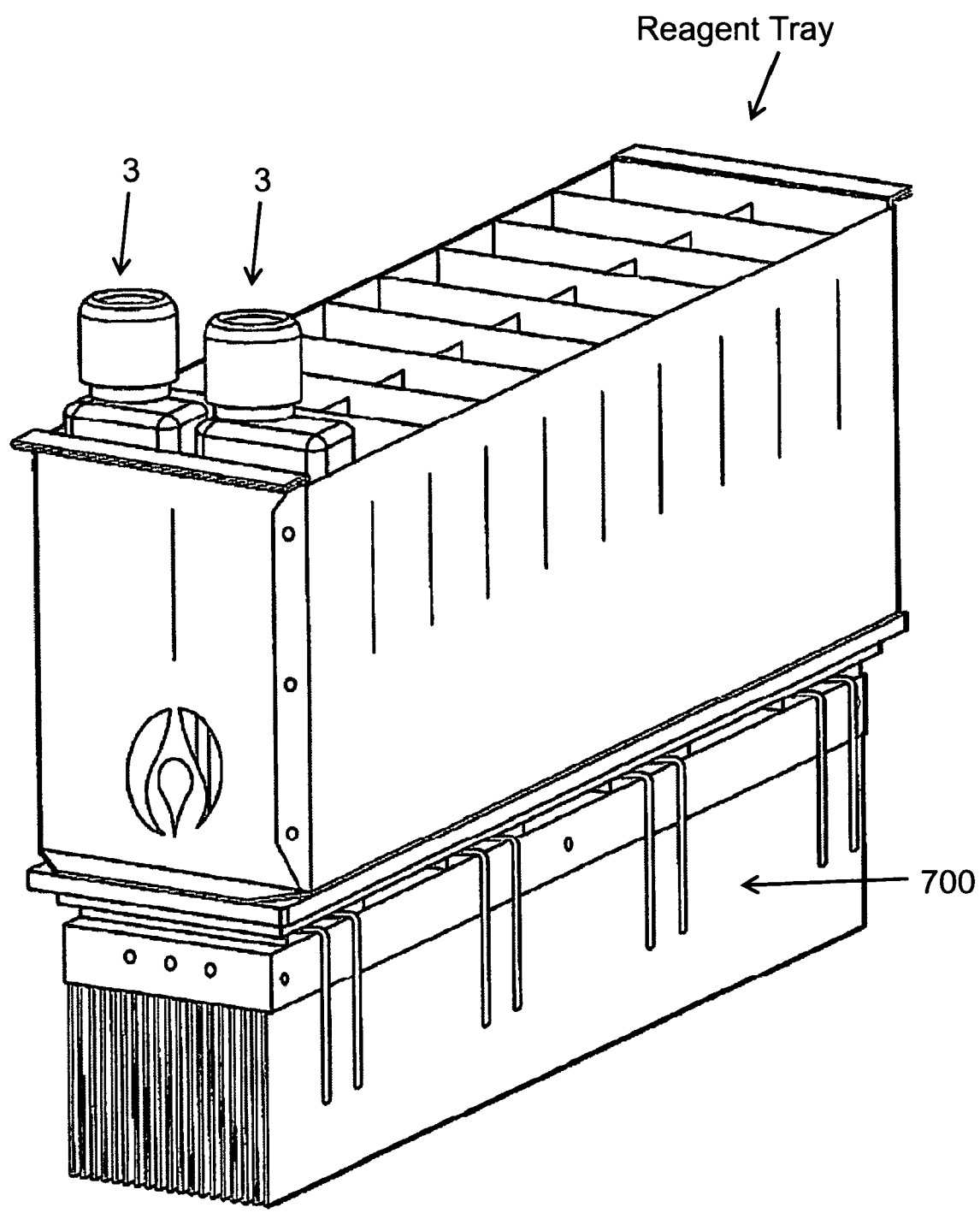
FIG. 38 is an isometric perspective view of an embodiment of reagent container temperature control aspects of an embodiment of the invention.

The various embodiments of the disclosed temperature regulation system may feature the capability of controlling reagent temperature alone or in addition to sample temperature. One embodiment of a reagent temperature regulation system is shown in FIG. 38 and may include a conduction temperature regulation system. A reagent temperature regulation system may have conductive regulation elements 700 perhaps mounted below the reagent tray. The conductive regulation elements may feature thermoelectric regulation features such as Peltier-type temperature regulation. Naturally, a sensing element may be provided as part of arm 20 or in another sample processing configuration, may be incorporated to sense temperature, perhaps instantaneously. This may assist in maintaining temperature tolerances and in controlling rates of temperature change. Photodiode devices, electric conductivity devices, IR sensors, sensors acting through septa of a container, or other sensors may be included to sense values such as reagent containers or slides collectively or individually.

Temperature control of the temperature regulation system may be provided to take advantage of the active heating and cooling capability of the above described temperature regulation system. Accordingly, in some embodiments temperature control may be provided to at least actively regulate temperature within protocol tolerances. The temperature regulation system of the present invention previously described may be accordingly configured to increase or reduce temperature, and in some embodiments actively increase or reduce temperature. The adaptive sample processing control system may provide a corresponding controlled increase or reduction of temperature, and in some embodiments actively controlled increase or reduction of temperature. It may also reduce the rate of an increase or decrease in temperature change (as compared to the often-used maximum power type of approach) such as by intermittently powering or lower powering the device or the like and may thus provide a reduced rate of temperature change element. Corresponding methods of the invention may comprise methods of temperature control of sample processing systems, comprising the step of regulating temperature within protocol tolerances, and in some embodiments, actively regulating temperature. Further methods of temperature control of sample processing systems are disclosed comprising one or more steps of actively increasing temperature, actively reducing temperature, or a combination of such steps.

As shown in FIG. 39, control of the processing samples may be accomplished with a sample processing system manager 500, such as a computer server connected with one or more sample processing systems. Connection among perhaps a number of process systems and perhaps a number of computers, such as workstations and a server (the latter residing either separately or as part of a workstation), may be achieved by use of a local area network (LAN), such as a group of computers and associated devices that share a common communications line or perhaps wireless link and may even share the resources of a single processor, memory, or server within a small geographic area (for example, within an office building or complex). Connection may also be established to a laboratory network, facilities intranet system, or even a laboratory information system such as through a bridge. Temperature values, historical actions, and particular timing activities may be captured and stored for local or remote access through the use of such a system.

Figure 40:
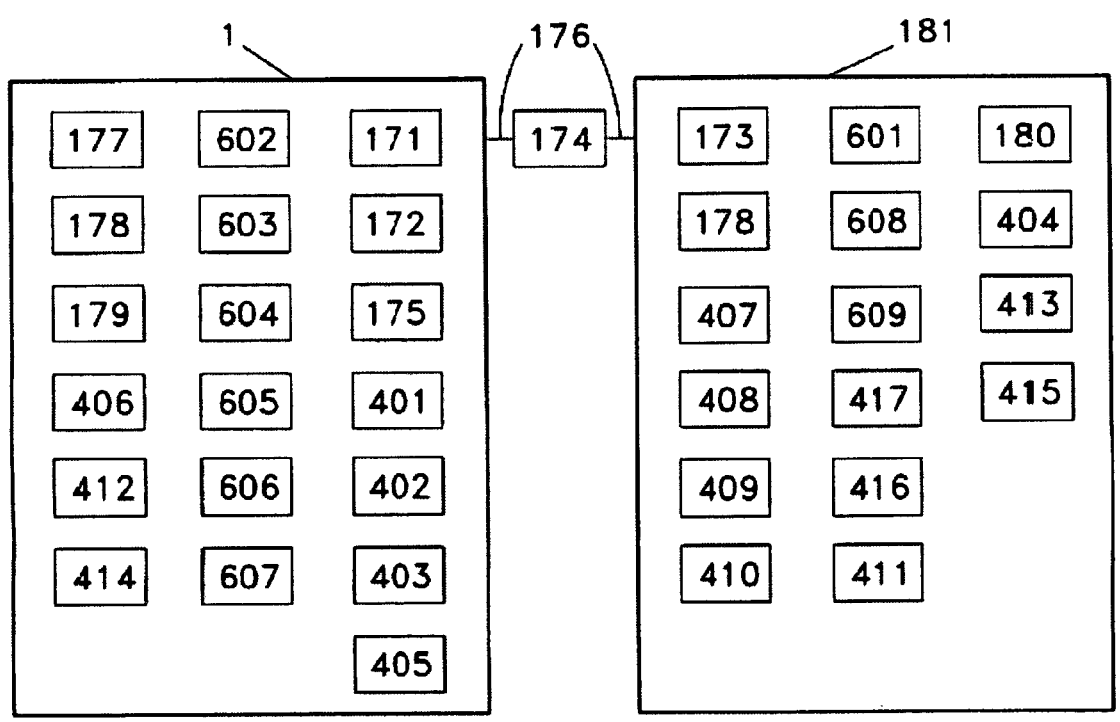
FIG. 40 is a block diagram showing some of the internal software features.

Aspects of the adaptive sample processing control system will now be discussed. The sample processing system 101 is configured to achieve an appropriate sequence of events that achieves a desired result to some degree. In achieving this sequence in an automated fashion to some degree the sample processing system is deemed an automated sample processing system and achieves automatic processing of at least one sample. This automated sequence as well as other aspects of the invention may be controlled by hardware, software, or some combination of them to accomplish a desired sequence with limited human intervention. Regardless how achieved, the automated control may be provided by a process operation control system 171 to direct the various activities. As shown in FIG. 40, this (as well as other functionalities discussed) may be software programming or subroutines; again, it may also include hardware or the like. In processing a slide, the automated sample processing system may serve as an automated slide processing system.

The automated sequence may involve a significant number of steps. In fact each process can itself require many automated movements to achieve its goal. Each of these type of operations or actions may be relevant to understanding an instrument's operation. Further, each of these types of operations or even a lesser set of significant events may be considered important details of the sample process operation. As explained later, it may be valuable to capture information relative to a significant number of these actions such as all of these operations, some subset of these operations, one-half of these operations, one-third of these operations, or the like. Further, even the nature or type of the events that may be of interest may be varied. In general, any event that may indicate the propriety of operation or processing may be a subject. Naturally in order to achieve automated processing it will be necessary to schedule the various sample process or process operations desired. This can be achieved by an item of software or the like that acts as a multiple event scheduler 401. In accordance with the desire for an automated processing system, embodiments of the present invention may include robotic sample process functions or a robotic motion system 172 responsive to the process operation control system 171 to achieve the desired operation steps.

As mentioned above, there may be a large number of process steps accomplished. As may also be appreciated from the nature of the processes envisioned, there may be uses of many different substances or the like. Whether involving a substance or merely a physical action, these types of items may be considered as relating to operationally influential exteriorly-consequential information. The item may be operationally-influential in that it either its operation or failure in operation may directly or indirectly influence some type of conduct. This conduct may be exteriorly-consequential in that it may be a conduct that does not take place within the process system itself but external to it. As such the present invention may provide the capability to monitor that information. This capability may even be considered as an operationally-influential exteriorly-consequential information monitor 402 as shown generally in FIG. 40. Thus the present invention may include an ability to monitor information of a broad nature.

Returning to the aspect of monitoring or capturing information, an embodiment of the system may be designed to monitor replenishable supply information, such as the status of buffers, reagents, stains or the like. By monitoring for a potential need for replenishable supplies the system may not only provide the replenishable supply information monitor 403 shown in FIG. 40, but it may also relieve operators of some concerns. It may also remove at least one possibility for human error. Significantly, the system may also act to automatically notify any number of people relative to the information monitored. With respect to replenishable supply information, the system may notify a user, an operator, an administrator, or even a supplier of an actual, potential, or impending need to replenish supplies. As such the system may be considered as including an automatic notice element 404, or an automatic operator replenishable supply notice element, an automatic supplier replenishable supply notice element, or the like.

In a similar fashion, an embodiment of the system may monitor or capture information that is of interest to the continued or continuous operation of the device. As such it may be monitoring instrument maintenance information. This may include, but is not limited to monitoring part cycle information, ranging from a gross information such as age of the device, estimated number of cycles, to even monitoring specific information such as monitoring individual part cycle information (e.g., how many times and actual valve was turned on or off, etc). By including an instrument maintenance monitor, an instrument maintenance information monitor 405, a part cycle monitor, or an individual part cycle monitor 406, the system may facilitate not only enhanced reliability and continuous operation, but it may permit preventative maintenance such as maintenance based on product cycles or mean times between failures. Naturally, it may also use the automatic notice element 404 such as providing an automatic maintenance notice element to inform a wide range of persons of such issues.

Of course, a large variety of information may be monitored; embodiments of the system may monitor or capture information that relates to material requirements, such as expiration dates, lot information or the like. Thus the present invention may include a material requirement information monitor 407 so that it acts to automatically monitor material requirement information. This may be a product expiration information monitor 408 that may even act with respect to an upcoming expiration and may even cause the set of automatically advance notifying a person by providing an automatic advance expiration notice element. For items that may be very important there may even be multiple notices either concurrently or sequentially and as such the system may include a multiple advance expiration notice element. Another type of information that may be monitored is historical usage information such as information of a statistical or past nature. Thus the system may include an historical usage information monitor 409. From this, predictive estimates may even be made such as a likely date upon which to order an item or the like. Through monitoring predictive usage information, this may be one way the system may be able to provide an automatic predictive need notice element or even a predictive usage information element 410. It may also provide for a user statistical information monitor so that it can assemble and monitoring user statistical information and act on this such as by comparing to other historical or statistical information or the like. The present invention may also be configured to monitor sample process efficacy information such as by assuring particular protocols are followed or the like and may thus provide a process efficacy information monitor 411. Monitored information may be extrapolated to permit a totalizator 413 capability by adding up individual usages to know amounts left or otherwise impacted by operation. This may include totalizing usage information for an item such as a reagent or an individual part's cycles. Such a capability may serve as a totalization usage information monitor, a reagent totalizator, or a part cycle totalizator. The system may also report cost per test and other such synoptic information that may be important to the economics and efficiency of instrument operation from a practical perspective. By having a data capture element 414, the system may generate data that may include or permit analysis or use of a variety of aspects, including but not limited to: number of occurrence data, part operation data, amount of usage data, and amount of material used data. Such data may, of course, have a like element, perhaps a subroutine, to do or generate the various function or data involved.

The automatic processing may be achieved by designing a system with automated process operation capability or sequencing through at least some steps without human intervention. This may be controlled by or act in response to a process operation control system 171. This may be provided through hardware, software, or some combination of the two. One conceptual embodiment depicts some of the various capabilities in FIG. 40. Of course, the user needs the ability to specify the nature and sequence of the various steps or acts desired or even the appropriate priority or other scheduling parameters to be used. This can be accomplished by an input parameter capability 173 through the inclusion of even a sample process parameter input 173. Input can be retained by the creation of stored parameter process data 174 so that the system can achieve the aggregate or perhaps plurality of process operations desired and thus the input may be an aggregated sample process input. In order to facilitate uninterrupted processing, the input parameter capability 173 may be configured as an independent process parameter input with respect to the process operation control system 171, such that acts caused by the process operation control system 171 are unaffected by any action with respect to the independent process parameter input. Further, the input parameter capability 173 may also be configured as an autonomous input functionality through the inclusion of an autonomous input element.

With the desired types of processing input, the system may act to automatically schedule the various events perhaps through a schedule element 605. These events may be considered as making up an aggregated event topology in that there is an aggregation of desired events and in that the events themselves present some topology or contour for a processing sequence. This topology may include only the events or it may include certain goals such as a particular prioritization or outcome desired. When using an initial input, the system may achieve scheduling of the events in the manner desired. Of practical importance may be the ability of an embodiment of the invention to permit and facilitate operator changes to the initial aggregated event topology. Significantly, these changes may be achieved dynamically, such as while other parts of the system are continuing processing. In facilitating changes while otherwise operating with little or no interruption, the system may act to achieve adaptive scheduling. This may begin as adaptive scheduling of an initial aggregated event topology and may evolve into adaptive scheduling of an altered aggregated event topology. This may occur on individual or perhaps stand alone devices, such as a stand alone stainer, or it may occur on an inter machine basis, such as by using an inter machine schedule indicium or an inter machine schedule element. Regardless, it should be understood that the scheduling of an altered topology may occur after commencing an initial automatic processing routine.

The alteration of the aggregated event topology may include any variety of actions that effectively alter an initial setup. These may include but are not limited to: altering the aggregate, such as perhaps adding a sample, deleting a sample, changing a sample, or altering the topology such as accepting a user change input such as merely a change in priority. They may also include accepting a temporary user change such a change that a user wants to see the effect of but may not wish to implement. Thus the system may include a sample addition element, a sample deletion element, more generally a sample change element 601, or a temporary user change element, each of which may be considered as creating some type of altered aggregated event topology. To permit a user decision embodiments may include functionality or subroutines for activating a user change or undoing a user change. These may be considered a user change activation element or a user change undo element. Such selection may be presented in conjunction with a results display element 602 of some sort such as an effect synopsis display element, a temporal impact display element (e.g., the time impact on one or more samples to be processed as a result of the alteration), and even an estimated temporal impact display element, whereby the time effect is only estimated.

As a result of some type of alteration in the aggregated event topology, the system may reschedule events. This rescheduled sequence may be used to interrupt or may provide an interrupt 603 relative to the initial sequence and to thereafter continue revised automatic processing according to the altered aggregated event topology. As can be understood, this may be accomplished without completing the initial automatic processing. The rescheduling may be programmed to achieve a variety of result and then to compare with is "best" depending on how the operator or system define that goal. Achieving a variety of results can be accomplished by simulating runs or perhaps a portion of a run and comparing the results of that simulation. The simulation may be of varied sequences set up according to certain parameters as explained below. By so doing, embodiments may include varied-parameter robotic control simulation functionalities 606, that is programming that simulates robotic operations based on differing parameters. These varied-parameter robotic control simulation functionalities 606 may be responsive to the aggregated sample process input by acting on the data the input creates. Specifically, the system may run multiple simulations for the same aggregated event topology with each simulation using different criteria to determine the sequence of steps. The results of these simulations may be indicium that can be used and compared. Comparison may be achieved by an automated process simulator comparator 604 which may look at any indicium resulting from the particular simulation being considered. From the indicium, a decision may be made and a particular set of parameters may be determined to cause an enhanced, if not optimum, sequence for a desired goal. These parameters may then be used in a preferred functionality robotic control generator 607 which may then actually create the sequence that is used for the desired process operation. In this fashion, the system may have a process generator that is responsive to the automated process simulator comparator and from which an automated process functionality may be created.

As mentioned, the simulations may take into consideration a variety of input for factors, including a user parameter input. Of course, there are a variety of parameters that may be considered as the rescheduled sequence is determined perhaps by comparing indicium (e.g., any value having information relative to that particular model) relative to a particular model. These may include but are not limited to: a substance priority parameter, a reagent grouping parameter, a robotic movement parameter, a sample location priority parameter, a sample proximity priority parameter, a sample insert time priority parameter, a user input parameter, a user priority parameter, a sample time since last processing priority parameter, a time-based priority value parameter, and a sample weighting parameter.

The system may compare the results, perhaps by software that may act as a comparator 604. The elements compared may be elements such as comparing processing time indicium, comparing completion time estimates, comparing substance cost estimates, or comparing sample priority assignments, and as such may be considered as having a robotic control simulation results comparator, a sample time since last processing priority parameter robotic control simulation functionality, a time-based priority value parameter robotic control simulation functionality, a substance priority parameter robotic control simulation functionality, a completion time estimate comparator, a substance cost estimate comparator, a sample priority assignment comparator, a repetitive process simulator comparator, and even a qualitative analysis comparator. As mentioned earlier, to facilitate some type of comparison, it may use indicium, such as an initial robotic control indicium and a second robotic control indicium.

In establishing a system that is practical, it may be advantageous to include—at least initially for calculations time concerns—a limited number of different simulations. For example, two or three may be included and may thus be considered a first control simulation functionality, a second control simulation functionality, and a third control simulation functionality. By establishing a system with a sample time since last processing priority parameter robotic control simulation functionality the system may assign a higher priority to samples that have not had any or perhaps particularly important activities for some time. By establishing a system with a robotic movement parameter robotic control simulation functionality it may take into consideration how far a robot needs to move to assign priority to items that require less movement. By establishing a system with a substance priority parameter robotic control simulation functionality, it may include consideration the fact that some substances are particularly concerning either because of cost, rinse needs, toxicity, or the like. Finally in making a comparison to determine which parameters yield a more desirable sequence, the system may include an enhanced temporal scheduler element so that the system automatically evaluates which parameters are likely to yield the fastest processing time. Naturally, this enhanced temporal scheduler element may be based on an total sample basis or may be based on some subset thereof. It may even be based on individual samples such as for a stat run or the like. Thus the robotic control simulation results comparator 604 may act to provide an enhanced rescheduling of an altered aggregate event topology. In implementing the revised sequence, the system may provide a seamless initial adaptive schedule functionality interrupt and may act to seamlessly, perhaps without perceptible discontinuity, interrupt the initial sequence and continue with the new one. Further, since the simulations may be time consuming, it is possible do only an initial comparison, perhaps such as merely comparing two differing functionalities, to then select one of them such as an initially preferred robotic control functionality and to then continue more simulations and comparisons. From this continued effort, there may be discovered an even better set of parameters and thus the system may thereafter implement a second preferred robotic control functionality as perhaps a better solution. Naturally continued simulations and comparisons may occur.

As may be understood by the above, rescheduling due to an altered aggregate event topology may be impacted by a number of factors. As but one example it may be understood in shortening time for overall processing, the location of a particular substance or a particular sample may be important; the further between samples or substances, the slower the processing. Because of this type of factor, it is possible that the system may actually consider, simulate or otherwise assess factors and may suggest actions that may yield desired results. For example, the system may display at least one suggested sample location, a suggested sample drawer location, a suggested stainer location, or the like. From this the user may be able to accept a proposed action and may even be able to accept or reject the suggestion. Thus the system may display a suggested user selection. This may even be the act of displaying a temporally enhanced suggested user selection through providing a user selection menu or the like. From this, the system may accept a user parameter input through a user selection menu. The results may even be summarized to display a synopsis of the effect due to the alteration, such as to display a temporal impact due to the alteration. Naturally, this may be estimated and the system may act to display an estimated temporal impact. Whether impact based or suggestion based, the system may provide the user valuable input and in this manner it may actually provide a suggested sample location element, a suggested sample drawer location element, a suggested stainer location element, a suggested user selection element, a temporally enhanced suggested user selection element, or the like. Naturally, such activities as well as any rescheduling or simulating may be the result of an operator request, the system sensing an operator access event, the system accepting a user change, or even some type of operator access event sensor, such as a drawer sensor or the like.

Similar to the act of suggesting to the operator a particular action that may enhance scheduling, the system may act to inform the operator of needed events or the like. If a particular substance is required but is not present in the machine (likely as sensed by the device itself perhaps through the optical sensor), the system may automatically prompt an operator for a particular action needed, such as insert the needed reagent or the like. In downtime or otherwise, the system may even repetitively automatically check if an operator action is needed. As such the system may include an automatic operator need prompt 608. It may also provide a variety of information such as real time status information, pending sample information, a real time completion estimate for an aspect (e.g., a sample, a drawer, a batch, or the like). Each of these may be accomplished by software and hardware perhaps by including a real time status information element, a pending sample information element, or a real time completion estimate element, each shown conceptually as the information element 609.

As to any of the above capabilities, such may not only act independent of the automated process operation capabilities, but where applicable, they may be fully functional even without the presence or operability of the automated process operation capability (which itself may or may not be in a process device). They may be achieved in a variety of manners, including by providing a separate full function computer 181 (e.g., separate from the capability provided or required by a process system) or that may be programmed to accomplish the desired function. In addition, in order to accomplish a goal of addressing practical and institutional needs, any capability may be configured to provide simplified use and may even be available in a highly simplified level of detail. This may be a "wizard" type of system where there is a "step-by-step" method for functions such as adding slides, achieving the desired input, or the like. Such an aspect may even be simple, regimented, and somewhat inflexible. A structured or simplified input can facilitate input by persons not required to have the full spectrum of skills necessary to be responsible for the operation of the sample processing system 1.

As part of the functions of monitoring or perhaps allowing play back of events, the system may include some type of data capture element 414. As may be appreciated from the initial discussion of the types of actions potentially needing to be programmed, the data capture element 414 may capture individual movement data, only robotic action data, individual robotic movement data, individual operation data, or even individual usage data. Thus the data capture element 414 may be an individual movement data capture element, a robotic action data capture element, an individual robotic movement data capture element, or an individual operation data capture element. All or any part of this data may be systematically stored such as storing all important details, only particularly important details (e.g., relative to highly sensitive valves, substances, or the like) or even only a significant number of details relative to sample process operations. Thus the data capture element 414 may be a systematic process detail capture element. Once captured, this data may be stored in a number of fashions. There may be a memory location at which such data resides and this may thus represent a significant process detail memory 412. It may also represent a subject sample data capture element and any of the memory types mentioned earlier may be used for such a purpose.

In storing the data, the system may create a segmented computer file, that is a file that contains only such data so that it is not as readily manipulated as other files. This may aid in assuring the accuracy or even certifiability of the events depicted. For instance for any particular sample, there may be automatically generated upon request a simulation—perhaps with a time base appended—of what happened to that particular sample as well as pictures of the sample before and after its processing. The data so stored may even be created as an inalterable computer record and perhaps may even include an integral change indicia that can prove its accuracy. When stored, the system may create a common format computer record so that user can easily work with it or it may create a proprietary format computer record that cannot be altered or the like. Thus the significant process detail memory 412 may represent a segmented computer file memory element, an inalterable computer record memory element, an integral change indicia memory element, a common format computer record memory element, or a proprietary format computer record memory element.

The capture of data may include time of occurrence data, such as actual date data, actual time data (e.g., UTC, etc.), precise time data (e.g., hours, minutes, seconds), relative time data, absolute time data, initiation time data, and even completion time data (e.g., process, protocol, motor operation events, or the like). Again, the data capture element 414 may include, but is not limited to, a time of occurrence data capture element, an actual date data capture element, an actual time data capture element, a precise time data capture element, a relative time data capture element, an absolute time data capture element, an initiation time data capture element, or a completion time data capture element.

One item that may be of particular user desire is the fact that the data capture element 414 may represent an individual sample process data capture element, an individual slide log data capture element, a type of protocol data capture element, and even an individual slide log data capture element. There may also be a real time individual slide log data display to show actual processing as it occurs.

Figure 41:
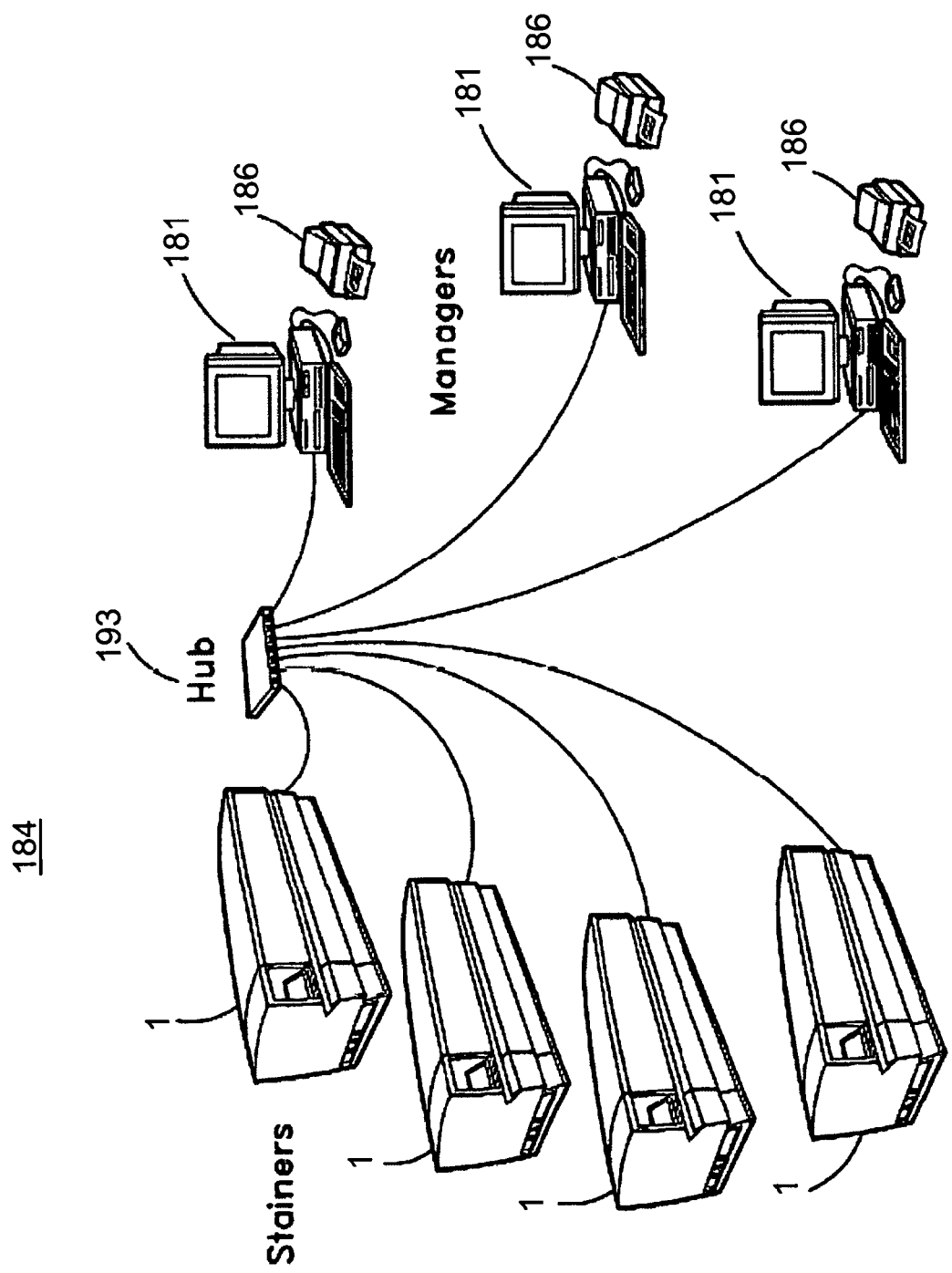
FIG. 41 is a depiction of an embodiment connecting multiple stainers with multiple managers and multiple label printers.
Figure 42:
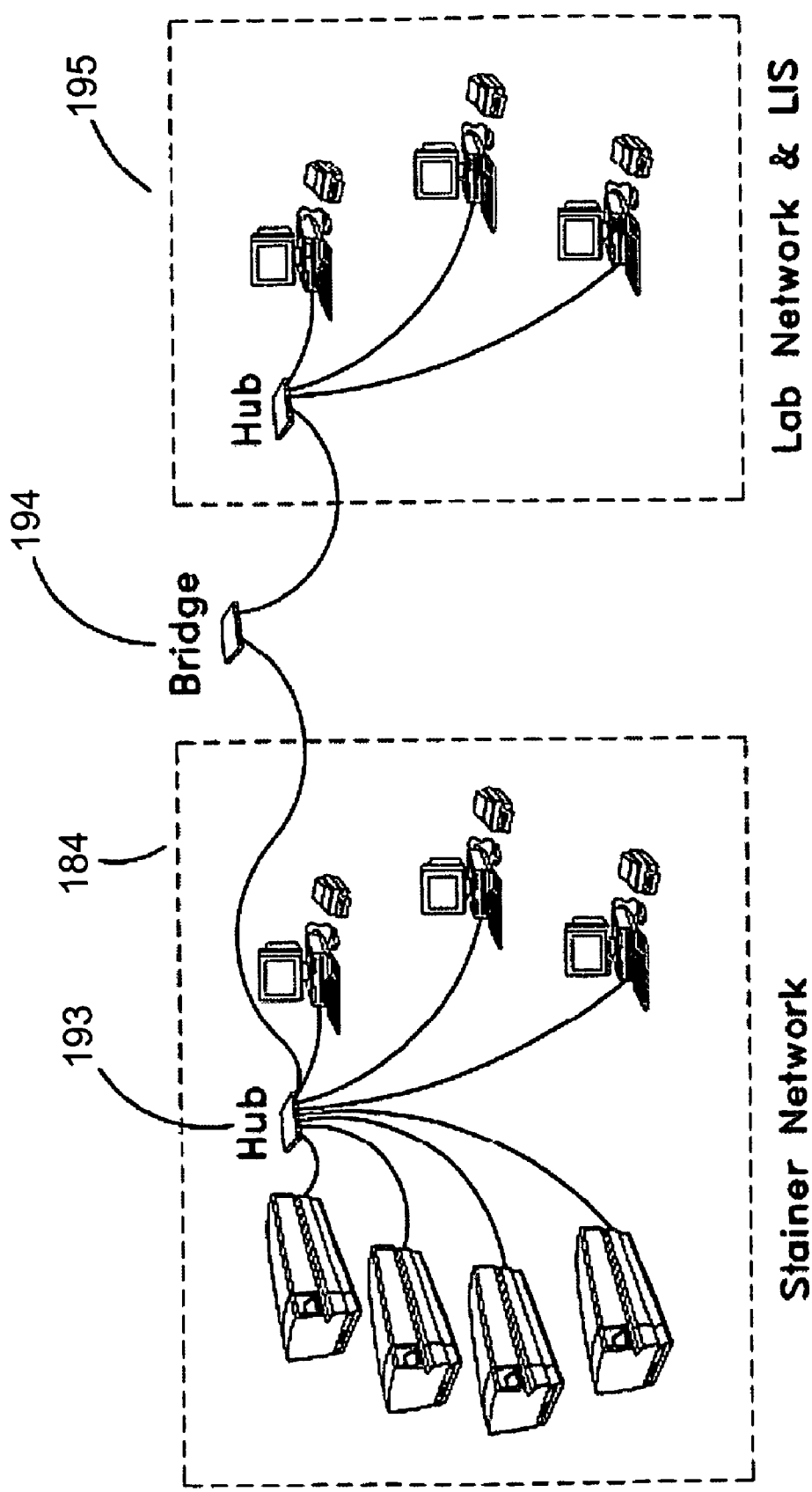
FIG. 42 is a depiction of an embodiment connecting a system to a lab network and lab information system.

As used above, the slide identification information may represent any information unique to a particular slide, such as a serial number, patient number, patient name, unique image, or the like. In keeping with privacy concerns, there may also be coded or perhaps encrypted identification information or internal identification information that others cannot use to identify the particular patient involved or the like. As discussed below and as shown in FIGS. 41 & 42, the overall system may include a number of staining instruments and thus the input can include preferred stainer information (which may or may not be indicated or accepted by the automated system). Provision can also be included to achieve a rush test and as such there may be an immediate, urgent, or otherwise known as stat (an often used medical term for immediate) process request information element. Such may also be linked with user privileges information so that only certain individuals may displace other tests to create a different priority. Of course all permutations and combinations of the above may be included.

For automated operation, the input may create data such as parameter process data 174 that may be stored at some location. To provide autonomous operation, it may be independently stored perhaps in a physically independent memory even at a location remote from an actual stainer itself. This may be accomplished by utilizing a primary or secondary storage perhaps of a separate full function computer programmed or configured to accept and/or store data. In such a fashion, the computer may contain what could be considered as an independent process parameter memory 174. Since the computer is likely physically separate, it may be considered to have a physically independent memory perhaps even a remote location memory if it is remote from the process equipment.

By using independent memory and independent other functionality, the system may facilitate full operational functionality of the automated process operation capability. Since the automated process operation capability is fully operational during operation of either the memory or input, the storing or inputting or other function can be conducted without interrupting the process operation. Thus the inputs can be later accessed at a process time independent of the time of accomplishing slide process parameter input or storing. In addition, entry or storing may also be accomplished at least in part concurrently with the processing of certain samples. This processing may even be initiated significantly after completion of the slide process parameter input action. Such may occur at least about one hour after the input, at least about three hours after the input, at least about eight hours after the input, at least about one day after the input, at least about two days after the input, and at least about one week after the input.

As mentioned briefly above, once the information is either monitored or captured, the present invention may act to automatically inform at least one person who may find the information useful. The automatic notice element 404 mentioned earlier may be configured to act as an automatic exteriorly-consequential information notice element by relating largely to that type of information. Of course, the automatic notice element 404 may act in response to the step of monitoring the particular information involved. For example, if it is monitoring operationally-altered outside information, the automatic notice element 404 may act as an automatic operationally-altered outside information notice element. For process events that are merely captured and not automatically monitored, a person may prompt the system upon which it may provide information by some type of display 415. This display (in its broadest sense) may reveal at least some information, perhaps relative to sample process operations to at least one person. If the display reveals significant process detail information, it may be considered as a significant process detail information display. Further if it displays at a separate location there may even be a significant process data transfer element to facilitate remotely displaying such information. As such the display 415 may be considered a remote process detail information display. As mentioned earlier, the system may provide for a real time information display, that is a display that reveals information at about the time it occurs. By real time displaying information remotely, the operator or any other interested person may be able to "watch or monitor the progress of the instrument from another location—perhaps even the other side of the world. This may be particularly valuable when there is a real time display of individual slide log data as mentioned above.

One type of display 415 that may be noteworthy is the fact that embodiments of the invention may create a simulated motion display. The simulation may visually show an element moving on a screen just as the robot head actually moved when it operated. Embodiments can provide sequential playback capability so that one could also "watch" the instrument just at it operated at some earlier time. There may also be an altered speed sequential playback capability, a user alterable speed sequential playback capability, or merely a high speed sequential playback capability perhaps all with or without pause or slow motion capability. With this capability, the display 415 may represent a simulated motion process detail information display. The system may thus include a sequential playback element, an altered speed sequential playback element, a user alterable speed sequential playback element, and a high speed sequential playback element.

All this information must, of course be used by some person. Any interested person may have the information available to them, such as an operator (e.g., anyone responsible for all or a portion of a process or the instrument), an instrument operator (e.g., an individual physically responsible for all or a portion of a process), an administrator (e.g., a person managing operators or perhaps responsible for order placement), a substance or other supplier, or even a manufacturer, such as for support and maintenance capability. For events that may require external actions (e.g., ordering more reagent or the like), the system may automatically notify at least one of these types of people and thus the automatic notice element 404 (such as a display which may be visual or otherwise) may be considered as representing an automatic operator notice element, an automatic administrator notice element, an automatic supplier notice element, or an automatic manufacturer notice element. It may also be considered as representing an automatic operator exteriorly-consequential information notice element, an automatic administrator exteriorly-consequential information notice element, an automatic supplier exteriorly-consequential information notice element, or an automatic manufacturer exteriorly-consequential information notice element.

Notice may be given at a variety of times. The system may act to automatically advance notify a person such as of an upcoming expiration date or of a need to reorder in advance. In so doing it may have or have input to it some type of lead time information that tells it how early to take the action. By properly configuring a lead time information data element 416, lead time may vary by location and situation, for example a machine around the world or used continuously for critical processing may have a longer lead time than a machine right next to a supplier or used only sporadically. Order lead time information, reagent order lead time information, maintenance lead time information (any of which may vary over the course of a year or from time to time) may be utilized and as such the lead time information data element 416 may represent an order lead time information data element, a reagent order lead time information data element, or a maintenance lead time information data element.

Notice itself may be displayed in a variety of ways. The system may automatically E-mail a person through inclusion of an E-mail notice element; it may automatically print out (including faxing) a notice by having an automatic printout notice element. Among other possibilities, it may automatically utilize a telephone line for simulated or reproduced voice or other information by having an automatic telephone line utilization element.

The actual event of providing notice may be automatic or it may by caused by some type of user prompt 417. By accepting a monitored information user prompt the system may represent a monitored information user prompt. The prompt itself may be a mere software selection or even a mere click-on items such as a software displayed button or the like. Whether displayed and acted upon remotely or at the actual robot-containing housing, such a user prompt 417 may cause a remote access connection to be established and as a result at least some significant process data may be displayed. In such a manner the user prompt may represent an information access prompt element, a software selection element, or a remote access element.

In some embodiments, the system may be comprised of independent or perhaps redundant slide staining modules (some embodiments may comprise eight modules) as shown for some embodiments in FIGS. 1 and 3. Throughput may be based on the time to first result with the system allowing access to completed slides as soon as a staining module has completed the scheduled staining tasks. The multiple independent or redundant staining modules may allow for both continuous and batch processing of slides. Additionally, each independent staining module may also allow for the independent pre-treatment and staining of each slide. A carrier retainment assembly, such as a slide retainment assembly, may be used to introduce slides to be processed into the drawer 104, the drawer, slide retainment assembly, and components thereof forming a stain module. The slides may occupy one or more positions of the slide retainment assembly, such as at carrier retention devices, up to the capacity of the slide retainment assembly with the potential for each slide being processed independently of other slides configured with the slide rack. Embodiments of the stain modules, drawers, slide racks, and components thereof are also shown in FIG. 3. FIG. 3 also provides other embodiments of system features, such as an embodiment of the arm 120 and the component features of the arm.

Slide retainment assemblies having one or more slides and even reagent containers may be introduced into the staining or reagent modules by introduction into drawers 104 one at a time or in any combination until all or an appropriate number of staining modules are appropriately occupied. There may be no restrictions as to the order, number or timing of when the slide retainment assemblies are introduced into the system, the system may also allow for adaptive scheduling of sample loading. Staining modules, and in some embodiments the drawers of the staining modules, may lock out access to the slides during the processing period and may release them to the operator upon completion of the staining or other process on the last slide of that module. In some embodiments, the order in which the slide retainment assemblies are released may be dependant on the time required to process the last slide of the retainment assembly. Slides may even be processed in the most time efficient manner independently of the order to which they were introduced into the system. The system may provide an optimum or merely an enhanced temporal scheduling of the various sample process steps. To accomplish this, the system may automatically schedule steps that are interspersed for an enhanced time result. This interspersing may be an interleaving of a number of process operations and even an interleaving of a number of individual sample operations. In addition to interleaving steps, the system may sequence the individual sample operations. Regardless as to how programmed, it may be configured through hardware or software or a combination of each to provide an enhanced temporal scheduler element 179, a process operations interleave element, an individual sample operations interleave element, or even an individual sample operations sequence element. These can be created by integrating the automated process operation capability and either the parameter data or perhaps some replicated portion of that parameter process data (as mentioned later) and can thus act to create an interspersial robotic control functionality 175.

Slide retainment assemblies having one or more slides may be introduced into the staining modules by introduction into drawers 104 one at a time or in any combination until all staining modules are occupied. There may be no restrictions as to the order, number or timing of when the slide retainment assemblies are introduced into the system, the system allowing for adaptive scheduling of sample loading. Staining modules, and in some embodiments the drawers of the staining modules, will lock out access to the slides during the processing period and may release them to the operator upon completion of the staining process on the last slide. In some embodiments, the order in which the slide retainment assemblies are released is dependant on the time required to process the last slide of the retainment assembly. Slides may be processed in the most time efficient manner independently of the order to which they were introduced into the system.

The control of the processing samples may be accomplished according to the following preferred embodiments, one preferred embodiment shown in FIG. 39, although other processing may be accomplished consistent with the present invention.

Control of the sample processing may be accomplished by a dynamic scheduling algorithm, and in preferred embodiments, in accordance with the continuous or batch processing previously described. The processing sequence may be controlled, in preferred embodiments, such that the various steps of a protocol for samples may be automated by one or more algorithmic controls. A preferred control may be accomplished as follows: 1) selecting a first protocol step, 2) selecting a second protocol from a restricted list of menu items that are compatible with the first protocol step, and 3) selecting subsequent protocol steps from a restricted list of menu items that are compatible with the preceding protocol step.

As shown in FIGS. 41 & 42, in expanded systems, a sample processing system manager, such as a computer server may be connected with a number of individual sample processing systems. These may represent automated slide stainers or even stand alone automated slide processing system such that they are fully capable of functioning with connection to other devices. In systems where a connection does exist, the capability of electronically connecting a number of automated slide stainers or automated sample processing systems or label printers 186, may be provided. As mentioned earlier, there may be one or more separate full function computers connected. These may be connected through a hub 193. There may be a multitasked central processing unit resource on either the stainer or the computer or there may be a number of central processing units that are configured to avoid using or implementing a multitasked central processing unit resource relative to the process operations in order to maintain full independence or perhaps even autonomous operation. The connection, whether for input or other operation may also be a remote link (including ability to be made remote such as in detachable memory) such as an internet connection element, a telephone line connection element, a wireless communication element, or even a detachable memory element. In a preferred embodiment, connection among perhaps a number of process systems and perhaps a number of computers, such as workstations and a server (the latter residing either separately or as part of a workstation), may be achieved by use of a local area network (LAN), such as a group of computers and associated devices that share a common communications line or perhaps wireless link and may even share the resources of a single processor, memory, or server within a small geographic area (for example, within an office building or complex). A local area network for this type of system may also include features such as but not limited to: an Ethernet element, a token ring element, an arcnet element, a fiber distributed data interface element, an industry specification protocol, a bluetooth-based element (named but not contemporary to King Harald Bluetooth of Denmark in the mid-tenth century!), a telecommunications industry specification using a frequency band of 2.45 GHz, a communication specification applying an IEEE 802 standard, a frequency hop communication specification, a shared common link element, a transmission control protocol/internet protocol communication element, a packetized information protocol, a shared protocol, a proprietary protocol, and even a layered protocol exchange system. By providing an electronic connection 176 between various resources, the local area network such as the stainer network 184 (a network dedicated to only the stainer or perhaps sample processing resources for integrity, security, and other purposes) in one embodiment may transmit a electronic memory address to achieve access to the appropriate information. Connection may also be established to a lab network, facilities intranet system, or even a lab information system 195 such as through a bridge 194.

As mentioned, connection may be accomplished over internet connections but more preferably is accomplished over local area network connections. Each sample processing system may be individually controlled, in some embodiments, by a PC attached with, internal to, or otherwise provided. Data sharing between sample processing systems and the system manager may be performed to allow identification, tracking, and status of sample batches, reagents, and other agents and components of the sample processing system. A determination of which system has which reagents, reagent type, slides and protocols may be performed. Log files for each processing sequence, protocol, or slide can be generated for monitoring processing status. Database maintenance (including but not limited to purge, compact, back-up, database list, and archive functions) and system diagnostics (including but not limited to exercising active system components to verify proper operation and assisting in troubleshooting efforts) may be accomplished manually or automatically.

The system may be configured to automatically access the required data through operation of the process operation control system 171 by inclusion of an automatic memory access element. This access may be achieved by specifying an electronic memory address that may be transmitted by a electronic memory address element 178 perhaps over a local area network and may be followed by automatically replicating that data on some a memory aspect appropriate for operation such as an automatic data replication memory. This memory may include but not be limited to: a volatile memory functionality as implemented by a volatile memory element, a random access memory functionality as implemented by a random access memory element, a non-volatile memory functionality as implemented by a non-volatile memory element, an electrically erasable programmable read only memory functionality as implemented by an electrically erasable programmable read only memory element, a main storage functionality as implemented by a main storage element, a secondary storage functionality as implemented by a secondary storage element, a cache memory functionality as implemented by a cache memory element, and even a detachable memory functionality as implemented by a detachable memory element.

A control interface may be provided for the operator, such as a graphical user interface (GUI), and may accommodate various languages. Help menus may be provided to assist in sample processing. Password protection features can be provided and even administrator control over at least some aspects. This may include the capability to include administrator limitations on the functional availability of any aspect of the system or of specific stainer availability or functionality, certain reagent availability functionality, certain protocol availability functionality, patient identification information access functionality, process priority request functionality, and immediate, urgent, or stat process request functionality. By including an administrator control element 180, the system may have an administrator-implemented user limitation element, a specific stainer availability limitation element, a certain reagent availability limitation element, a certain protocol availability limitation element, a patient identification information access limitation element, a process priority request limitation element, an immediate, urgent, or perhaps stat process request limitation element, a user privileges input element, and even a user group privileges configuration or input element.

Control of the sample processing may be accomplished by a dynamic scheduling algorithm, and in some embodiments, in accordance with continuous, or batch processing previously described. The processing sequence may be controlled, in preferred embodiments, such that the various steps of a protocol for samples may be automated by one or more algorithmic controls. As part of input to establish the desired control functionality, user or other input may be accommodated as follows: 1) selecting a first protocol step, 2) selecting a second protocol from a restricted list of menu items that are compatible with the first protocol step, and 3) selecting subsequent protocol steps from a restricted list of menu items that are compatible with the preceding protocol step.

After all data is input, the system may act to determine operational readiness by inclusion of an operational readiness determination element 177 that may be programmed to assess if appropriate resources, drawers, slides, reagents, or other aspects are present or available to the system. As mentioned above it may notify an operator of a need if any exists. Once an appropriate operational readiness is determined, the system may prompt initiation of access of the input data to electronically determine operational availability of a variety of items. These may include but are not limited to: an individual sample element through inclusion of an individual sample readiness determination element, a defined group of samples through inclusion of a defined group of samples readiness determination element, a physically grouped collection of samples through inclusion of a physically grouped collection of samples readiness determination element, a slide drawer component through inclusion of a slide drawer component readiness determination element, a stand alone automated slide processing system through inclusion of an stand alone automated slide processing system readiness determination element, a slide stainer system element through inclusion of a slide stainer system readiness determination element, and even a user initiated prompt signal such as might occur to force or activate the system manually by the inclusion of a user initiated prompt signal determination element.

There may even be timing tolerances, referred to in some embodiments as "bubble tolerance", that may be controlled as between steps, such as between aspiration cycles. Additional control may be accomplished through timing algorithms to determine time tolerances of components of the processing system, such as the monitoring of "shelf life" or viability of reagents. Furthermore, adaptive scheduling of sample and slide insertion and removal into the system, as previously described, may be accommodated on an ongoing basis throughout operation of the sample processing system.

An improved method and apparatus for pre-treatment of biological samples have been disclosed and have been described according to some preferred explanatory embodiments. Those skilled in the art can now appreciate, from the foregoing description, that the broad techniques of the embodiments of the present invention can be implemented in a variety of forms. Therefore, while the embodiments of this invention have been described in connection with particular examples thereof, the true scope of the embodiments of the present invention should not be so limited since many variations and equivalents of the method and the apparatus may be carried out without departing from the scope of the invention as specified in the accompanying claims.

What is claimed is:

1. An apparatus for automated processing of a plurality of biological samples on sample carriers having respective identifications, the processing of each sample being conducted according to a respective sequence of protocol steps, said apparatus comprising:
a frame;
a plurality of drawers within the frame, each drawer comprising a respective carrier rack for supporting at least one carrier; and
a robotic reagent dispensing head within the frame that performs ongoing robotic processing, including dispensing of reagents, according to the protocol steps; and
a sensor for reading the identifications,
wherein a first sample, in a first drawer, for which the processing is completed may be removed from the apparatus without interrupting the ongoing robotic processing of a second sample in a second drawer, and
wherein a second sample, in a second drawer, may be inserted into the apparatus without interrupting the dispensing of reagents onto a first sample, in a first drawer, with the robotic reagent dispensing head.

2. The apparatus of claim 1, further comprising a plurality of reagent containers within the frame, each reagent container containing a respective reagent for administration to the samples.

3. The apparatus of claim 2, wherein each reagent container has a respective reagent identification that may be read by the sensor.

4. The apparatus of claim 3, wherein the reagent identification comprises a two dimensional symbology.

5. The apparatus of claim 3, wherein the identification is in the form of a two-dimensional high-resolution symbology code.

6. The apparatus of claim 3, wherein the identification is in the form of a two dimensional data matrix.

7. The apparatus of claim 3, wherein the identification comprises human-readable text.

8. The apparatus of claim 2, wherein each reagent container is keyed to a mating receptacle housed within the frame, so that the container has a specific orientation.

9. The apparatus of claim 8, wherein each reagent container has more than four sides.

10. The apparatus of claim 2, wherein the probe further comprises a fluid level sensor for determining the volume of reagent within a container.

11. The apparatus of claim 2, wherein a reagent container has a cap with a septum that is penetrated by the probe upon insertion of the probe into the container and that restores to a form that inhibits reagent evaporation upon withdrawal of the probe from the container.

12. The apparatus of claim 11, wherein the septum comprises a plurality of sectors that are separated to form flaps upon first insertion of the probe into the container.

13. The apparatus of claim 2, wherein a reagent container has a cap with a septum that is penetrated by the probe upon insertion of the probe into the container and that cleans an outer surface of the probe upon withdrawal of the probe from the container.

14. The apparatus of claim 1, further comprising a washing station housed within the frame for cleaning the probe after administration of a reagent to a sample.

15. The apparatus of claim 1, further comprising a mixing station housed within the frame for mixing two or more reagents prior to administration of a mixture to a sample.

16. The apparatus of claim 1, wherein the sensor is a camera and wherein at least one identification comprises a two-dimensional arrangement of elements on a carrier, wherein an image of the identification is captured by the camera.

17. The apparatus of claim 16, wherein the identification is in the form of a two-dimensional high-resolution symbology code.

18. The apparatus of claim 16, wherein the identification is in the form of a two dimensional data matrix.

19. The apparatus of claim 16, wherein the identification comprises human-readable text.

20. The apparatus of claim 16, wherein the identification is the biological sample.

21. The apparatus of claim 16, wherein the camera further captures an image of the biological sample.

22. The apparatus of claim 1, wherein at least one carrier is a microscope slide.

23. The apparatus of claim 1, wherein at least one drawer further comprises a processing tank for immersing a carrier into a fluid used for pre-treatment of the biological sample on the carrier, the pre-treatment being administered prior to processing of the sample.

24. The apparatus of claim 23, wherein the carrier rack of the at least one drawer comprises a carrier holder that rotates the carrier into a first orientation prior to the pretreatment and that rotates the carrier into a second orientation prior to the processing.

25. The apparatus of claim 24, wherein the first orientation is substantially vertical and the second orientation is substantially horizontal.

26. The apparatus of claim 1, wherein a carrier rack comprises a temperature control element for controlling the temperature of a biological sample during processing.

27. A method of processing of a plurality of biological samples on sample carriers having respective identifications, the processing of each sample being conducted according to a respective sequence of protocol steps, comprising the steps of:
providing an apparatus comprising:
a frame;
a robotic reagent dispensing head within the frame that performs ongoing robotic processing, including dispensing of reagents; and
a plurality of drawers within the frame, each drawer comprising a respective carrier rack for supporting at least one carrier; and
inserting a first carrier having a first biological sample onto a carrier rack of a first drawer;
inserting a second carrier having a second biological sample onto a carrier rack of a second drawer;
determining the first-completed sample, being whichever one of the first biological sample and the second biological sample whose processing is completed prior to the completion of the processing of the other biological sample;
removing the first-completed sample from the apparatus without interrupting the dispensing of reagents onto the other biological sample.

28. The method of claim 27, wherein the processing includes biological staining.

29. The method of claim 27, wherein the processing includes in-situ hybridization.

30. The method of claim 27, wherein the removing step includes opening the drawer having the first-completed sample.

31. A method of processing of a plurality of biological samples on sample carriers having respective identifications, the processing of each sample being conducted according to a respective sequence of protocol steps, comprising the steps of:
providing an apparatus comprising:
a frame;
a robotic reagent dispensing head within the frame that performs ongoing robotic processing, including dispensing of reagents; and
a plurality of drawers within the frame, each drawer comprising a respective carrier rack for supporting at least one carrier; and
inserting a first carrier having a first biological sample onto a carrier rack of a first drawer;
commencing the processing of the first biological sample;
inserting a second carrier having a second biological sample onto a carrier rack of a second drawer without interrupting the dispensing of reagents onto the first biological sample with the robotic reagent dispensing head;
removing the first carrier from the carrier rack of the first drawer without interrupting the ongoing robotic processing of the second biological sample; and
commencing the processing of the second biological sample, prior to completion of the processing of the first biological sample, without interrupting the processing of the first biological sample.

32. The method of claim 31, wherein the processing includes biological staining.

33. The method of claim 31, wherein the processing includes in-situ hybridization.

* * * * *